US011324787B2

(12) United States Patent
Lindstedt et al.

(10) Patent No.: US 11,324,787 B2
(45) Date of Patent: May 10, 2022

(54) ANALYTICAL METHODS AND ARRAYS FOR USE IN THE SAME

(71) Applicant: SENZAGEN AB, Lund (SE)

(72) Inventors: Malin Marie Lindstedt, Södra Sandby (SH); Carl A. K. Borrebaeck, Lund (SE); Henrik Johansson, Malmö (SE); Ann-Sofie Albrekt, Teckomatorp (SE); Kathrin Stephanie Zeller, Lund (SE); Aakash Chawade, Lund (SE); Tim Carl Sewe Lindberg, Lund (SE); Andy Andreas Sebastian Forreryd, Malmö (SE)

(73) Assignee: SENZAGEN AB, Lund (SE)

( * ) Notice: Subject to any disclaimer, the term of this patent is extended or adjusted under 35 U.S.C. 154(b) by 12 days.

(21) Appl. No.: 16/084,788

(22) PCT Filed: Mar. 22, 2017

(86) PCT No.: PCT/EP2017/056878
§ 371 (c)(1),
(2) Date: Sep. 13, 2018

(87) PCT Pub. No.: WO2017/162773
PCT Pub. Date: Sep. 28, 2017

(65) Prior Publication Data
US 2019/0083556 A1   Mar. 21, 2019

(30) Foreign Application Priority Data

Jan. 5, 2017   (GB) .................................. 1700138.9

(51) Int. Cl.
| | |
|---|---|
| *A61K 35/763* | (2015.01) |
| *C12Q 1/6876* | (2018.01) |
| *A61P 35/00* | (2006.01) |
| *A61K 31/437* | (2006.01) |
| *A61K 39/395* | (2006.01) |
| *C07K 16/28* | (2006.01) |
| *A61K 39/00* | (2006.01) |

(52) U.S. Cl.
CPC .......... *A61K 35/763* (2013.01); *A61K 31/437* (2013.01); *A61K 39/3955* (2013.01); *A61P 35/00* (2018.01); *C07K 16/2818* (2013.01); *C12Q 1/6876* (2013.01); *A61K 2039/505* (2013.01); *C12Q 2600/106* (2013.01); *C12Q 2600/148* (2013.01)

(58) Field of Classification Search
None
See application file for complete search history.

(56) References Cited

U.S. PATENT DOCUMENTS

| | | |
|---|---|---|
| 4,376,110 A | 3/1983 | David et al. |
| 4,486,530 A | 12/1984 | David et al. |
| 5,856,090 A | 1/1999 | Epstein |
| 6,689,936 B1 | 2/2004 | Burgeson et al. |
| 6,998,249 B1 | 2/2006 | McKim |
| 7,615,361 B2 | 11/2009 | McKim |
| 8,703,431 B2 | 4/2014 | Groux et al. |
| 9,255,295 B2 | 2/2016 | Groux et al. |
| 2009/0081783 A1 | 3/2009 | Bechetoille et al. |
| 2009/0208985 A1 | 8/2009 | Katagiri et al. |
| 2009/0305276 A1 | 12/2009 | McKim |
| 2011/0004414 A1 | 1/2011 | Mckim |
| 2012/0179381 A1 | 7/2012 | McKim |
| 2013/0315832 A1 | 11/2013 | Stoian et al. |

FOREIGN PATENT DOCUMENTS

| | | |
|---|---|---|
| EP | 0649901 A1 | 10/1994 |
| EP | 1905843 A1 | 4/2008 |
| EP | 1995595 A1 | 11/2008 |
| EP | 2835640 A1 | 2/2015 |
| FR | 2879747 A1 | 6/2006 |
| JP | 2008-263917 A | 11/2008 |
| WO | 88/06630 A1 | 9/1988 |
| WO | 98/37186 A1 | 8/1998 |
| WO | 99/30743 A1 | 6/1999 |
| WO | 01/17343 A1 | 3/2001 |
| WO | 01/023886 A1 | 4/2001 |
| WO | 03/050271 A2 | 6/2003 |
| WO | 2007/103374 A2 | 9/2007 |
| WO | 2008/028882 A1 | 3/2008 |
| WO | 2009/112590 A2 | 9/2009 |
| WO | 2009/148669 A1 | 12/2009 |
| WO | 2010/031799 A1 | 3/2010 |
| WO | 2011/107611 A2 | 9/2011 |
| WO | 2011/107614 A2 | 9/2011 |
| WO | 2012/034132 A2 | 3/2012 |
| WO | 2012/056236 A2 | 5/2012 |
| WO | 2012068474 A2 | 5/2012 |
| WO | 2012/172370 A1 | 12/2012 |
| WO | 2013/021210 A1 | 2/2013 |
| WO | 2013/160882 A1 | 10/2013 |
| WO | 2019/057977 A1 | 3/2019 |

OTHER PUBLICATIONS

Sinnerling et al., 2015, Front. Immunol. vol. 6: 1-10.*
Balan et al., 2014, J. Immunol. vol. 193: 1622-1635.*
Rodrigues et al., 2013, PLos one, vol. 8: 1-11.*
Reinartz et al., 2016, PLOS one pp. 1-10.*
Zuidschewwoude et al., 2017, PLOS one, pp. 1-15.*
Kimber, et al., "Allergic contact dermatitis" International Immunopharmacology (2002) 2:201-211.
Kimber, et al., "Classification of contact allergens according to potency: proposals" Food Chem. Toxicol. (2003) 41:1799-1809.
Kligman, A.M., "The identification of contact allergens by human assay. 3. The maximization test: a procedure for screening and rating contact sensitizers" J. Invest. Dermatol (1966) 47(5):393-409.

(Continued)

*Primary Examiner* — Amy E Juedes
(74) *Attorney, Agent, or Firm* — Robert C. Netter, Jr.; Dann, Dorfman, Herrell & Skillman

(57) ABSTRACT

The present invention relates to a method for identifying the skin sensitizer potency of a test agent, and arrays and analytical kits for use in such methods.

3 Claims, 17 Drawing Sheets

(56) References Cited

OTHER PUBLICATIONS

Figure 1:
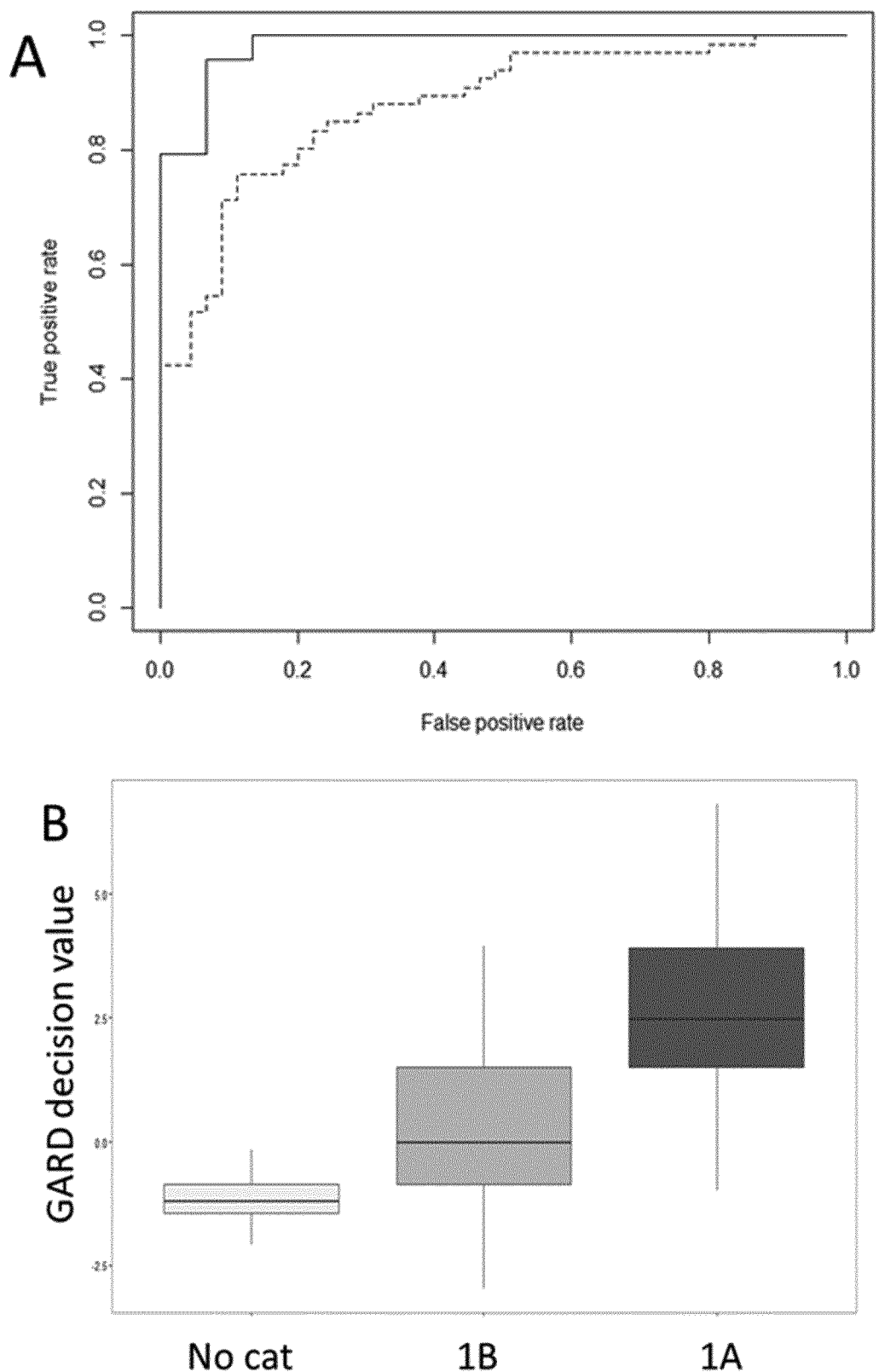

Lambrechts, et al., "Gene markers in dendritic cells unravel pieces of the skin sensitization puzzle" Toxicology Letters (2010) 196:95-103.
Larsson, et al., "Functional and transcriptional profiling of MUTZ-3, a myeloid cell line acting as a model for dendritic cells" Immunology (2006) 117:156-166.
Lindstedt, et al., "Genomic and functional delineation of dendritic cells and memory T cells derived from grass pollen-allergic patients and healthy individuals" Intl. Immunol. (2005) 17(4):401-409.
Masterson, et al., "MUTZ-3, a human cell line model for the cytokine-induced differentiation of dendritic cells from CD34+ precursors" Blood (2002) 100(2):701-703.
Patlewicz, et al., "Skin-sensitization structure-activity relationships for aldehydes" Contact Dermatitis (2001) 44:331-336.
Rasaiyaah, et al., "Dendritic cells and myeloid leukaemias: plasticity and commitment in cell differentiation" British J. Haematology (2007) 138:281-290.
Ryan, et al., "Activity of human contact allergens in the murine local lymph node assay" Contact Dermatitis (2000) 43:95-102.
Sakaguchi, et al., "Development of an in vitro skin sensitization test using human cell lines; human Cell Line Activation Test (h-CLAT) II. An inter-laboratory study of the h-CLAT" Toxicology in Vitro (2006) 20:774-784.
Santegoets, et al., "A CD34+ human cell line model of myeloid dendritic cell differentiation: evidence for a CD14+CD11b+ Langerhans cell precursor" J. Leukocyte Biol. (2006) 80:1337-1344.
National Toxicology Program, "The Murine Local Lymph Node Assay: A Test Method for Assessing the Allergic Contact Dermatitis Potential of Chemicals/Compounds" (1999) obtained at http://iccvam.niehs.nih.gov/docs/immunotox_docs/llna/llnarep.pdf.
Warbrick, et al., "Influence of application vehicle on skin sensitization to methylchloroisothiazolinone/methylisothiazolinone: an analysis using the local lymph node assay" Contact Dermatitis (1999) 41:325-329.
Wikipedia, "Hypersensitivity" (2015) obtained at https://en.wikipedia.org/wiki/Hypersensitivity.
Genbank Accession No. NM_004104, "*Homo sapiens* fatty acid synthase (FASN), mRNA" (2015) obtained at http://www.ncbi.nlm.nih.gov/nuccore/NM_004104.
Genbank Accession No. NM_001442, "*Homo sapiens* fatty acid binding protein 4 (FABP4), mRNA" (2016) obtained at http://www.ncbi.nlm.nih.gov/nuccore/NM_001442.
Takenouchi, et al., "Predictive performance of the human Cell Line Activation Test (h-CLAT) for lipophilic chemicals with high octanol-water partition coefficients" J. Toxicol. Sci. (2013) 38(4):599-609.
Nukada, et al., "Prediction of skin sensitization potency of chemicals by human Cell Line Activation Test (h-CLAT) and an attempt at classifying skin sensitization potency" Toxicology in Vitro (2012) 26:1150-1160.
Nukada, et al., "Predictive performance for human skin sensitizing potential of the human cell line activation test (h-CLAT)" Contact Dermatitis (2011) 65:343-353.
Ashikaga, et al., "A Comparative Evaluation of In Vitro Skin Sensitisation Tests: The Human Cell-line Activation Test (h-CLAT) versus the Local Lymph Node Assay (LLNA)" Altern. Lab Anim. (2010) 38(4):275-84.
Wong, et al., "Evaluation of a High-Throughput Peptide Reactivity Format Assay for Assessment of the Skin Sensitization Potential of Chemicals" Front Pharmacol (2016) 7:53.
Alepee, et al., "Prospective multicentre study of the U-SENS test method for skin sensitization testing" Toxicology in Vitro (2015) 30:373-382.
Ramirez, et al., "Intra- and inter-laboratory reproducibility and accuracy of the LuSens assay: A reporter gene-cell ine to detect keratinocyte activation by skin sensitizers" Toxicology in Vitro (2016) 32:278-286.
Ramirez, et al., "LuSens: A keratinocyte based ARE reporter gene assay for use in integrated testing strategies for skin sensitization hazard identification" Toxicology in Vitro (2014) 28:1482-1497.
Strickland, et al., "Integrated decision strategies for skin sensitization hazard" J. Appl. Toxicol. (2016) 36:1150-1162.
McMillan, et al., "Predicting skin sensitisation using a decision tree integrated testing strategy with an in silico model and in chemico/in vitro assays" Regulatory Toxicol. Pharmacol. (2016) 76:30-38.
Hirota, et al., "Evaluation of combinations of in vitro sensitization test descriptors for the artificial neural network-based risk assessment model of skin sensitization" J. Appl. Toxicol (2015) 35:1333-1347.
Natsch, et al., "A dataset on 145 chemicals tested in alternative assays for skin sensitization undergoing prevalidation" J. Appl. Toxicol. (2013) 33:1337-1352.
Nukada, et al., "Data integration of non-animal tests for the development of a test battery to predict the skin sensitizing potential and potency of chemicals" Toxicology in Vitro (2013) 27:609-618.
Takenouchi, et al., "Test battery with the human cell line activation test, direct peptide reactivity assay and DEREK based on a 139 chemical data set for predicting skin sensitizing potential and potency of chemicals" J. Appl. Toxicol. (2015) 35:1318-1332.
Van Der Veen, et al., "Evaluating the performance of integrated approaches for hazard identification of skin sensitizing chemicals" Regulatory Toxicol. Pharmacology (2014) 69:371-379.
Bausch, et al., "Intralaboratory validation of four in vitro assays for the prediction of the skin sensitizing potential of chemicals" Toxicology in Vitro (2011) 25:1162-1168.
Saito, et al., "An in vitro skin sensitization assay termed EpiSensA for broad sets of chemicals including lipophilic chemicals and pre/pro-haptens" Toxicology in Vitro (2017) 40:11-25.
Strickland, et al., "Multivariate models for prediction of human skin sensitization hazard" J. Appl. Toxicol. (2017) 37 (3):347-360.
Urbisch, et al., "Peptide reactivity associated with skin sensitization: The QSAR Toolbox and TIMES compared to the DPRA" Toxicology in Vitro (2016) 34:194-203.
Urbisch, et al., "Assessment of Pre- and Pro-haptens Using Nonanimal Test Methods for Skin Sensitization" Chem. Res. Toxicol. (2016) 29(5):901-13.
Parise, et al., "Skin sensitizer identification by IL-8 secretion and CD86 expression on THP-1 cells" Toxicology in Vitro (2015) 30:318-324.
Avonto, et al., "A fluorescence high throughput screening method for the detection of reactive electrophiles as potential skin sensitizers" Toxicol Applied Pharmacol. (2015) 289:177-184.
Chittiboyina, et al., "Alternative Testing Methods for Skin Sensitization: NMR Spectroscopy for Probing the Reactivity and Classification of Potential Skin Sensitizers" Chem. Res. Toxicol. (2015) 28:1704-1714.
Kimura, et al., "Optimization of the IL-8 Luc assay as an in vitro test for skin sensitization" Toxicology in Vitro (2015) 29:1816-1830.
Yamamoto, et al., "A novel in chemico method to detect skin sensitizers in highly diluted reaction conditions" J. Appl. Toxicol. (2015) 35:1348-1360.
Fujita, et al., "Development of a prediction method for skin sensitization using novel cysteine and lysine derivatives" J. Pharmacol. Toxicol. Methods (2014) 70:94-105.
R Development Core Team, "R: A language and environment for statistical computing" (2008) obtained at https://www.r-project.org/.
National Institutes of Health, "Comparative LLNA: BrdU-FC, Traditional LLNA, Guinea Pig Skin Sensitization, and Human Data Appendix C" (2008).
Gildea, et al., "Identification of Gene Expression Changes Induced by Chemical Allergens in Dendritic Cells: Opportunities for Skin Sensitization Testing" J. Investigative Dermatol. (2006) 126:1813-1822.
Oestreicher, et al., "Molecular classification of psoriasis disease-associated genes through pharmacogenomic expression profiling" Pharmacogenomics J. (2001) 1:272-287.
Rani, et al., "Novel interferon-beta-induced gene expression in peripheral blood cells" J. Leukocyte Biol. (2007) 82: 1353-1360.
Michiels, et al., "Prediction of cancer outcome with microarrays: a multiple random validation strategy" Lancet (2005) 365:488-492.

(56) References Cited

OTHER PUBLICATIONS

Slonim, D.K., "Post-analysis follow-up and validation of microarray experiments" Nature Genetics Supplement (2002) 32:502-508.
James, G., et al., "An Introduction to Statistical Learning—with Applications in R", Eds. Casella, et al., Springer, New York (2013) pp. 1-426.
Vandebriel, et al., "Keratinocyte gene expression profiles discriminate sensitizing and irritating compounds" Toxicol. Sci. (2010) 117(1):81-9.
Pascual, et al., "A genomic approach to human autoimmune diseases" Annual Review of Immunology (2010) 28:535-571.
Albrekt, et al. "Skin sensitizers differentially regulate signaling pathways in MUTZ-3 cells in relation to their individual potency" BMC Pharmacology and Toxicology (2014) 15:5.
Arkusz, et al., "Prediction of the contact sensitizing potential of chemicals using analysis of gene expression changes in human THP-1 monocytes" Toxicology Letters (2010) 199:51-59.
Cluzel-Tailharadt, et al., "Chemicals with weak skin sensitizing properties can be identified using low-density microarrays on immature dendritic cells" Toxicology Letters (2007) 174:98-109.
Dos Santos, et al., "Progress on the development of human in vitro dendritic cell based assays for assessment of the sensitizing potential of a compound" Toxicology and Applied Pharmacology (2009) 236:372-382.
Johansson, et al., "A genomic biomarker signature can predict skin sensitizers using a cell-based in vitro alternative to animal tests" BMC Genomics (2011) 12:399.
Johansson, et al., "The GARD assay for assessment of chemical skin sensitizers" Toxicology in Vitro (2013) 27:1163-1169.
Lambrechts, et al., "Assessment of Chemical Skin-Sensitizing Potency by an In Vitro Assay Based on Human Dendritic Cells" Toxicological Sciences (2010) 116:122-129.
Martino, et al., "Blood DNA Methylation Biomarkers Predict Clinical Reactivity in Food-Sensitized Infants" J. Allergy Clin. Immunol. (2015) 135:1319-1328.
Schoeiers, et al., "Microarray analyses in dendritic cells reveal potential biomarkers for chemical-induced skin sensitization" Molecular Immunology (2007) 44:3222 3233.
Akhavan, et al., "The Relationship Between Atopic Dermatitis and Contact Dermatitis" Clinics Dermatology (2003) 21:158-162.
Basketter, et al., "Categorization of Chemicals According to Their Relative Human Skin Sensitizing Potency" Dermatitis (2014) 25:11-21.
Basketter, et al., "Evaluation of the skin sensitizing potency of chemicals by using the existing methods and considerations of relevance for elicitation" Contact Dermatitis (2005) 52(1):39-43.
Basketter, et al., "Local lymph node assay—validation, conduct and use in practice" Food Chem. Toxicol. (2002) 40:593-598.
Better, et al. "*Escherichia coli* secretion of an active chimeric antibody fragment" Science (1988) 240(4855):1041-3.
Bird, et al. "Single-chain antigen-binding proteins" Science (1988) 242(4877):423-6.
Clackson, et al., "Making antibody fragments using phage display libraries" Nature (1991) 352(6336):624-8.
Collett. et al., "Production and processing of aptamer microarrays" Methods (2005) 37:4-15.
Daugherty, et al., "Antibody affinity maturation using bacterial surface display" Protein Eng. (1998) 11(9):825-32.
Daugherty, et al., "Development of an optimized expression system for the screening of antibody libraries displayed on the *Escherichia coli* surface" Protein Eng. (1999) 12(7):613-21.
European Union, "Directive 2003/15/EC of the European Parliament and of the Council of Feb. 27, 2003 amending Council Directive 76/768/EEC on the approximation of the laws of the Member States relating to cosmetic products" Official Journal of the European Union (2003) L66:26-35.
Fonacier, et al., "Allergic skin diseases" J. Allergy Clin. Immunol. (2010) 125:S138-49.
Griem, et al., "Proposal for a risk assessment methodology for skin sensitization based on sensitization potency data" Regulatory Toxicol. Pharmacol. (2003) 38:269-290.
Gunneriusson, et al., "Staphylococcal Surface Display of Immunoglobulin A (IgA)- and IgE-Specific In Vitro-Selected Binding Proteins (Affibodies) Based on *Staphylococcus aureus* Protein A" Applied Environmental Microbiol. (1999) 65:4134-4140.
Hanes, et al., "In vitro selection and evolution of functional proteins by using ribosome display" Proc. Natl. Acad. Sci. (1997) 94:4937-4942.
He, et al., "Antibody-ribosome-mRNA (ARM) complexes as efficient selection particles for in vitro display and evolution of antibody combining sites" Nucleic Acids Research (1997) 25(24):5132-5134.
Hurrell, J.G.R., "Monoclonal Hybridoma Antibodies: Techniques and applications" (1982) CRC Press, Boca Raton, Florida, pp. 1-57.
Huston, et al., "Protein engineering of antibody binding sites: Recovery of specific activity in an anti-digoxin single-chain Fv analogue produced in *Escherichia coli*" Proc. Natl. Acad Sci. (1988) 85:5879-5883.
Jenkins, et al., "Arrays for protein expression profiling: Towards a viable alternative to two-dimensional gel electrophoresis?" Proteomics (2001) 1:13-29.
Johansson, et al., "Genomic Allergen Rapid Detection In-House Validation—A Proof of Concept" Toxicological Sci. (2014) 139(2):362-370.
Kenan, et al., "In Vitro Selection of Aptamers from RNA Libraries" Methods Mol. BioL (1999) 118:217-31.
Kieke, et al., "Selection of functional T cell receptor mutants from a yeast surface-display library" Proc. Natl. Acad. Sci. (1999) 96:5651-5656.
Lal, et al., "Antibody arrays: an embryonic but rapidly growing technology" Drug Discov. Today (2002) 7(18 Suppl):143-9.
Magnusson, et al., "The identification of contact allergens by animal assay. The guinea pig maximization test" J. Invest. Dermatol. (1969) 52(3):268-76.
Marks, et al. "By-passing immunization. Human antibodies from V-gene libraries displayed on phage" J. Mol. Biol. (1991) 222(3):581-97.
Morrison, et al. "Chimeric human antibody molecules: mouse antigen-binding domains with human constant region domains." Proc. Natl. Acad. Sci. (1984) 81(21):6851-5.
Mortz, et al., "Prevalence of atopic dermatitis, asthma, allergic rhinitis, and hand and contact dermatitis in adolescents. The Odense Adolescence Cohort Study on Atopic Diseases and Dermatitis" British J. Dermatology (2001) 144:523-532.
Nemoto, et al. "In vitro virus: bonding of mRNA bearing puromycin at the 3'-terminal end to the C-terminal end of its ancoded protein on the ribosome in vitro" FEBS Lett. (1997) 414(2):405-8.
Nielsen, et al., "Allergic Contact Sensitization in an Adult Danish Population: Two Cross-sectional Surveys Eight Years Apart (The Copenhagen Allergy Study)" Acta Derm. Venereol. (2001) 81:31-34.
European Union, "44. Regulation (EC) No. 1907/2006 of the European Parliament and of the Council of Dec. 18, 2006." (2006) Official Journal of the European Union, L396:1-849.
Santi, et al., "Bacteriophage Lambda Display of Complex cDNA Libraries: A New Approach to Functional Genomics" J. Mol. Biol. (2000) 296:497-508.
Schervish, M.J., "A review of multivariate analysis" Stat. Sci. (1987) 2(4):396-413.
Shusta, et al., "Yeast Polypeptide Fusion Surface Display Levels Predict Thermal Stability and Soluble Secretion Efficiency" J Mol. Biol. (1999) 292:949-956.
Skerra, et al. "Assembly of a functional immunoglobulin Fv fragment in *Escherichia coli*" Science (1988) 240 (4855):1038-41.
Smith, G.P. "Filamentous fusion phage: novel expression vectors that display cloned antigens on the virion surface" Science (1985) 228(4705):1315-7.
Steinman, R.M., "The dendritic cell system and its role in immunogenicity" Annu. Rev. Immunol. (1991) 9:271-96.
Trygg, et al., "Orthogonal Projections to Latent Structures (O-PLS)" J. Chemometrics (2002) 16:119-28.

(56) References Cited

OTHER PUBLICATIONS

Ward, et al. "Binding activities of a repertoire of single immunoglobulin variable domains secreted from *Escherichia coli*" Nature (1989) 341(6242):544-6.

Winter, et al., "Man-made antibodies" Nature (1991) 349(6307):293-9.

Wold, H., "11—Path Models with Latent Variables: The NIPALS Approach" Quantitative Sociology: International Perspectives on Mathematical and Statistical Modeling (1975) 307-357.

World Health Organization "International Programme on Chemical Safety [IPCS] Harmonization Project Document No. 5: Skin Sensitization in Chemical Risk Assessment" (2008) WHO Press, Geneva, Switzerland.

Ionnidis, J.P.A., "Why most published research findings are false" PloS Med. (2005) 2(8):e124.

Cheung, et al., "Genetics of quantitative variation in human gene expression" Cold Spring Harbor Symposia Quant. Biol. (2003) LXVIII:403-407.

Baker, et al., "The Central Role of Receiver Operating Characteristic (ROC) Curves in Evaluating Tests for the Early Detection of Cancer" J. Natl. Cancer Institute (2003) 95(7):511-515.

Leek, et al. "Surrogate Variable Analysis" R package version 3.10.0. (2014) obtained at http://bioconductor.org/packages/release/bioc/html/sva.html.

Lee-Sayer, et al., "The where, when, how, and why of hyaluronan binding by immune cells" Front Immunol. (2015) 6:150.

Li, et al., "Octameric Structure of the Human Bifunctional Enzyme PAICS in Purine Biosynthesis" J. Mol. Biol. (2007) 366:1603-1614.

Liaw, et al., "Classification and regression by random forest" R News (2002) 2(3): 18-22.

Lu, et al., "3 beta-Hydroxysteroid-D 24 Reductase (DHCR24) Protects Neuronal Cells from Apoptotic Cell Death Induced by Endoplasmic Reticulum (ER) Stress" PLoS ONE (2014) 9(1):e86753.

Luechtefeld, et al., "Probabilistic hazard assessment for skin sensitization potency by dose-response modeling using feature elimination instead of quantitative structure—activity relationships" J. Appl. Toxicol. (2015) 35(11)1361-1371.

Martin, et al., "Mechanisms of chemical-induced innate immunity in allergic contact dermatitis" Allergy (2011) 66:1152-1163.

Migdal, et al., "Reactivity of Chemical Sensitizers Toward Amino Acids In Cellulo Plays a Role in the Activation of the Nrf2-ARE Pathway in Human Monocyte Dendritic Cells and the THP-1 Cell Line" Toxicological Sci. (2013) 133(2):259-274.

Natsch, et al., "Skin Sensitizers Induce Antioxidant Response Element Dependent Genes: Application to the In Vitro Testing of the Sensitization Potential of Chemicals" Toxicological Sci. (2008) 102(1):110-119.

Natsch, et al. "Chemical basis for the extreme skin sensitization potency of (E)-4-(ethoxymethylene)-2-phenyloxazol-5(4H)-one" Chem Res. Toxicol. (2010) 23(12): 1913-20.

Natsch, et al., "Predicting Skin Sensitizer Potency Based on In Vitro Data from KeratinoSens and Kinetic Peptide Binding: Global Versus Domain-Based Assessment" Toxicological Sci. (2015) 143(2):319-332.

Natsch, et al., "Relating Skin Sensitizing Potency to Chemical Reactivity: Reactive Michael Acceptors Inhibit NF-kB Signaling and Are Less Sensitizing than SNAr- and SN2-Reactive Chemicals" Chem. Res. Toxicol. (2011) 24:2018-2027.

Natsch, A., "The Nrf2-Keap1-ARE Toxicity Pathway as a Cellular Sensor for Skin Sensitizers—Functional Relevance and a Hypothesis on Innate Reactions to Skin Sensitizers" Toxicological Sci. (2010) 113(2):284-292.

Organization for Economic Co_Operation and Development (OECD) "The Adverse Outcome Pathway for Skin Sensitisation Initiated by Covalent Binding to Proteins, Part 1: Scientific Evidence" Environment, Health and Safety Publications, Series on Testing and Assessment No. 168 (2012) OECD, Paris, France.

Peiser, et al., "Allergic contact dermatitis: epidemiology, molecular mechanisms, in vitro methods and regulatory aspects" Cell. Mol. Life Sci. (2012) 69:763-781.

Peng, et al., "Tetraspanins CD9 and CD81 are molecular partners of trimeric FceRI on human antigen-presenting cells" Allergy (2011) 66(5):605-11.

Piccolo, et al., "A single-sample microarray normalization method to facilitate personalized-medicine workflows" Genomics (2012) 100:337-344.

Piccolo, et al. "SCAN.UPC: Single-channel array normalization (SCAN) and Universal exPression Codes (UPC)" Bioconductor version: Release (3.3). (2016) obtained at https://www.bioconductor.org/packages/release/bioc/html/SCAN.UPC.html.

Piroird, et al., "The Myeloid U937 Skin Sensitization Test (U-SENS) addresses the activation of dendritic cell event in the adverse outcome pathway for skin sensitization" Toxicology in Vitro (2015) 29:901-916.

Qiu, et al., "RNA interference against TMEM97 inhibits cell proliferation, migration, and invasion in glioma cells" Tumor Biol. (2015) 36:8231-8238.

European Union "Regulation (EC) No. 1223/2009 of the European Parliament and of the Council of Nov. 30, 2009 on cosmetic products" Official Journal of the European Union (2009) L342:59-209.

European Union "Regulation (EC) No. 1272/2008 of the European Parliament and of the Council of Dec. 16, 2008 on classification, labelling and packaging of substances and mixtures, amending and repealing Directives 67/548/EEC and 1999/45/EC, and amending Regulation (EC) No. 1907/2006" Official Journal of the European Union (2008) L353:1-1355.

Richmond, et al., "The Nucleotide Synthesis Enzyme CAD Inhibits NOD2 Antibacterial Function in Human Intestinal Epithelial Cells" Gastroenterology (2012) 142(7): 1483-92.

Roberts, et al., "Electrophilic chemistry related to skin sensitization. Reaction mechanistic applicability domain classification for a published data set of 106 chemicals tested in the mouse local lymph node assay" Chem. Res. Toxicol. (2007) 20(1):44-60.

Roggen, et al., "Sens-it-iv: A European Union project to develop novel tools for the identification of skin and respiratory sensitizers" Toxicology in Vitro (2013) 27:1121.

Schulz, et al., "Aryl hydrocarbon receptor activation affects the dendritic cell phenotype and function during allergic sensitization" Immunobiology (2013) 218:1055-1062.

Sing, et al., "ROCR: visualizing classifier performance in R" Bioinformatics (2005) 21(20):3940-3941.

Singh, et al., "Increasing the complexity of chromatin: functionally distinct roles for replication-dependent histone H2A isoforms in cell proliferation and carcinogenesis" Nucleic Acids Research (2013) 41(20):9284-9295.

Teunis, et al., "International Ring Trial of the Epidermal Equivalent Sensitizer Potency Assay: Reproducibility and Predictive Capacity" ALTEX (2014) 31(3):251-68.

Tsujita-Inoue, et al., "Skin sensitization risk assessment model using artificial neural network analysis of data from multiple in vitro assays" Toxicology in Vitro (2014) 28:626-639.

Urbisch, et al., "Assessing skin sensitization hazard in mice and men using non-animal test methods" Regulatory Toxicology and Pharmacology (2015) 71:337-351.

Waterham, et al., "Mutations in the 3beta-Hydroxysterol D24-Reductase Gene Cause Desmosterolosis, an Autosomal Recessive Disorder of Cholesterol Biosynthesis" Am. J. Hum. Genet. (2001) 69:685-694.

Xu, et al., "Structure and Function of the PP2A-Shugoshin Interaction" Molecular Cell (2009) 35:426-441.

Forreryd, et al. "GARD—Genomic Allergen Rapid Detection: a cell-based testing strategy for potency assessment of skin sensitizing chemicals" Conference oral presentation: ICI 2016 International Congress of Immunology, Aug. 21-26, 2016, Melbourne, Australia.

Forreryd, et al., "1127: The GARD assay for potency assessment of skin sensitizing chemicals" Eur. J. Immunol. (2016) 46(Suppl1):11-12.

Lindberg, et al. "Prediction of skin sensitizing potency of chemicals by the alternative cell-based assay GARD" Abstract #2205, Poster Board P135, presented Mar. 15, 2016. Society of Toxicology 55th Annual Meeting and ToxExpo™, Mar. 13-17, 2016, New Orleans, LA.

(56) References Cited

OTHER PUBLICATIONS

Lee, et al., "Predicting full thickness skin sensitization using a support vector machine" Toxicol In Vitro (2014) 28 (8):1413-1423.
Szameit, et al., "Gene expression studies in cultured dendritic cells: new indicators for the discrimination of skin sensitizers and irritants in vitro" Clin. Exper. Allergy (2009) 39(6):856-868.
Lambrechts, et al. "THP-1 monocytes but not macrophages as a potential alternative for CD34 +dendritic cells to identify chemical skin sensitizers" Toxicol. Applied. Pharmacol. (2009) 236(2):221-230.
Bernard, et al., "Comparison of gene expression profiles in human keratinocyte mono-layer cultures, reconstituted epidermis and normal human skin; transcriptional effects of retinoid treatments in reconstituted human epidermis" Experimental Dermatology (2002) 11:59-74.
Python, et al., "Comparative DNA microarray analysis of human monocyte derived dendritic cells and MUTZ-3 cells exposed to the moderate skin sensitizer cinnamaldehyde" Toxicol. Applied Pharmacol. (2009) 239(3):273-283.
Ashby, et al., "Structure activity relationships in skin sensitization using the murine local lymph node assay" Toxicology (1995) 103(3): 177-94.
Basketter, et al., "The skin sensitization potential of resorcinol: experience with the local lymph node assay" Contact Dermatitis (2007) 56:196-200.
Basketter, et al., "Strategies for Identifying False Positive Responses in Predictive Skin Sensitization Tests" Food and Chemical Toxicology (1998) 36:327-333.
Burges, C.J.C., "A Tutorial on Support Vector Machines for Pattern Recognition" Data Mining and Knowledge Discovery (1998) 2:121-167.
Cortes, et al., "Support-Vector Networks" Machine Learning (1995) 20(3):273-297.
Gerberick, et al., "Compilation of Historical Local Lymph Node Data for Evaluation of Skin Sensitization Alternative Methods" Dermatitis (2005) 16(4):157-202.
Gerberick, et al., "Contact Allergenic Potency: Correlation of Human and Local Lymph Node Assay Data" Amer. J. Contact Dermatitis (2001) 12(3):156-161.
Haneke, et al., "ICCVAM Evaluation of the Murine Local Lymph Node Assay: III. Data Analyses Completed by the National Toxicology Program Interagency Center for the Evaluation of Alternative Toxicological Methods" Regulatory Toxicol. Pharmacol. (2001) 34:274-286.
Hooyberghs, et al., "A cell-based in vitro alternative to identify skin sensitizers by gene expression" Toxicol. Applied Pharmacol. (2008) 231:103-111.
Zola, H., "Monoclonal Antibodies: A manual of techniques" 1st ed. (1987) CRC Press, Boca Raton, Florida, pp. 17-61.
Ade, et al., "HMOX1 and NQO1 Genes are Upregulated in Response to Contact Sensitizers in Dendritic Cells and THP-1 Cell Line: Role of the Keap1/Nrf2 Pathway" Toxicological Sci. (2009) 107(2):451-460.
Anderson, et al., "The LLNA: A Brief Review of Recent Advances and Limitations" J. Allergy (2011) 2011:424203.
Natsch, et al., "The intra- and inter-laboratory reproducibility and predictivity of the KeratinoSens assay to predict skin sensitizers in vitro: Results of a ring-study in five laboratories" Toxicology in Vitro (2011) 25:733-744.
Ashikaga, et al., "Development of an in vitro skin sensitization test using human cell lines: The human Cell Line Activation Test (h-CLAT). I. Optimization of the h-CLAT protocol" Toxicology in Vitro (2006) 20:767-773.
Bartz, et al., "Identification of Cholesterol-Regulating Genes by Targeted RNAi Screening" Cell Metabolism (2009) 10:63-75.
Basketter, et al., "Nothing is perfect, not even the local lymph node assay: a commentary and the implications for REACH" Contact Dermatitis (2009) 60:65-69.

Behroozy, et al., "Wet-work Exposure: A Main Risk Factor for Occupational Hand Dermatitis" Safety and Health at Work (2014) 5:175-180.
Benigni, et al., "A data-based exploration of the adverse outcome pathway for skin sensitization points to the necessary requirements for its prediction with alternative methods" Regulatory Toxicology and Pharmacology (2016) 78:45-52.
Bohme, et al. "Kinetic glutathione chemoassay to quantify thiol reactivity of organic electrophiles—application to alpha, beta-unsaturated ketones, acrylates, and propiolates" Chem. Res. Toxicol. (2009) 22(4):742-50.
Breiman, L., "Random Forests" Machine Learning (2001) 45:5-32.
Brodersen, et al., "The balanced accuracy and its posterior distribution" ICPR '10 Proceedings of the 2010 20th International Conference on Pattern Recognition (2010) 3121-3124.
Buchmann, et al., "Regulation of Cellular Genes in a Chromosomal Context by the Retinoblastoma Tumor Suppressor Protein" Mol. Cell. Biol. (1998) 18:4565-4576.
Chipinda, et al., "Haptenation: Chemical Reactivity and Protein Binding" J. Allergy (2011) 2011:839682.
Thomas Reuters, "Key Pathway Advisor (KPA)" (2016) obtained at http://ipscience.thomsonreuters.com/product/metacore.
Copper, et al., "Describing the Validity of Carcinogen Screening Tests" Br. J. Cancer (1979) 39:87-89.
Cottrez, et al., "Genes specifically modulated in sensitized skins allow the detection of sensitizers in a reconstituted human skin model. Development of the SENS-IS assay" Toxicology in Vitro (2015) 29:787-802.
Cottrez, et al., "SENS-IS, a 3D reconstituted epidermis based model for quantifying chemical sensitization potency: Reproducibility and predictivity results from an inter-laboratory study" Toxicology in Vitro (2016) 32:248-260.
Dearden, et al., "Mechanism-Based QSAR Modeling of Skin Sensitization" Chem. Res. Toxicol. (2015) 28:1975-1986.
Diaz-Uriate, et al., "Gene selection and classification of microarray data using random forest" BMC Bioinformatics (2006) 7:3.
Diaz-Uriate, R., "GeneSrF and varSeIRF: a web-based tool and R package for gene selection and classification using random forest" BMC Bioinformatics (2007) 8:328.
Dimitriadou, et al., "Mise Functions of the Department of Statistics (e1071), TU Wien" (2011) obtained at http://cran.r-project.org/web/packages/e1071 /e 1071. pdf.
Dumont, et al., "Analysis of the Local Lymph Node Assay (LLNA) variability for assessing the prediction of skin sensitisation potential and potency of chemicals with non-animal approaches" Toxicology in Vitro (2016) 34:220-228.
Esser, et al., "Contact Sensitizers Induce Skin Inflammation via ROS Production and Hyaluronic Acid Degradation" PLoS ONE (2012) 7(7): e41340.
European Chemicals Agency "Classifying and labelling chemicals: A brief guide to the classification and labelling of chemicals in the EU" (2014) obtained at http://echa.europa.eu:80/documents/10162/13556/echa_clp_leaflet_en.pdf.
European Chemicals Agency "CLP 2015" (2015) obtained at http://echa.europa.eu/clp-2015.
European Chemicals Agency "Clp" (2016) obtained at http://echa.europa.eu/sv/regulations/clp/.
European Chemicals Agency "Guidance on the Application of the CLP Criteria" (2015) obtained at https://echa.europa eu/documents/10162/13562/clp_en.pdf.
Ezendam, et al., "State of the art in non-animal approaches for skin sensitization testing: from individual test methods towards testing strategies" Arch. Toxicol (2016) 90:2861-2883.
Fitzpatrick, et al., "What determines skin sensitization potency: Myths, maybes and realities. The 500 molecular weight cut-off: An updated analysis" J. Appl. Toxicol. (2017) 37:105-116.
Forreryd, et al., "From genome-wide arrays to tailor-made biomarker readout—Progress towards routine analysis of skin sensitizing chemicals with GARD" Toxicology in Vitro (2016) 37:178-188.
Fraker, et al., "Protein and cell membrane iodinations with a sparingly soluble chloroamide, 1,3,4,6-tetrachloro-3a,6a-diphrenylglycoluril" Biochem. Biophys. Res. Commun. (1978) 80(4):849-57.

(56) References Cited

OTHER PUBLICATIONS

Gerberick, et al., "Development of a Peptide Reactivity Assay for Screening Contact Allergens" Toxicological Sci. (2004) 81:332-343.

Gerberick, et al., "Local lymph node assay (LLNA) for detection of sensitization capacity of chemicals" Methods (2007) 41:54-60.

Gonda, et al. "CD44, but not I-selectin, is critically involved in leucocyte migration into the skin in a murine model of allergic dermatitis" Exp. Dermatol (2005) 14(9):700-8.

Harshman, et al., "H1 histones: current perspectives and challenges" Nucleic Acids Research (2013) 41(21):9593-9609.

Hartung, et al., "Chemical regulators have overreached" Nature (2009) 460(7259): 1080-1081.

Heberle, et al., "InteractiVenn: a web-based tool for the analysis of sets through Venn diagrams" BMC Bioinformatics (2015) 16:169.

Higashimoto, et al., "Regulation of I(kappa)B Kinase Complex by Phosphorylation of (Gamma)-Binding Domain of I(kappa)B Kinase (beta) by Polo-like Kinase 1" J. Biol. Chem. (2008) 283(51):35354-35367.

Hoffmann, S., "LLNA Variability: An Essential Ingredient for a Comprehensive Assessment of Non-Animal Skin Sensitization Test Methods and Strategies" Altex (2015) 32(4):379-383.

Hu, et al., "Polo-Like Kinase 1 (PLK1) is Involved in Toll-like Receptor (TLR)-Mediated TNF-αProduction in Monocytic THP-1 Cells" PLoS ONE (2013) 8(10):e78832.

Huang, et al., "De novo synthesis of pyrimidine nucleotides; emerging interfaces with signal transduction pathways" Cell Mol. Life Sci. (2003) 60(2):321-36.

Jaworska, et al., "Bayesian integrated testing strategy (ITS) for skin sensitization potency assessment: a decision support system for quantitative weight of evidence and adaptive testing strategy" Arch. Toxicol. (2015) 89:2355-2383.

Jaworska, et al., "Bayesian integrated testing strategy to assess skin sensitization potency: from theory to practice" J. Appl. Toxicol. (2013) 33:1353-1364.

Jockers, et al., "Different expression of adhesion molecules and tetraspanins of monocytes of patients with atopic aczema" Allergy (2006) 61:1419-1422.

Johnson, et al., "CD44 and its role in inflammation and inflammatory diseases" Inflamm. Allergy Drug Targets (2009) 8(3):208-20.

Johnson, et al., "Adjusting batch effects in microarray expression data using empirical Bayes methods" Biostatistics (2007) 8(1):118-127.

Kohle, et al., "Coordinate regulation of Phase I and II xenobiotic metabolisms by the Ah receptor and Nrf2" Biochem. Pharmacol. (2007) 73(12): 1853-1862.

Lane, et al., "Regulation of mammalian nucleotide metabolism and biosynthesis" Nucleic Acids Research (2015) 43(4):2466-2485.

Lasko, et al., "The use of receiver operating characteristic curves in biomedical informatics" J. Biomed. Informat. (2005) 38:404-415.

Forreyd, A., et al., "Evaluation of high throughput gene expression platforms using a genomic biomarker signature tor prediction of skin sensitization" BMC Genomics (2014) 15:379.

Pradervand, S., et al. "Affymetrix Whole-Transcript Human Gene 1.0 ST array is highly concordant with standard 3' expression arrays" BioTechniques (2008) 44:759-762.

Kang, H., et al. "Research progress of alternative methods in skin sensitization detection" Journal of Hygiene Research (2012) 4:690-694 [Abstract only].

\* cited by examiner

Cell cycle

Immune system

Development

DNA damage and other pathways

Significance (-log p-value)

A

B

ANALYTICAL METHODS AND ARRAYS FOR USE IN THE SAME

This application is a § 371 application of PCT/EP2017/056878, filed Mar. 22, 2017, which claims priority to PCT/EP2016/056465, filed Mar. 23, 2016, and GB 1700138.9, filed on Jan. 5, 2017. The foregoing applications are incorporated by reference herein.

FIELD OF THE INVENTION

The present invention relates to a method for identifying the skin sensitizer potency of a test agent, and arrays and analytical kits for use in such methods.

BACKGROUND

Allergic contact dermatitis (ACD) is an inflammatory skin disease that affects a significant proportion of the population. It is commonly caused by immunological responses towards chemical haptens leading to substantial economic burden for society. Current tests for sensitizing chemicals rely on animal experimentation. Legislation on the registration and use of chemicals within, e.g., the pharmaceutical and cosmetic industries, have stimulated significant research efforts to develop alternative human cell-based assays for the prediction of sensitization. The aim is to replace animal experiments with in vitro tests displaying a higher predictive power.

ACD is characterized by eczema and recurrent episodes of itching [Akhavan, A. and S. R. Cohen, *The relationship between atopic dermatitis and contact dermatitis*. Clin Dermatol, 2003. 21(2): p. 158-62]. The disease affects a significant proportion of the population, with prevalence rates of 7.2% to 18.6% in Europe [Mortz, C. G., et al., *Prevalence of atopic dermatitis, asthma, allergic rhinitis, and hand and contact dermatitis in adolescents. The Odense Adolescence Cohort Study on Atopic Diseases and Dermatitis*. Br J Dermatol, 2001. 144(3): p. 523-32; and Nielsen, N. H., et al., *Allergic contact sensitization in an adult Danish population: two cross-sectional surveys eight years apart (the Copenhagen Allergy Study)*. Acta Derm Venereol, 2001. 81(1): p. 31-4], and the incidence is increasing due to repeated exposure to sensitizing chemicals. ACD is a type IV delayed-type hypersensitivity response caused mainly by reactive T helper 1 (Th1) and interferon (IFN)γ producing $CD8^+$ T cells at site of contact with small chemical haptens in previously exposed, and immunologically sensitized, individuals [Fonacier, L. S., S. C. Dreskin, and D. Y. Leung, *Allergic skin diseases*. J Allergy Clin Immunol. 125(2 Suppl 2): p. S138-49]. Dendritic cells (DC) in the epidermis initiate the immune reactions by responding to haptens bound to self-molecules and activating T cell-mediated immunity.

The REACH (Registration, Evaluation, and Authorisation of Chemicals) regulation requires that all new and existing chemicals within the European Union, involving approximately 30000 chemicals, should be tested for hazardous effects [EC 1907/2006, in Regulation (EC) No 1907/2006]. As the identification of potential sensitizers currently requires animal testing, the REACH legislation will have a huge impact on the number of animals needed for testing. Further, the 7th Amendment to the Cosmetics Directive (76/768/EEC) posed a ban on animal tests for the majority of cosmetic ingredients for human use in 2013. Thus, development of reliable in vitro alternatives to experimental animals for the assessment of sensitizing capacity of chemicals is urgent.

Figure 8:
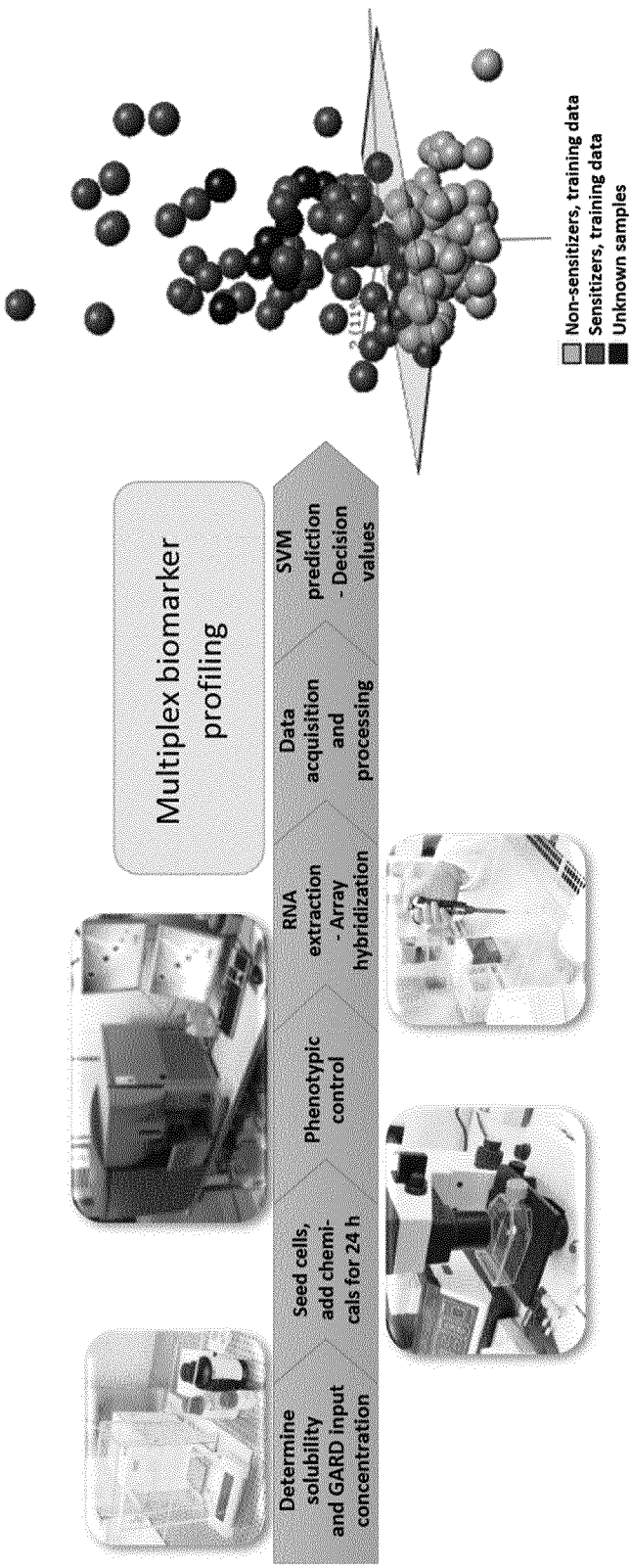

We have developed a human cell-based assay for the prediction of sensitizing chemicals, called Genomic Allergen Rapid Detection, GARD (FIG. 8). For a detailed description, see WO 2012/056236 and Johansson H et al. *The GARD assay for assessment of chemical skin sensitizers*. Toxicology in vitro 2013, which are incorporated herein by reference. By analyzing the transcriptome of dendritic-like cells (e.g., the MUTZ-3 cell line) we have identified a genomic biomarker signature with potent discriminatory ability [Johansson H et al. *A genomic biomarker signature can predict skin sensitizers using a cell-based in vitro alternative to animal tests*. BMC Genomics. 2011; Johansson H et al. *The GARD assay for assessment of chemical skin sensitizers*. Toxicology in vitro 2013; and Johansson H et al. *GARD in-house validation—A proof of concept*. Toxicological Sciences 2014]. Furthermore, the way signaling pathways are engaged by different chemical reactivity groups seems to be associated with sensitizing potency [Albrekt et al. *Skin sensitizers differentially regulate signaling pathways in MUTZ-3 cells in relation to their individual potency*. BMC Pharmacology and Toxicology 2014].

However, to date, non-animal replacements are required for identification of the potency of skin sensitizing chemicals, instead the preferred assay is the mouse Local Lymph Node Assay (LLNA) [Basketter, D. A., et al., *Local lymph node assay—validation, conduct and use in practice*. Food Chem Toxicol, 2002. 40(5): p. 593-8], followed by the Guinea pig maximization test (GPMT) [Magnusson, B. and A. M. Kligman, *The identification of contact allergens by animal assay. The guinea pig maximization test*. J Invest Dermatol, 1969. 52(3): p. 268-76].

An in vitro alternative to these animal models would preferably exhibit improved reliability, accuracy of potency prediction and, importantly, correlation to human reactivity.

DISCLOSURE OF THE INVENTION

Based on previous studies, the GARD assay has proven valuable for skin sensitizer identification. A broader assessment of the human transcriptome using multivariate models has now surprisingly revealed that improved in vitro potency models are also possible.

Accordingly, a first aspect of the invention provides provides a method for determining the skin sensitizing potency of an agent comprising or consisting of the steps of:
 (a) providing a population of dendritic cells or a population of dendritic-like cells;
 (b) exposing the cells provided in step (a) to a test agent; and
 (c) measuring in the cells of step (b) the expression of two or more biomarkers selected from the group defined in Table A;
 wherein the expression of the two or more biomarkers measured in step (c) is indicative of the skin sensitizing potency of the test agent of step (b).

In an additional or alternative embodiment one or more of the biomarkers measured in step (c) is selected from the group defined in Table A(i) and/or Table A(ii).

In an additional or alternative embodiment step (c) comprises or consists of measuring the expression of one or more biomarker listed in Table A(i), for example, 2, 3, 4, 5, 6, 7, 8, 9, 10, 11, 12, 13, 14, 15, 16, 17, 18, 19, or 20 of the biomarkers listed in Table A(i). For example, step (c) may comprise or consist of measuring the expression of all of the biomarkers listed in Table A(i).

The method may include or exclude measuring the expression of HIST1H2BM. The method may include or exclude measuring the expression of HIST1H4B. The method may include or exclude measuring the expression of HIST1H1D. The method may include or exclude measuring the expression of PAICS. The method may include or exclude measuring the expression of HIST1H4D. The method may include or exclude measuring the expression of HIST1H2AL/HIST1H2BN. The method may include or exclude measuring the expression of PLK1. The method may include or exclude measuring the expression of PHGDH. The method may include or exclude measuring the expression of MCM2. The method may include or exclude measuring the expression of MCM7. The method may include or exclude measuring the expression of CD53. The method may include or exclude measuring the expression of KIFC1. The method may include or exclude measuring the expression of WEE1. The method may include or exclude measuring the expression of TMPO. The method may include or exclude measuring the expression of MCM4. The method may include or exclude measuring the expression of PSRC1. The method may include or exclude measuring the expression of RNF149. The method may include or exclude measuring the expression of MCM6. The method may include or exclude measuring the expression of MCM5. The method may include or exclude measuring the expression of FANCA.

In an additional or alternative embodiment step (c) comprises or consists of measuring the expression of one or more biomarkers listed in Table A(ii), for example, 2, 3, 4, 5, 6, 7, 8, 9, 10, 11, 12, 13, 14, 15, 16, 17, 18, 19, 20, 21, 22, 23, 24, or 25 of the biomarkers listed in Table A(ii). For example, step (c) may comprise or consist of measuring the expression of all of the biomarkers listed in Table A(ii).

The method may include or exclude measuring the expression of CAD. The method may include or exclude measuring the expression of MRTO4. The method may include or exclude measuring the expression of TOE1. The method may include or exclude measuring the expression of CDC20. The method may include or exclude measuring the expression of PM20D2. The method may include or exclude measuring the expression of LOC344887. The method may include or exclude measuring the expression of UNG. The method may include or exclude measuring the expression of CDKN1A. The method may include or exclude measuring the expression of HIST1H2BF. The method may include or exclude measuring the expression of HIST1H1B. The method may include or exclude measuring the expression of Transcript ID 7896697. The method may include or exclude measuring the expression of JADE1. The method may include or exclude measuring the expression of KIAA0125. The method may include or exclude measuring the expression of CHRNA5. The method may include or exclude measuring the expression of CHAF1B///MORC3. The method may include or exclude measuring the expression of SEL1L3. The method may include or exclude measuring the expression of SSRP1. The method may include or exclude measuring the expression of FOXM1. The method may include or exclude measuring the expression of LMNB1. The method may include or exclude measuring the expression of HIST1H2AK. The method may include or exclude measuring the expression of CENPA. The method may include or exclude measuring the expression of NCAPH. The method may include or exclude measuring the expression of HIST1H2BB. The method may include or exclude measuring the expression of ATP6V1B2. The method may include or exclude measuring the expression of TRAP1.

In an additional or alternative embodiment step (c) may comprise or consist of measuring the expression of one or more biomarker listed in Table A(iii), for example, 1, 2, 3, 4, 5, 6, or 7 of the biomarkers listed in Table A(iii). For example, step (c) comprises or consists of measuring the expression of all of the biomarkers listed in Table A(iii).

The method may include or exclude measuring the expression of PFAS. The method may include or exclude measuring the expression of TMEM97. The method may include or exclude measuring the expression of DHCR24. The method may include or exclude measuring the expression of FTH1. The method may include or exclude measuring the expression of HIST1H2AE. The method may include or exclude measuring the expression of NQO1. The method may include or exclude measuring the expression of CD44.

In an additional or alternative embodiment step (c) comprises or consists of measuring the expression of three or more of the biomarkers listed in Table A, for example, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, or 52 of the biomarkers listed in Table A. For example, step (c) may comprise or consist of measuring the expression of all of the biomarkers listed in Table A.

The method may include or exclude measuring the expression of HIST1H2BM. The method may include or exclude measuring the expression of HIST1H4B. The method may include or exclude measuring the expression of HISTIH1D. The method may include or exclude measuring the expression of PAICS. The method may include or exclude measuring the expression of HIST1H4D. The method may include or exclude measuring the expression of HIST1H2AL///HIST1H2BN. The method may include or exclude measuring the expression of PLK1. The method may include or exclude measuring the expression of PHGDH. The method may include or exclude measuring the expression of MCM2. The method may include or exclude measuring the expression of MCM7. The method may include or exclude measuring the expression of CD53. The method may include or exclude measuring the expression of KIFC1. The method may include or exclude measuring the expression of WEE1. The method may include or exclude measuring the expression of TMPO. The method may include or exclude measuring the expression of MCM4. The method may include or exclude measuring the expression of PSRC1. The method may include or exclude measuring the expression of RNF149. The method may include or exclude measuring the expression of MCM6. The method may include or exclude measuring the expression of MCM5. The method may include or exclude measuring the expression of FANCA.

The method may include or exclude measuring the expression of CAD. The method may include or exclude measuring the expression of MRTO4. The method may include or exclude measuring the expression of TOE1. The method may include or exclude measuring the expression of CDC20. The method may include or exclude measuring the expression of PM20D2. The method may include or exclude measuring the expression of LOC344887. The method may include or exclude measuring the expression of UNG. The method may include or exclude measuring the expression of CDKN1A. The method may include or exclude measuring the expression of HIST1H2BF. The method may include or exclude measuring the expression of HIST1H1B. The method may include or exclude measuring the expression of Transcript ID 7896697. The method may include or exclude measuring the expression of JADE1. The method may include or exclude measuring the expression of KIAA0125. The method may include or exclude measuring the expression of CHRNA5. The method may include or exclude measuring the expression of CHAF1B///MORC3. The method may include or exclude measuring the expression of SEL1L3. The method may include or exclude measuring the expression of SSRP1. The method may include or exclude measuring the expression of FOXM1. The method may include or exclude measuring the expression of LMNB1. The method may include or exclude measuring the expression of HIST1H2AK. The method may include or exclude measuring the expression of CENPA. The method may include or exclude measuring the expression of NCAPH. The method may include or exclude measuring the expression of HIST1H2BB. The method may include or exclude measuring the expression of ATP6V1B2. The method may include or exclude measuring the expression of TRAP1.

The method may include or exclude measuring the expression of PFAS. The method may include or exclude measuring the expression of TMEM97. The method may include or exclude measuring the expression of DHCR24. The method may include or exclude measuring the expression of FTH1. The method may include or exclude measuring the expression of HIST1H2AE. The method may include or exclude measuring the expression of NQO1. The method may include or exclude measuring the expression of CD44.

The method may include or exclude measuring the expression of one or more of MCM7, PFAS, HIST1H2AE.

In an additional or alternative embodiment step (c) may comprise or consist of measuring the expression of one or more biomarker listed in Table B. For example, step (c) may comprise or consist of measuring the expression of 2, 3, 4, 5, 6, 7, 8, 9, 10, 11, 12, 13, 14, 15, 16, 17, 18 of the biomarkers listed in Table B. For example, step (c) may comprise or consist of measuring the expression of all of the biomarkers listed in Table B.

In an additional or alternative embodiment step (c) comprises or consists of measuring the expression of at least 2 of the biomarkers listed in Table B, for example, ≥3, ≥24, ≥25, ≥26, ≥27, ≥8, ≥9, ≥10, ≥11, ≥12, ≥13, ≥14, ≥15, ≥16, ≥17, or 18 of the biomarkers listed in Table B.

In an alternative or additional embodiment step (c) comprises or consists of measuring the expression of one or more biomarker listed in Table B(i), for example, ≥2, ≥3, 24, ≥5, ≥6, ≥7, ≥8, ≥9, 10, ≥11, ≥12, ≥13, ≥14, ≥15, or 16 of the biomarkers listed in Table B(i).

In an alternative or additional embodiment step (c) comprises or consists of measuring the expression of one or more biomarker listed in Table B(ii), for example, 2 of the biomarkers listed in Table B(ii).

The method may include or exclude measuring the expression of CCNA2. The method may include or exclude measuring the expression of Transcript ID 8151252. The method may include or exclude measuring the expression of PIGW. The method may include or exclude measuring the expression of SNRPD1. The method may include or exclude measuring the expression of ARHGAP19///ARHGAP19-SLIT1. The method may include or exclude measuring the expression of HIST1H2AB. The method may include or exclude measuring the expression of LRCH2. The method may include or exclude measuring the expression of PKP4///PKP4. The method may include or exclude measuring the expression of RAVER2///RAVER2. The method may include or exclude measuring the expression of DUT///DUT. The method may include or exclude measuring the expression of AURKA. The method may include or exclude measuring the expression of Transcript ID 8055309. The method may include or exclude measuring the expression of NDC1. The method may include or exclude measuring the expression of KIF22///KIF22. The method may include or exclude measuring the expression of OK/SW-CL.58. The method may include or exclude measuring the expression of Transcript ID 7994343. The method may include or exclude measuring the expression of HIST1H2AB///HIST1H2AE. The method may include or exclude measuring the expression of HMGB3.

By "expression" we mean the presence, level and/or amount of the biomarker.

By "biomarker" we include any biological molecule, or component or fragment thereof, the measurement of which can provide information useful in determining sensitizer potency. Thus, in the context of Table A, the biomarker may be a nucleic acid molecule, such as a mRNA or cDNA. Alternatively, the biomarker may be a protein encoded by the nucleic acid molecule or carbohydrate moiety, or an antigenic component or fragment thereof.

In an additional or alternative embodiment the test agent is already known to be, or suspected of being, capable of inducing sensitization of the skin.

For example, the test agent may already be known to be capable of inducing sensitization of the skin by using a method already known in the art, for instance a method described WO 2012/056236 and/or Johansson H et al. The GARD assay for assessment of chemical skin sensitizers. Toxicology in vitro 2013 which are incorporated herein by reference.

In an alternative or additional embodiment, the method is for identifying skin sensitizer potency and skin sensitizer/non-sensitizer status of the test agent (i.e., identifying whether the test agent is a sensitizer or not and identifying its potency as a skin sensitizer). In an alternative or additional embodiment, the method comprises identifying whether the test agent is a sensitizer using the method described in WO 2012/056236 and/or Johansson H et al.

By "skin sensitizing potency" we include or mean the strength of the skin sensitizing ability of an agent. For example, the relative potency or strength of sensitizing ability of an agent might lead to the ordering of a group of test agents from most potent to least potent or vice versa, and/or it might lead to their categorization according to one or more known regulation or system.

In an additional or alternative embodiment the skin sensitization potency determined by the method is categorised according to the European Classification, Labelling and Packaging (CLP) Regulation (EC) 1272/2008 (http://echa.europa.eu/clp-2015). This system is based on the United Nations' Globally Harmonised System (GHS) and from June 2015, the only legislation to apply to the classification and labelling of both substances and mixtures. It requires companies to classify, label and package their products appropriately before placing them on the market. It provides the categories: 1A (strong), 1B (weak), or no cat (no sensitizer).

For example, the method may provide:
(i) one or more agent of potency category 1A;
(ii) one or more agent of potency category 1B; and/or
(iii) one or more agent of potency category no category In an additional or alternative embodiment the skin sensitization potency determined by the method is categorised according to the system described in Basketter et al., 2014, 'Categorization of chemicals according to their relative human skin sensitizing potency,' *Dermatitis*, 25(1):11-21, i.e. categories 1 (strongest sensitizer), 2, 3, 4, 5, or 6 (true non-sensitizer) (e.g. Table 4, FIG. 4).

For example, the method may provide:
(i) one or more agent of potency category 1;
(ii) one or more agent of potency category 2;
(iii) one or more agent of potency category 3;
(iv) one or more agent of potency category 4;
(v) one or more agent of potency category 5; and/or
(vi) one or more agent of potency category 6 (e.g., see present Table 8 and/or Basketter et al., 2014 supra.).

In an additional or alternative embodiment skin sensitization potency is categorised according to the local lymph node assay (LLNA) classification, Guinea pig maximisation test (GPMT) or no observed-effect level (NOEL).

For a detailed description of LLNA see Basketter, D. A., et al., Local lymph node assay—validation, conduct and use in practice. *Food Chem Toxicol,* 2002. 40(5): p. 593-8 which is incorporated herein by reference. For a detailed description of the guinea pig maximization test see Magnusson, B. and A. M. Kligman, *The identification of contact allergens by animal assay. The guinea pig maximization test. J Invest Dermatol,* 1969. 52(3): p. 268-76, which is incorporated herein by reference. For a detailed description of the no observed-effects level (NOEL) test in relation to skin sensitizer potency see Basketter et al., 2005, 'Evaluation of the skin sensitizing potency of chemicals by using the existing methods and considerations of relevance for elicitation' *Contact Dermatitis,* 52(1):39-43; and Griem, P., et al., 2003, 'Proposal for a risk assessment methodology for skin sensitization based on sensitization potency data.' *Regul. Toxicol. Pharmacol.,* 38:269-290 which are incorporated herein by reference. For a correlation between NOEL and potency levels, see also WHO Library Cataloguing-in-Publication Data. Skin sensitization in chemical risk assessment. (IPCS harmonization project document: no. 5), ISBN 978 92 4 156360 4 (in particular, Table 1 on pages 26-28) which is incorporated herein by reference. For a detailed description of CLP, see (http://echa.europa.eu/clp-2015), which is incorporated herein by reference.

In an additional or alternative embodiment the expression of one or more biomarkers measured in step (c) is measured in the cells provided in step (a) prior to and following exposure to the skin sensitizing agent of predetermined potency, and wherein the difference in expression between the one or more biomarkers prior to and following exposure to the test agent is indicative of the potency of the skin sensitizing agent of step (b).

In an additional or alternative embodiment the expression of one or more biomarkers measured in step (c) is measured in the cells provided in step (a) prior to and following exposure to the skin sensitizing agent of predetermined potency, and wherein the difference in expression between the one or more biomarkers prior to and following step (c) is indicative of the potency of the skin sensitizing agent of step (b).

By 'difference in expression' we include that the presence and or amount in a first sample (e.g., a test agent sample) differs from that of a second sample (e.g., a control agent sample). Preferably the presence and/or amount is no more than 40% of that of the comparison sample, for example, no more than 39%, 38%, 37%, 36%, 35%, 34%, 33%, 32%, 31%, 30%, 29%, 28%, 27%, 26%, 25%, 24%, 23%, 22%, 21%, 20%, 19%, 18%, 17%, 16%, 15%, 14%, 13%, 12%, 11%, 10%, 9%, 8%, 7%, 6%, 5%, 4%, 3%, 2%, 1% or 0%.

In an additional or alternative embodiment the one or more biomarker is measured in the cells provided in step (a) prior to and following exposure to the test agent, and wherein the difference in expression between the one or more biomarkers prior to and following exposure to the test agent is indicative of the skin sensitizing potency of the test agent of step (b). Hence, the cells provided in step (a) may provide both the negative control and the test result.

In an additional or alternative embodiment the one or more biomarker is measured in the cells provided in step (a) prior to and following exposure to the test agent, and wherein the difference in expression between the one or more biomarkers prior to and following step (c) is indicative of the skin sensitizing potency of the test agent of step (b). Hence, the cells provided in step (a) may provide both the negative control and the test result.

In an additional or alternative embodiment the method comprises the further steps of:
(d) providing a further population of dendritic cells or a population of dendritic-like cells;
(e) exposing the cells provided in step (d) to:
  i. one or more negative control agent that does not sensitize human skin; and/or
  ii. one or more positive control agent that does sensitize human skin; and/or
  iii. one or more vehicle control;
(f) incubating for the same time and, other than exposure to an agent to the one or more control agent, the same conditions as the cells provided in step (a);
(g) measuring in the cells of step (e) the expression of the two or more biomarkers measured in step (c);
wherein the difference in expression between the two or more biomarkers measured in step (c) and the two or more biomarkers measured in step (e) is indicative of the skin sensitizing potency of the test agent.

In an additional or alternative embodiment the method comprises the further steps of:
(d) providing a further population of dendritic cells or a population of dendritic-like cells;
(e) exposing the cells provided in step (d) to:
  i. a negative control agent that does not sensitize human skin;
  ii. a vehicle control; or
  iii. incubation for the same time and, other than exposure to an agent of predetermined skin sensitization potency, the same conditions as the cells provided in step (a);
(f) measuring in the cells of step (e) the expression of the two or more biomarkers measured in step (c);
wherein the difference in expression between the two or more biomarkers measured in step (c) and the two or more biomarkers measured in step (e) is indicative of the skin sensitizing potency of the test agent.

In an additional or alternative embodiment the vehicle control comprises DMSO.

By 'difference in expression' we include that the presence and or amount in a first sample (e.g., a test agent sample) differs from that of a second sample (e.g., a control agent sample). Preferably the presence and/or amount is no more than 40% of that of the comparison sample, for example, no more than 39%, 38%, 37%, 36%, 35%, 34%, 33%, 32%, 31%, 30%, 29%, 28%, 27%, 26%, 25%, 24%, 23%, 22%, 21%, 20%, 19%, 18%, 17%, 16%, 15%, 14%, 13%, 12%, 11%, 10%, 9%, 8%, 7%, 6%, 5%, 4%, 3%, 2%, 1% or 0%.

In an additional or alternative embodiment the method comprises the further steps of:
(h) providing a further population of dendritic cells or a population of dendritic-like cells;
(i) exposing the cells provided in step (h) to a skin sensitizing agent of predetermined potency;

(j) measuring in the cells of step (i) the expression of the two or more biomarkers measured in step (c);

wherein the correspondence in expression between the two or more biomarkers measured in step (c) and the two or more biomarkers measured in step ( ) is indicative of the skin sensitizing potency of the test agent.

By 'correspondence in expression' we include that that the presence and or amount in a first sample (e.g., a test agent sample) is similar or identical to the presence and/or amount in a second sample (e.g., a control sample). Preferably the presence and/or amount is at least 60% of that of the control sample, for example, at least 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or 100%.

In an additional or alternative embodiment the method comprises the further step of:
(k) identifying the skin sensitizing potency of the test agent.

The identification may be performed using any suitable statistical method or machine learning algorithm known in the art, such as Random Forest (RF), Support Vector Machine (SVM), Principal Component Analysis (PCA), ordinary least squares (OLS), partial least squares regression (PLS), orthogonal partial least squares regression (O-PLS) and other multivariate statistical analyses (e.g., backward stepwise logistic regression model). For a review of multivariate statistical analysis see, for example, Schervish, Mark J. (November 1987). "A Review of Multivariate Analysis". *Statistical Science* 2 (4): 396-413 which is incorporated herein by reference. Preferably a Random Forest model is used (such as is described in detail in Example A).

In an additional or alternative embodiment of the methods of the invention, sensitizing potency is determined with an ROC AUC of at least 0.45, for example with an ROC AUC of at least, 0.50, 0.55, 0.60, 0.65, 0.70, 0.75, 0.80, 0.85, 0.86, 0.87, 0.88, 0.89, 0.90, 0.91, 0.92, 0.93, 0.94, 0.95, 0.96, 0.97, 0.98, 0.99 or with an ROC AUC of 1.00. Preferably, skin sensitizing potency is determined with an ROC AUC of at least 0.80, more preferably at least 0.85, still more preferably at least 0.88.

Preferably, the methods of the invention have an accuracy of at least 60%, for example, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or 100% accuracy.

Preferably, the methods of the invention have a sensitivity of at least 60%, for example, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or 100% sensitivity.

Preferably, the methods of the invention have a specificity of at least 60%, for example, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or 100% specificity.

By "accuracy" we mean the proportion of correct outcomes of a method, by "sensitivity" we mean the proportion of all positive chemicals that are correctly classified as positives, and by "specificity" we mean the proportion of all negative chemicals that are correctly classified as negatives.

In an additional or alternative embodiment the method comprises the further step of:

(l) one or more repetition of steps (h) to (j) (and where present, step (k)).

In an additional or alternative embodiment, each repetition of steps (a) to (c) (and where present, steps (d)-(f/g)) is performed concurrently (i.e., with original steps (a) to (c) (and where present, steps (d)-(f/g))). In an additional or alternative embodiment, each repetition of steps (a) to (c) (and where present, steps (d)-(f/g)) is performed consecutively.

In an additional or alternative embodiment step (j) comprises or consists of one or more repetition wherein:
(I) the same agent of predetermined skin sensitization potency as provided in step (i) for one or more other repetition; or
(II) a different agent of predetermined skin sensitization potency as provided in step (i) for one or more other repetition.

In an additional or alternative embodiment the different agent of predetermined skin sensitization potency provided in step (i) is selected from the group consisting of:
(I) an agent of the same sensitization potency as the different agent of predetermined skin sensitization potency provided in step (i); or
(II) an agent of a different sensitization potency from the different agent of predetermined skin sensitization potency provided in step (i).

In an additional or alternative embodiment steps (a) to (c) (and where present, step (f/g)) are repeated at least once, for example, ≥2, ≥3, ≥4, ≥5, ≥6, ≥7, ≥8, ≥9, ≥10, ≥11, ≥12, ≥13, ≥14, ≥15, ≥16, ≥17, ≥18, ≥19, ≥20, ≥21, ≥22, ≥23, ≥24, ≥25, ≥26, ≥27, ≥28, ≥29, ≥30, ≥40, ≥50, ≥60, ≥70, ≥80, ≥90, ≥100, ≥150, ≥200, ≥250, ≥300, ≥350, ≥400, ≥450, ≥500, ≥600, ≥700, ≥800, ≥900 or ≥1000 repetitions.

In an additional or alternative embodiment each step or repetition of steps may be repeated identically to control for experimental error, for example, 2, 3, 4, 5, 6, 7, 8, 9 or 10 repeats.

In an additional or alternative embodiment the expression of the two or more biomarkers measured is measured for agents of predetermined skin sensitization potency over the full range of skin sensitization potencies.

By 'full range of skin sensitization potencies' we include assessing sensitizers of the highest and lowest degree of skin sensitizer category in the categorisation system being used.

Preferably, sensitizers are assessed at each sensitizer category in the categorisation system being used.

In an additional or alternative embodiment the skin sensitizing agent of predetermined potency comprises or consist of one or more agents selected from the group consisting of the group defined in Table 2. For example, the method may comprise measuring ≥2, ≥3, ≥4, ≥5, ≥6, ≥7, ≥8, ≥9, ≥10, or 11, of the agents defined in Table 2.

In an additional or alternative embodiment the skin sensitizing agent of predetermined potency comprises or consist of agents selected from the group consisting of the group defined in Table 8, Table 9 and/or Table 8, e.g., Table 8 only, Table 9 only, Table 10 only, Tables 8 and 9, Tables 8 and 10, Tables 9 and 10 or Tables 8, 9 and 10. For Example, the method may comprise measuring ≥2, ≥3, ≥4, ≥5, ≥6, ≥7, ≥8, ≥9, ≥10, 11, ≥12, ≥13, ≥14, ≥15, ≥16, ≥17, ≥18, ≥19, ≥20, ≥21, ≥22, ≥23, ≥24, ≥25, ≥26, ≥27, ≥28, ≥29, ≥30, ≥31, ≥32, ≥33, ≥34, ≥35, ≥36, ≥≥37, ≥38, ≥39, ≥40, ≥41, ≥42, ≥43, ≥44, ≥45, ≥46, ≥47, ≥48, ≥49, ≥50, ≥51, ≥52, ≥53, ≥54, ≥55, ≥56, ≥57, ≥58, ≥59, ≥60, ≥61, ≥62, ≥63, ≥64, ≥65, ≥66, ≥67, ≥68, ≥69, ≥70, ≥71, ≥72, ≥73, ≥74, ≥≥75, ≥76, ≥77, ≥78, ≥79, ≥80, ≥81, ≥82, ≥283, ≥84, ≥85, ≥86, ≥87, ≥88, ≥89, ≥90, ≥91, ≥92, ≥93, ≥≥94, ≥95, ≥96, ≥97, ≥98, ≥99, ≥100, ≥101, ≥102, ≥103, ≥104, ≥105, ≥106, ≥107, ≥108, ≥109, ≥110, ≥111, ≥112, ≥113, ≥114, ≥115, ≥116, ≥117, ≥118, ≥119, ≥120, ≥121 or 122 of the control agents defined in Tables 8, 9 and 10.

In an additional or alternative embodiment the skin sensitizing agent of predetermined potency comprises or consist of agents selected from the group consisting of 1-Butanol, 4-Aminobenzoic acid, Benzaldehyde, Chlorobenzene, Diethyl phthalate, Dimethyl formamide, Ethyl vanillin, Glycerol, Isopropanol, Lactic acid, Methyl salicylate, Octanoic acid, Propylene glycol, Phenol, p-hydroxybenzoic acid, Potassium permanganate, Salicylic acid, Sodium dodecyl sulphate, Tween 80, Zinc sulphate, 2,4-Dinitrochlorobenzene, Oxazolone, Potassium dichromate, Kathon CG (MC/MCI), Formaldehyde, 2-Aminophenol, 2-nitro-1,4-Phenylendiamine, p-Phenylendiamine, Hexylcinnamic aldehyde, 2-Hydroxyethyl acrylate, 2-Mercaptobenzothiazole, Glyoxal, Cinnamaldehyde, Isoeugenol, Ethylendiamine, Resorcinol, Cinnamic alcohol, Eugenol, Penicillin G, Geraniol and DMSO.

In a preferred embodiment, step (c) comprises or consists of measuring the expression of a nucleic acid molecule of one or more of the biomarkers. The nucleic acid molecule may be a cDNA molecule or an mRNA molecule. Preferably, the nucleic acid molecule is an mRNA molecule. However, the nucleic acid molecule may be a cDNA molecule.

In one embodiment the measurement of the expression of one or more of the biomarkers in step (c) is performed using a method selected from the group consisting of Southern hybridisation, Northern hybridisation, polymerase chain reaction (PCR), reverse transcriptase PCR (RT-PCR), quantitative real-time PCR (qRT-PCR), nanoarray, microarray, macroarray, autoradiography and in situ hybridisation. Preferably, the expression of one or more biomarker(s) is measured using a DNA microarray.

In an additional or alternative embodiment the one or more biomarkers measured in step (c) is measured using an array (e.g., a DNA array). In an additional or alternative embodiment the one or more biomarkers measured in step (c) is measured using a whole genome array (e.g., the Affymetrix Human Gene 1.0 ST array or Affymetrix Human Gene 2.0 ST array). In an alternative or additional embodiment, the Nanostring nCounter system is used (e.g., custom Nanostring nCounter code sets based on selection from a whole genome array (e.g., Affymetrix Human Gene 1.0 ST array or Affymetrix Human Gene 2.0 ST array).

The method may comprise measuring the expression of one or more biomarkers in step (c) using one or more binding moieties, each capable of binding selectively to a nucleic acid molecule encoding one of the biomarkers identified in Table A.

In one embodiment the one or more binding moieties each comprise or consist of a nucleic acid molecule. In a further embodiment the one or more binding moieties each comprise or consist of DNA, RNA, PNA, LNA, GNA, TNA or PMO. Preferably, the one or more binding moieties each comprise or consist of DNA. In one embodiment, the one or more binding moieties are 5 to 100 nucleotides in length. However, in an alternative embodiment, they are 15 to 35 nucleotides in length.

The one or more binding moieties may comprise or consist of one or more probe from the Human Gene 1.0 ST Array (Affymetrix, Santa Clara, Calif., USA). Probe identification numbers are provided in Table A herein, where they are referred to as "transcript cluster IDs".

Suitable binding agents (also referred to as binding molecules or binding moieties) may be selected or screened from a library based on their ability to bind a given nucleic acid, protein or amino acid motif, as discussed below.

In a preferred embodiment, the binding moiety comprises a detectable moiety.

By a "detectable moiety" we include a moiety which permits its presence and/or relative amount and/or location (for example, the location on an array) to be determined, either directly or indirectly.

Suitable detectable moieties are well known in the art.

For example, the detectable moiety may be a fluorescent and/or luminescent and/or chemiluminescent moiety which, when exposed to specific conditions, may be detected. Such a fluorescent moiety may need to be exposed to radiation (i.e. light) at a specific wavelength and intensity to cause excitation of the fluorescent moiety, thereby enabling it to emit detectable fluorescence at a specific wavelength that may be detected.

Alternatively, the detectable moiety may be an enzyme which is capable of converting a (preferably undetectable) substrate into a detectable product that can be visualised and/or detected. Examples of suitable enzymes are discussed in more detail below in relation to, for example, ELISA assays.

Hence, the detectable moiety may be selected from the group consisting of: a fluorescent moiety; a luminescent moiety; a chemiluminescent moiety; a radioactive moiety (for example, a radioactive atom); or an enzymatic moiety. Preferably, the detectable moiety comprises or consists of a radioactive atom. The radioactive atom may be selected from the group consisting of technetium-99m, iodine-123, iodine-125, iodine-131, indium-111, fluorine-19, carbon-13, nitrogen-15, oxygen-17, phosphorus-32, sulphur-35, deuterium, tritium, rhenium-186, rhenium-188 and yttrium-90.

Clearly, the agent to be detected (such as, for example, the one or more biomarkers in the test sample and/or control sample described herein and/or an antibody molecule for use in detecting a selected protein) must have sufficient of the appropriate atomic isotopes in order for the detectable moiety to be readily detectable.

In an alternative preferred embodiment, the detectable moiety of the binding moiety is a fluorescent moiety.

The radio- or other labels may be incorporated into the biomarkers present in the samples of the methods of the invention and/or the binding moieties of the invention in known ways. For example, if the binding agent is a polypeptide it may be biosynthesised or may be synthesised by chemical amino acid synthesis using suitable amino acid precursors involving, for example, fluorine-19 in place of hydrogen. Labels such as $^{99m}$Tc, $^{123}$I, $^{186}$Rh, $^{188}$Rh and $^{111}$In can, for example, be attached via cysteine residues in the binding moiety. Yttrium-90 can be attached via a lysine residue. The IODOGEN method (Fraker et al (1978) *Biochem. Biophys. Res. Comm.* 80, 49-57) can be used to incorporate $^{123}$I. Reference ("Monoclonal Antibodies in Immunoscintigraphy", J-F Chatal, CRC Press, 1989) describes other methods in detail. Methods for conjugating other detectable moieties (such as enzymatic, fluorescent, luminescent, chemiluminescent or radioactive moieties) to proteins are well known in the art.

It will be appreciated by persons skilled in the art that biomarkers in the sample(s) to be tested may be labelled with a moiety which indirectly assists with determining the presence, amount and/or location of said proteins. Thus, the moiety may constitute one component of a multicomponent detectable moiety. For example, the biomarkers in the sample(s) to be tested may be labelled with biotin, which allows their subsequent detection using streptavidin fused or otherwise joined to a detectable label.

The method provided in the first aspect of the present invention may comprise or consist of, in step (c), determining the expression of the protein of one or more biomarker defined in Table A. The method may comprise measuring the expression of one or more biomarkers in step (c) using one or more binding moieties each capable of binding selectively to one of the biomarkers identified in Table A. The one or more binding moieties may comprise or consist of an antibody or an antigen-binding fragment thereof such as a monoclonal antibody or fragment thereof.

The term "antibody" includes any synthetic antibodies, recombinant antibodies or antibody hybrids, such as but not limited to, a single-chain antibody molecule produced by phage-display of immunoglobulin light and/or heavy chain variable and/or constant regions, or other immunointeractive molecules capable of binding to an antigen in an immunoassay format that is known to those skilled in the art.

We also include the use of antibody-like binding agents, such as affibodies and aptamers.

A general review of the techniques involved in the synthesis of antibody fragments which retain their specific binding sites is to be found in Winter & Milstein (1991) *Nature* 349, 293-299.

Additionally, or alternatively, one or more of the first binding molecules may be an aptamer (see Collett et al., 2005, *Methods* 37:4-15).

Molecular libraries such as antibody libraries (Clackson et al, 1991, *Nature* 352, 624-628; Marks et al, 1991, *J Mol Biol* 222(3): 581-97), peptide libraries (Smith, 1985, *Science* 228(4705): 1315-7), expressed cDNA libraries (Santi et al (2000) *J Mol Biol* 296(2): 497-508), libraries on other scaffolds than the antibody framework such as affibodies (Gunneriusson et al, 1999, *App/Environ Microbiol* 65(9): 4134-40) or libraries based on aptamers (Kenan et al, 1999, *Methods Mol Biol* 118, 217-31) may be used as a source from which binding molecules that are specific for a given motif are selected for use in the methods of the invention.

The molecular libraries may be expressed in vivo in prokaryotic cells (Clackson et al, 1991, op. cit.; Marks et al, 1991, op. cit.) or eukaryotic cells (Kieke et al, 1999, *Proc Natl Acad Sci USA*, 96(10):5651-6) or may be expressed in vitro without involvement of cells (Hanes & Pluckthun, 1997, *Proc Natl Acad Sci USA* 94(10):4937-42; He & Taussig, 1997, *Nucleic Acids Res* 25(24):5132-4; Nemoto et al, 1997, *FEBS Lett*, 414(2):405-8).

In cases when protein based libraries are used, the genes encoding the libraries of potential binding molecules are often packaged in viruses and the potential binding molecule displayed at the surface of the virus (Clackson et al, 1991, supra; Marks et al, 1991, supra; Smith, 1985, supra).

Perhaps the most commonly used display system is filamentous bacteriophage displaying antibody fragments at their surfaces, the antibody fragments being expressed as a fusion to the minor coat protein of the bacteriophage (Clackson et al, 1991, supra; Marks et al, 1991, supra). However, other suitable systems for display include using other viruses (EP 39578), bacteria (Gunneriusson et at, 1999, supra; Daugherty et al, 1998, *Protein Eng* 11(9):825-32; Daugherty et al, 1999, *Protein Eng* 12(7):613-21), and yeast (Shusta et a, 1999, *J Mol Biol* 292(5):949-56).

In addition, display systems have been developed utilising linkage of the polypeptide product to its encoding mRNA in so-called ribosome display systems (Hanes & Pluckthun, 1997, supra; He & Taussig, 1997, supra; Nemoto et al, 1997, supra), or alternatively linkage of the polypeptide product to the encoding DNA (see U.S. Pat. No. 5,856,090 and WO 98/37186).

The variable heavy ($V_H$) and variable light ($V_L$) domains of the antibody are involved in antigen recognition, a fact first recognised by early protease digestion experiments. Further confirmation was found by "humanisation" of rodent antibodies. Variable domains of rodent origin may be fused to constant domains of human origin such that the resultant antibody retains the antigenic specificity of the rodent parented antibody (Morrison et al (1984) *Proc. Natl. Acad. Sci. USA* 81, 6851-6855).

That antigenic specificity is conferred by variable domains and is independent of the constant domains is known from experiments involving the bacterial expression of antibody fragments, all containing one or more variable domains. These molecules include Fab-like molecules (Better et al (1988) *Science* 240, 1041); Fv molecules (Skerra et al (1988) *Science* 240, 1038); single-chain Fv (ScFv) molecules where the $V_H$ and $V_L$ partner domains are linked via a flexible oligopeptide (Bird et al (1988) Science 242, 423; Huston et al (1988) *Proc. Natl. Acad. Sci. USA* 85, 5879) and single domain antibodies (dAbs) comprising isolated V domains (Ward et al (1989) *Nature* 341, 544). A general review of the techniques involved in the synthesis of antibody fragments which retain their specific binding sites is to be found in Winter & Milstein (1991) *Nature* 349, 293-299.

The antibody or antigen-binding fragment may be selected from the group consisting of intact antibodies, Fv fragments (e.g. single chain Fv and disulphide-bonded Fv), Fab-like fragments (e.g. Fab fragments, Fab' fragments and F(ab)$_2$ fragments), single variable domains (e.g. $V_H$ and $V_L$ domains) and domain antibodies (dAbs, including single and dual formats [i.e. dAb-linker-dAb]). Preferably, the antibody or antigen-binding fragment is a single chain Fv (scFv).

The one or more binding moieties may alternatively comprise or consist of an antibody-like binding agent, for example an affibody or aptamer.

By "scFv molecules" we mean molecules wherein the $V_H$ and $V_L$ partner domains are linked via a flexible oligopeptide.

The advantages of using antibody fragments, rather than whole antibodies, are several-fold. The smaller size of the fragments may lead to improved pharmacological properties, such as better penetration of solid tissue. Effector functions of whole antibodies, such as complement binding, are removed. Fab, Fv, ScFv and dAb antibody fragments can all be expressed in and secreted from *E. coli*, thus allowing the facile production of large amounts of the said fragments.

Whole antibodies, and F(ab')$_2$ fragments are "bivalent". By "bivalent" we mean that the said antibodies and F(ab')$_2$ fragments have two antigen combining sites. In contrast, Fab, Fv, ScFv and dAb fragments are monovalent, having only one antigen combining sites.

The antibodies may be monoclonal or polyclonal. Suitable monoclonal antibodies may be prepared by known techniques, for example those disclosed in "Monoclonal Antibodies: A manual of techniques", H Zola (CRC Press, 1988) and in "Monoclonal Hybridoma Antibodies: Techniques and applications", J G R Hurrell (CRC Press, 1982), both of which are incorporated herein by reference.

When potential binding molecules are selected from libraries, one or more selector peptides having defined motifs are usually employed. Amino acid residues that provide structure, decreasing flexibility in the peptide or charged, polar or hydrophobic side chains allowing interaction with the binding molecule may be used in the design of motifs for selector peptides. For example:
(i) Proline may stabilise a peptide structure as its side chain is bound both to the alpha carbon as well as the nitrogen;
(ii) Phenylalanine, tyrosine and tryptophan have aromatic side chains and are highly hydrophobic, whereas leucine and isoleucine have aliphatic side chains and are also hydrophobic;
(iii) Lysine, arginine and histidine have basic side chains and will be positively charged at neutral pH, whereas aspartate and glutamate have acidic side chains and will be negatively charged at neutral pH;
(iv) Asparagine and glutamine are neutral at neutral pH but contain a amide group which may participate in hydrogen bonds;
(v) Serine, threonine and tyrosine side chains contain hydroxyl groups, which may participate in hydrogen bonds.

Typically, selection of binding molecules may involve the use of array technologies and systems to analyse binding to spots corresponding to types of binding molecules.

The one or more protein-binding moieties may comprise a detectable moiety. The detectable moiety may be selected from the group consisting of a fluorescent moiety, a luminescent moiety, a chemiluminescent moiety, a radioactive moiety and an enzymatic moiety.

In a further embodiment of the methods of the invention, step (c) may be performed using an assay comprising a second binding agent capable of binding to the one or more proteins, the second binding agent also comprising a detectable moiety. Suitable second binding agents are described in detail above in relation to the first binding agents.

Thus, the proteins of interest in the sample to be tested may first be isolated and/or immobilised using the first binding agent, after which the presence and/or relative amount of said biomarkers may be determined using a second binding agent.

In one embodiment, the second binding agent is an antibody or antigen-binding fragment thereof; typically a recombinant antibody or fragment thereof. Conveniently, the antibody or fragment thereof is selected from the group consisting of: scFv; Fab; a binding domain of an immunoglobulin molecule. Suitable antibodies and fragments, and methods for making the same, are described in detail above.

Alternatively, the second binding agent may be an antibody-like binding agent, such as an affibody or aptamer.

Alternatively, where the detectable moiety on the protein in the sample to be tested comprises or consists of a member of a specific binding pair (e.g. biotin), the second binding agent may comprise or consist of the complimentary member of the specific binding pair (e.g. streptavidin).

Where a detection assay is used, it is preferred that the detectable moiety is selected from the group consisting of: a fluorescent moiety; a luminescent moiety; a chemiluminescent moiety; a radioactive moiety; an enzymatic moiety. Examples of suitable detectable moieties for use in the methods of the invention are described above.

Preferred assays for detecting serum or plasma proteins include enzyme linked immunosorbent assays (ELISA), radioimmunoassay (RIA), immunoradiometric assays (IRMA) and immunoenzymatic assays (IEMA), including sandwich assays using monoclonal and/or polyclonal antibodies. Exemplary sandwich assays are described by David et al in U.S. Pat. Nos. 4,376,110 and 4,486,530, hereby incorporated by reference. Antibody staining of cells on slides may be used in methods well known in cytology laboratory diagnostic tests, as well known to those skilled in the art.

Thus, in one embodiment the assay is an ELISA (Enzyme Linked Immunosorbent Assay) which typically involves the use of enzymes which give a coloured reaction product, usually in solid phase assays. Enzymes such as horseradish peroxidase and phosphatase have been widely employed. A way of amplifying the phosphatase reaction is to use NADP as a substrate to generate NAD which now acts as a coenzyme for a second enzyme system. Pyrophosphatase from *Escherichia coli* provides a good conjugate because the enzyme is not present in tissues, is stable and gives a good reaction colour. Chemiluminescent systems based on enzymes such as luciferase can also be used.

Conjugation with the vitamin biotin is frequently used since this can readily be detected by its reaction with enzyme-linked avidin or streptavidin to which it binds with great specificity and affinity.

In an alternative embodiment, the assay used for protein detection is conveniently a fluorometric assay. Thus, the detectable moiety of the second binding agent may be a fluorescent moiety, such as an Alexa fluorophore (for example Alexa-647).

Preferably, steps (c), (g), (f) and/or (j) of the methods described in the first aspect are performed using an array. The array may be a bead-based array or a surface-based array. The array may be selected from the group consisting of: macroarray; microarray; nanoarray.

Arrays per se are well known in the art. Typically they are formed of a linear or two-dimensional structure having spaced apart (i.e. discrete) regions ("spots"), each having a finite area, formed on the surface of a solid support. An array can also be a bead structure where each bead can be identified by a molecular code or colour code or identified in a continuous flow. Analysis can also be performed sequentially where the sample is passed over a series of spots each adsorbing the class of molecules from the solution. The solid support is typically glass or a polymer, the most commonly used polymers being cellulose, polyacrylamide, nylon, polystyrene, polyvinyl chloride or polypropylene. The solid supports may be in the form of tubes, beads, discs, silicon chips, microplates, polyvinylidene difluoride (PVDF) membrane, nitrocellulose membrane, nylon membrane, other porous membrane, non-porous membrane (e.g. plastic, polymer, perspex, silicon, amongst others), a plurality of polymeric pins, or a plurality of microtitre wells, or any other surface suitable for immobilising proteins, polynucleotides and other suitable molecules and/or conducting an immunoassay. The binding processes are well known in the art and generally consist of cross-linking covalently binding or physically adsorbing a protein molecule, polynucleotide or the like to the solid support. Alternatively, affinity coupling of the probes via affinity-tags or similar constructs may be employed. By using well-known techniques, such as contact or non-contact printing, masking or photolithography, the location of each spot can be defined. For reviews see Jenkins, R. E., Pennington, S. R. (2001, *Proteomics*, 2, 13-29) and Lal et al (2002, *Drug Discov Today* 15; 7(18 Suppl):S143-9).

Typically the array is a microarray. By "microarray" we include the meaning of an array of regions having a density of discrete regions of at least about 100/cm$^2$, and preferably at least about 1000/cm$^2$. The regions in a microarray have typical dimensions, e.g. diameter, in the range of between about 10-250 m, and are separated from other regions in the array by about the same distance. The array may alternatively be a macroarray or a nanoarray.

Once suitable binding molecules (discussed above) have been identified and isolated, the skilled person can manufacture an array using methods well known in the art of molecular biology.

In an additional or alternative embodiment one or more biomarkers measured in step (c) comprise or consist of one or more homologous gene product expressed by human cells. In an additional or alternative embodiment one or more biomarkers measured in step (c) is a protein or polypeptide. In an additional or alternative embodiment one or more biomarker measured in step (c) is a nucleic acid (e.g., DNA, mRNA or cDNA etc.).

In an additional or alternative embodiment method is performed in vitro, in vivo, ex vivo or in silico. For example, the method may in particular be performed in vitro.

In an additional or alternative embodiment the skin sensitization is a hypersensitivity response (e.g., a cell-mediated hypersensitivity response). In an additional or alternative embodiment the hypersensitivity response is a type IV hypersensitivity response. In an additional or alternative embodiment the hypersensitivity response is allergic contact dermatitis (ACD).

By 'test agent' we include any chemical entity (or mixture of chemical entities) for which sensitization potency and/or sensitization status is to be determined.

By "sensitization status" we include or mean whether or not a chemical entity (or mixture of chemical entities) is a sensitizer or not (e.g., a skin sensitizer and/or a respiratory sensitizer).

By "skin sensitizing agent" we mean any agent capable of inducing and triggering a Type IV delayed-type hypersensitivity reaction in a mammal. Preferably, the Type IV delayed-type hypersensitivity reaction is DC-mediated.

In one embodiment, the one or more "skin sensitizing agent" is an agent capable of inducing and triggering a Type IV delayed-type hypersensitivity reaction at a site of epidermal contact in a mammal.

The mammal may be any domestic or farm animal. Preferably, the mammal is a rat, mouse, guinea pig, cat, dog, horse or a primate. Most preferably, the mammal is human. As discussed above, in vivo methods of determining sensitisation are known in the art. A preferred method is the Local lymph node assay (for details, see Basketter, D. A., et al., *Local lymph node assay—validation, conduct and use in practice*. Food Chem Toxicol, 2002. 40(5): p. 593-8). A further suitable, but less preferred, method is the guinea pig maximization test (for details, see Magnusson, B. and A. M. Kligman, *The identification of contact allergens by animal assay. The guinea pig maximization test*. J Invest Dermatol, 1969. 52(3): p. 268-76).

In an additional or alternative embodiment the population of dendritic cells or population of dendritic-like cells is a population of dendritic-like cells. In an additional or alternative embodiment the dendritic-like cells are myeloid dendritic-like cells. In an additional or alternative embodiment the myeloid dendritic-like cells are derived from myeloid dendritic cells. In an additional or alternative embodiment the cells derived from myeloid dendritic cells are myeloid leukaemia-derived cells. In an additional or alternative embodiment the myeloid leukaemia-derived cells are selected from the group consisting of KG-1, THP-1, U-937, HL-60, Monomac-6, AML-193 and MUTZ-3. In an additional or alternative embodiment the dendritic-like cells are MUTZ-3 cells. MUTZ-3 cells are human acute myelomonocytic leukemia cells that are available from Deutsche Sammlung für Mikroorganismen und Zellkulturen GmbH (DSMZ), Braunschweig, Germany (www.dsmz.de; DMSZ No. ACC 295).

By "dendritic-like cells" we mean non-dendritic cells that exhibit functional and phenotypic characteristics specific to dendritic cells such as morphological characteristics, expression of costimulatory molecules and MHC class II molecules, and the ability to pinocytose macromolecules and to activate resting T cells.

In one embodiment, the dendritic-like cells, after stimulation with cytokine, present antigens through CD1d, MHC class I and II and/or induce specific T-cell proliferation.

In one embodiment, the dendritic-like cells are CD34$^+$ dendritic cell progenitors. Optionally, the CD34$^+$ dendritic cell progenitors can acquire, upon cytokine stimulation, the phenotypes of presenting antigens through CD1d, MHC class I and II, induce specific T-cell proliferation, and/or displaying a mature transcriptional and phenotypic profile upon stimulation with inflammatory mediators (i.e. similar phenotypes to immature dendritic cells or Langerhans-like dendritic cells).

In one embodiment, the population of dendritic cells or population of dendritic-like cells is a population of dendritic cells. Preferably, the dendritic cells are primary dendritic cells. Preferably, the dendritic cells are myeloid dendritic cells.

Dendritic cells may be recognized by function, by phenotype and/or by gene expression pattern, particularly by cell surface phenotype. These cells are characterized by their distinctive morphology, high levels of surface MHC-class II expression and ability to present antigen to CD4+ and/or CD8+ T cells, particularly to naïve T cells (Steinman et al. (1991) Ann. Rev. Immunol. 9: 271).

The cell surface of dendritic cells is unusual, with characteristic veil-like projections, and is characterized by expression of the cell surface markers CD11c and MHC class II. Most DCs are negative for markers of other leukocyte lineages, including T cells, B cells, monocytes/macrophages, and granulocytes. Subpopulations of dendritic cells may also express additional markers including 33D1, CCR1, CCR2, CCR4, CCR5, CCR6, CCR7, CD1a-d, CD4, CD5, CD8alpha, CD9, CD11b, CD24, CD40, CD48, CD54, CD58, CD80, CD83, CD86, CD91, CD117, CD123 (IL3Ra), CD134, CD137, CD150, CD153, CD162, CXCR1, CXCR2, CXCR4, DCIR, DC-LAMP, DC-SIGN, DEC205, E-cadherin, Langerin, Mannose receptor, MARCO, TLR2, TLR3 TLR4, TLR5, TLR6, TLR9, and several lectins.

The patterns of expression of these cell surface markers may vary along with the maturity of the dendritic cells, their tissue of origin, and/or their species of origin. Immature dendritic cells express low levels of MHC class II, but are capable of endocytosing antigenic proteins and processing them for presentation in a complex with MHC class II molecules. Activated dendritic cells express high levels of MHC class 11, ICAM-1 and CD86, and are capable of stimulating the proliferation of naive allogeneic T cells, e.g. in a mixed leukocyte reaction (MLR).

Functionally, dendritic cells or dendritic-like cells may be identified by any convenient assay for determination of antigen presentation. Such assays may include testing the ability to stimulate antigen-primed and/or naive T cells by presentation of a test antigen, followed by determination of T cell proliferation, release of IL-2, and the like.

Methods of detecting and/or measuring the concentration of protein and/or nucleic acid are well known to those skilled in the art, see for example Sambrook and Russell, 2001, Cold Spring Harbor Laboratory Press.

Preferred methods for detection and/or measurement of protein include Western blot, North-Western blot, immunosorbent assays (ELISA), antibody microarray, tissue microarray (TMA), immunoprecipitation, in situ hybridisation and other immunohistochemistry techniques, radioimmunoassay (RIA), immunoradiometric assays (IRMA) and immunoenzymatic assays (IEMA), including sandwich assays using monoclonal and/or polyclonal antibodies. Exemplary sandwich assays are described by David et al., in U.S. Pat. Nos. 4,376,110 and 4,486,530, hereby incorporated by reference. Antibody staining of cells on slides may be used in methods well known in cytology laboratory diagnostic tests, as well known to those skilled in the art.

Typically, ELISA involves the use of enzymes which give a coloured reaction product, usually in solid phase assays. Enzymes such as horseradish peroxidase and phosphatase have been widely employed. A way of amplifying the phosphatase reaction is to use NADP as a substrate to generate NAD which now acts as a coenzyme for a second enzyme system.

Pyrophosphatase from *Escherichia coli* provides a good conjugate because the enzyme is not present in tissues, is stable and gives a good reaction colour. Chemi-luminescent systems based on enzymes such as luciferase can also be used.

Conjugation with the vitamin biotin is frequently used since this can readily be detected by its reaction with enzyme-linked avidin or streptavidin to which it binds with great specificity and affinity.

A second aspect of the invention provides an array for use in the method according to the first aspect of the invention, the array comprising one or more binding moiety as defined in the first aspect of the invention.

In an additional or alternative embodiment the array comprises one or more binding moiety for each of the biomarkers as defined in the first aspect of the invention.

In an additional or alternative embodiment the one or more binding moiety is immobilised.

In an additional or alternative embodiment the array is a bead-based array. In an additional or alternative embodiment the array is a surface-based array.

In an additional or alternative embodiment the array is selected from the group consisting of: macroarray; microarray; nanoarray.

The array of the second aspect of the invention may comprise one or more, preferably two or more, binding moieties, wherein the binding moieties are each capable of binding selectively to a biomarker as defined in the first aspect. Therefore, the array may comprise or consist of a particular selection of biomarker-specific binding moieties which correlates to any particular selection of biomarkers as defined in the first aspect.

A third aspect of the invention provides the use of two or more biomarkers as defined in the first aspect of the invention for determining the skin sensitizing potency of an agent.

In an additional or alternative embodiment there is provided the use of a biomarker selected from the group defined in Table A for determining the skin sensitizing potency of an agent, preferably wherein the biomarker is selected from the group defined in Table A(i) and/or Table A(ii).

In an additional or alternative embodiment there is provided the use of a binding moiety with specificity for a biomarker selected from the group defined in Table A for determining the skin sensitizing potency of an agent, preferably wherein the binding moiety has specificity for a biomarker selected from the group defined in Table A(i) and/or Table A(ii).

A fourth aspect of the invention provides an analytical kit for use in a method according the first aspect of the invention comprising:
  (a) an array according to the second aspect of the invention; and
  (b) instructions for performing the method as defined in the first aspect of the invention (optional).

In an additional or alternative embodiment the analytical kit further comprising one or more control agents as defined in the first aspect of the invention.

A fifth aspect of the invention provides a method of treating or preventing a type 1 hypersensitivity reaction (such as ACD) in a patient comprising the steps of:
  (a) providing one or more test agent that the patient is or has been exposed to;
  (b) determining whether the one or more test agent provided in step (a) is a skin sensitizer and/or its potency as a sensitizer using a method of the present invention; and
  (c) where one or more test agent is identified as a skin sensitizer and/or a skin sensitizer of a particular potency, reducing or preventing exposure of the patient to the one or more test agent and/or providing appropriate treatment for the symptoms of sensitization.

Preferably, the one or more test agent that the patient is or has been exposed to is an agent that the patient is presently exposed to at least once a month, for example, at least once every two weeks, at least once every week, or at least once every day.

Treatments of the symptoms of sensitization may include, for example, topical steroids.

Preferably, the method of treatment is consistent with the method described in the first aspect of the invention, and one or more of the embodiments described therein.

A sixth aspect of the invention provides a computer program for operating the methods the invention, for example, for interpreting the expression data of step (c) (and subsequent expression measurement steps) and thereby determining whether one or more test agent is a respiratory sensitizer and/or the sensitizer potency of the one or more test agent. The computer program may be a programmed SVM. The computer program may be recorded on a suitable computer-readable carrier known to persons skilled in the art. Suitable computer-readable-carriers may include compact discs (including CD-ROMs, DVDs, Blue Rays and the like), floppy discs, flash memory drives, ROM or hard disc drives. The computer program may be installed on a computer suitable for executing the computer program.

The skilled person will appreciate that all non-conflicting embodiments may be used in combination. Hence, embodiments from one aspect of the invention may equally be applied to a second aspect of the invention.

Preferred, non-limiting examples which embody certain aspects of the invention will now be described, with reference to the following figures:

FIG. 1. Binary predictions using the GARD assay. ROC evaluation for (A) binary predictions of benchmark chemicals (filled line) and of 37 new chemicals (dotted line). (B) GARD SVM decision values (DVs) correlate with CLP potency (37 chemicals, 11 1A, 19 1B, 7 no cat). Increasing potency is associated with increasing DVs.

Figure 2:
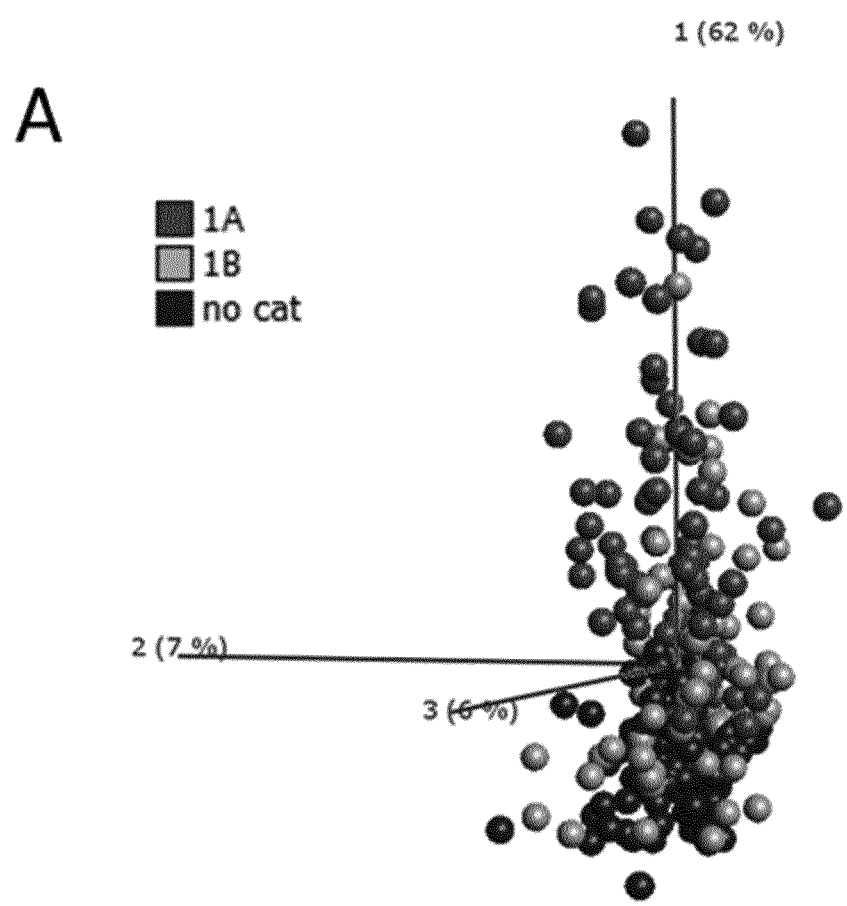
Figure 2:
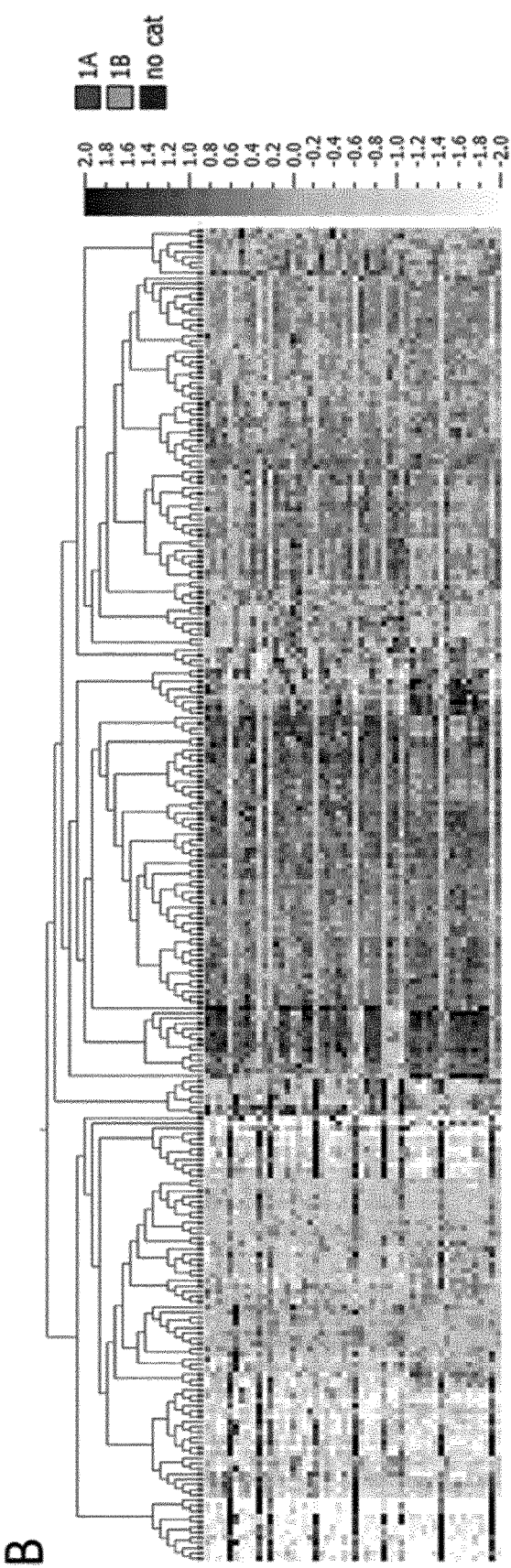

FIG. 2. Visualization of the training dataset used to develop the random forest model, using the 52 variables. (A) PCA plot of the training set with separate biological replicates coloured according to CLP classifications of the chemicals. (B) Heatmap of the training set with replicates of the samples hierarchically clustered, where the grey scale represents the relative gene expression intensity.

Figure 3:
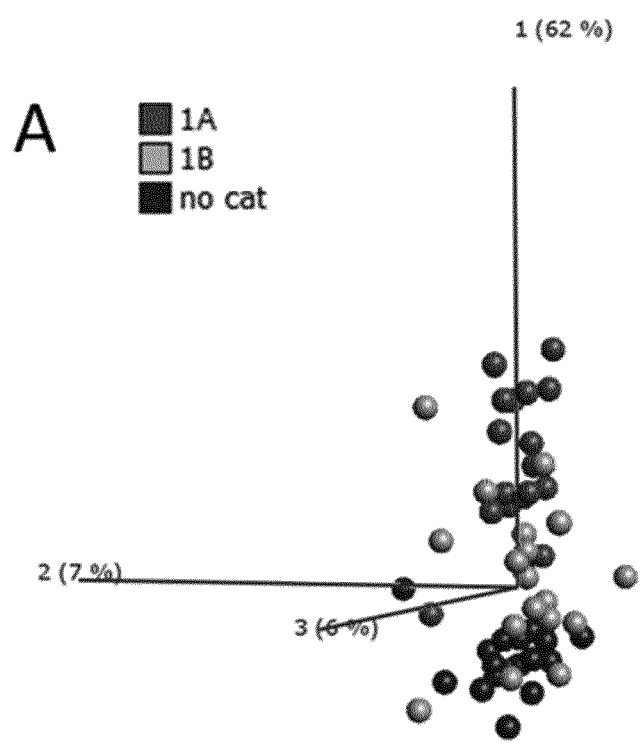
Figure 3:
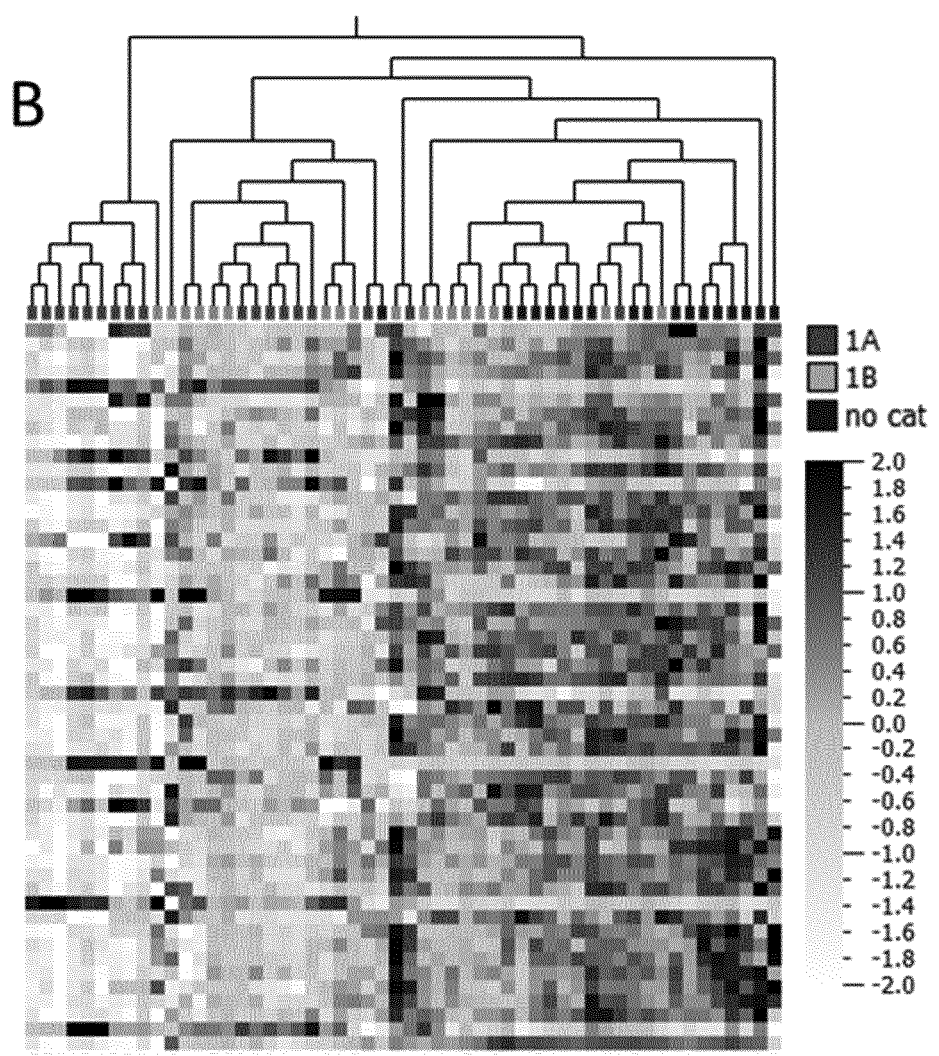

FIG. 3. Visualization of the test dataset using the 52 variables. (A) PCA plot of the test set with separate biological replicates coloured according to CLP classifications. The PCA was built on the training set and the test set plotted without influencing the PCA. (B) Heatmap of the test set with samples hierarchically clustered, where the grey scale represents relative gene expression intensity.

Figure 4:
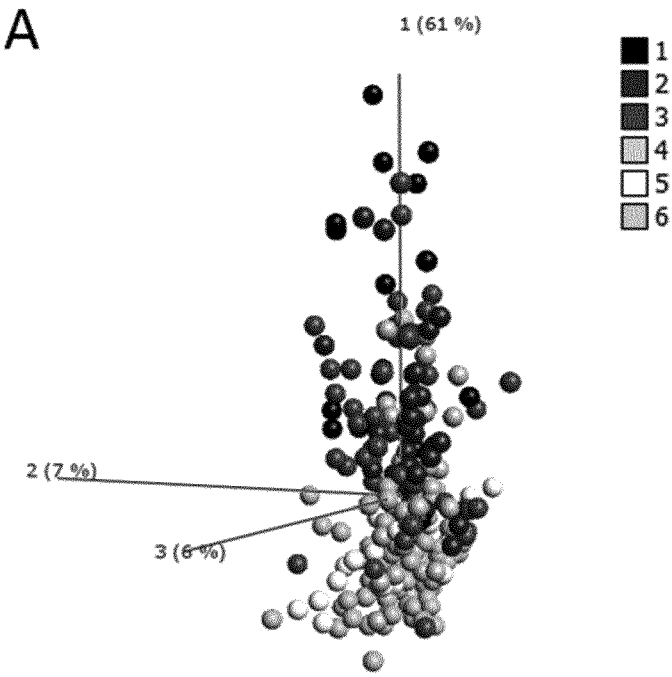
Figure 4:
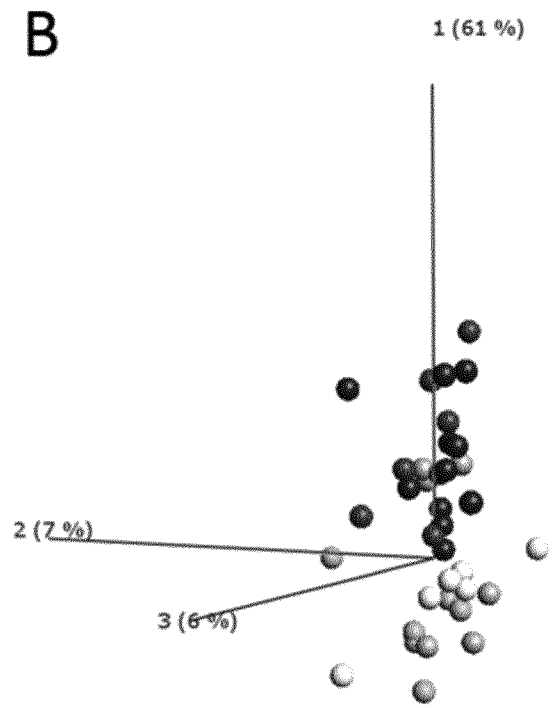

FIG. 4. The CLP potency model contains information related to human potency. (A) PCA plot of replicate training and test set samples with available human potency classifications colored according to human potency. The PCA is based on the 52 Random Forest variables as input and the PCA was built on the training set. (B) PCA plot visualizing test set only.

Figure 5:
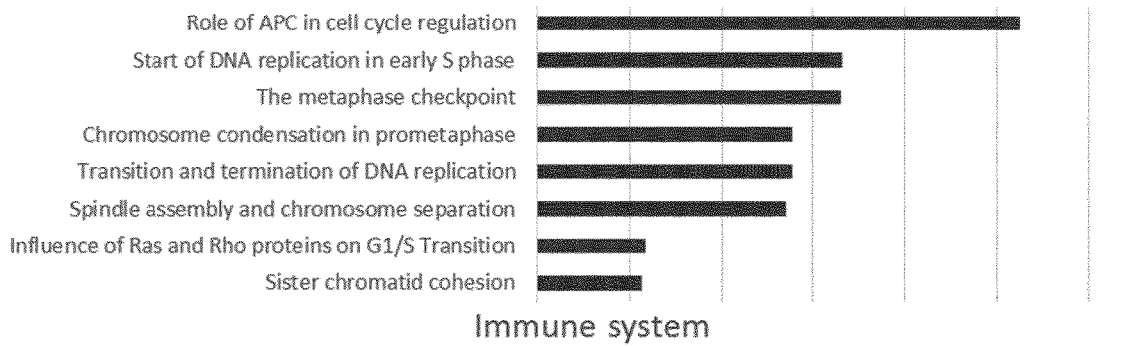
Figure 5:
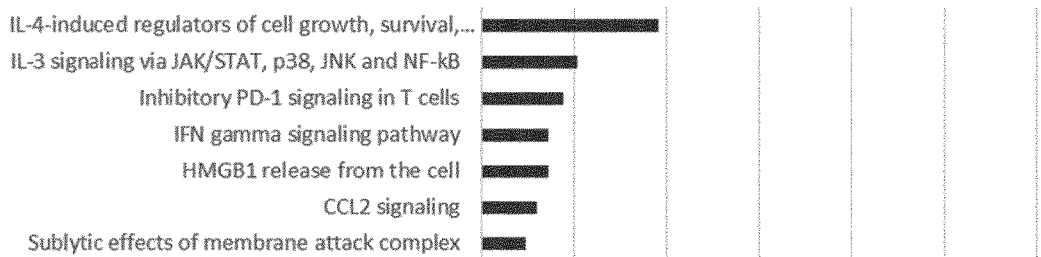
Figure 5:
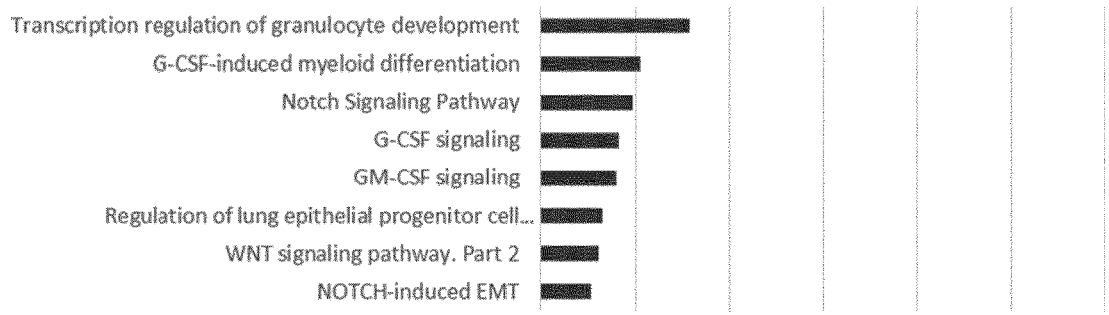
Figure 5:
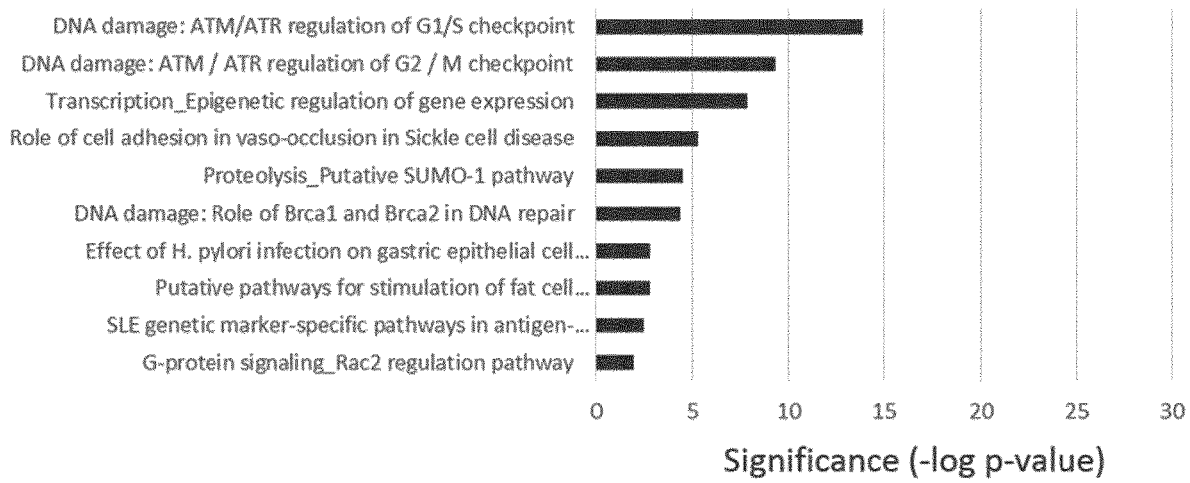

FIG. 5. Pathway analysis based on an input of the 883 most significant genes from a multigroup comparison of the three CLP classes.

Figure 6:
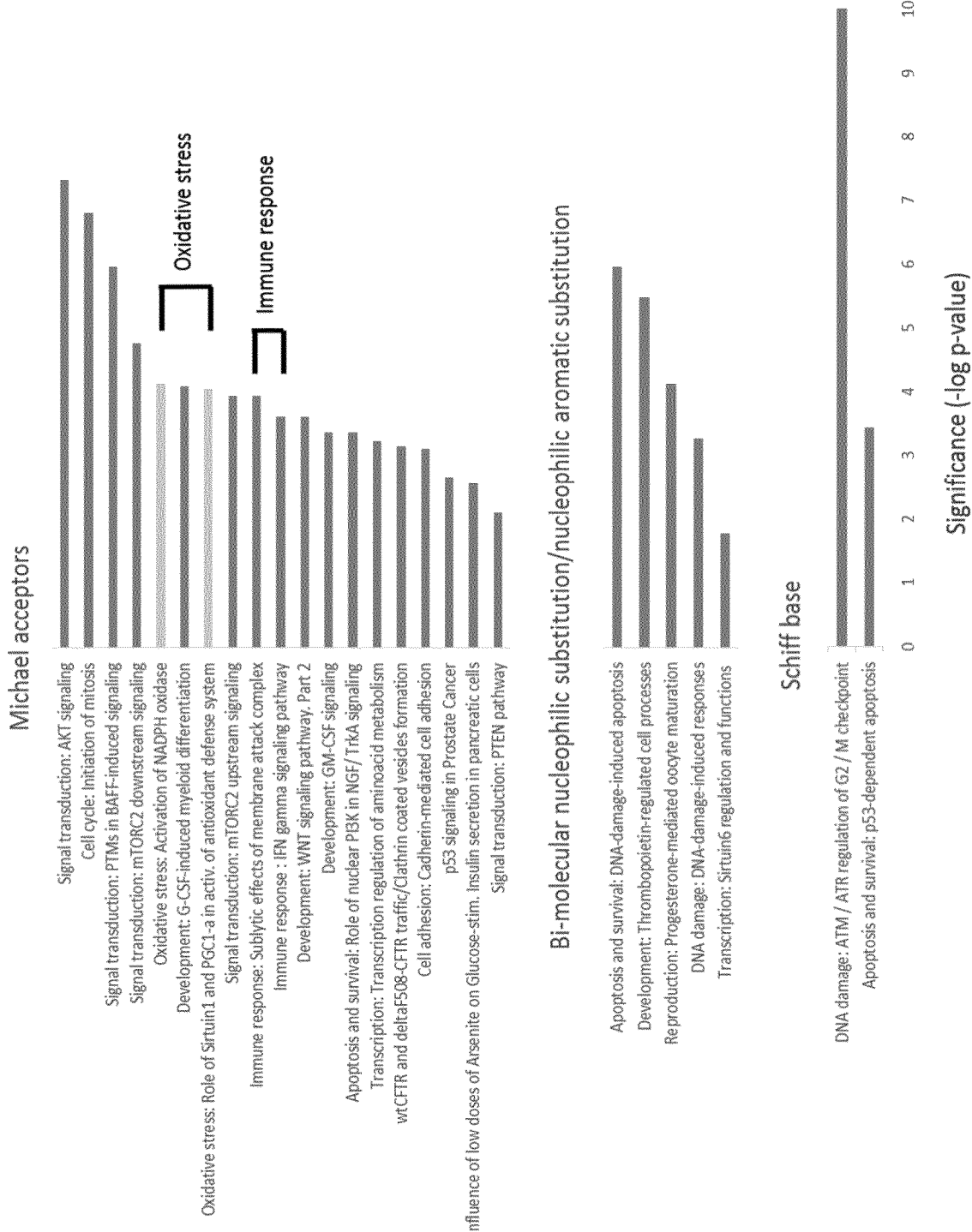

FIG. 6. Pathways unique for each protein reactivity groups, as identified by pathway analysis.

Figure 7:
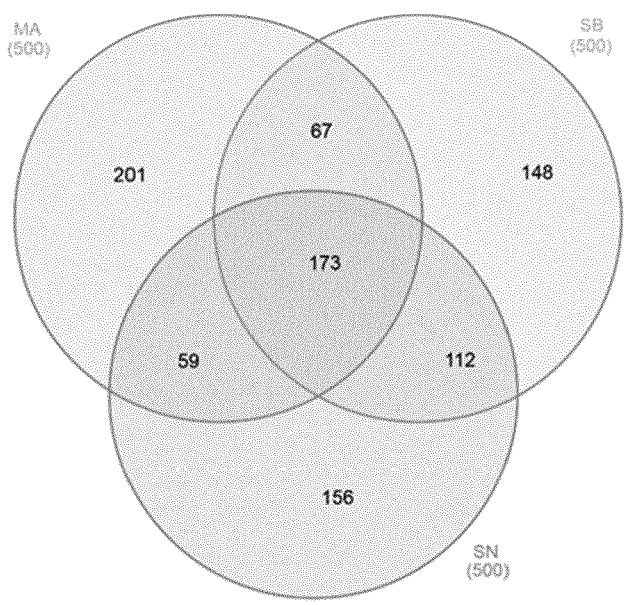
Figure 7:
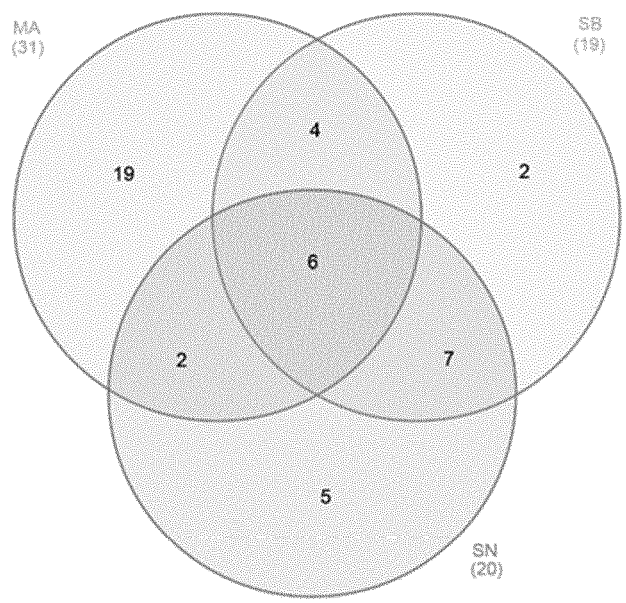

FIG. 7. Venn diagrams [82] of common genes (A) and biological pathways (B) for the three different protein reactivity classes. MA=Michael acceptors; SB=Schiff base formation; SN=bi-molecular nucleophilic substitution/nucleophilic aromatic substitution.

FIG. 8: Genomic Allergen Rapid Detection (GARD)—workflow. The SVM model calculates decision values for each RNA sample derived from chemically treated cells based on the gene expression data of 200 genes that represent the GARD prediction signature. The decision values are then used for binary classification of the chemicals [3]

Figure 9:
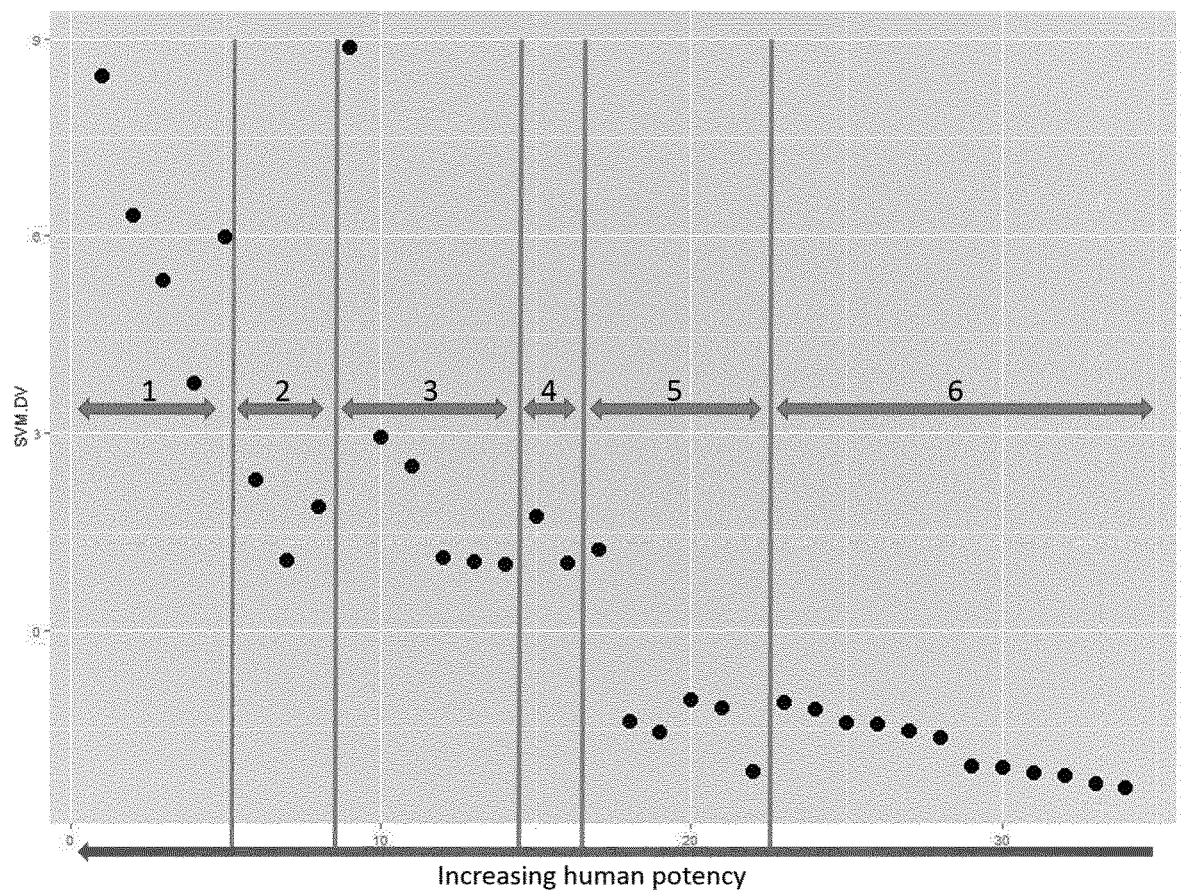

FIG. 9: Relationship between GARD decision values and human potency classes. The chemicals have been sorted according to human potency class and the respective average SVM decision value derived from triplicates can be found on the Y axis. The number on the x-axis refers to the number of the chemical in Table 8.

Figure 10:
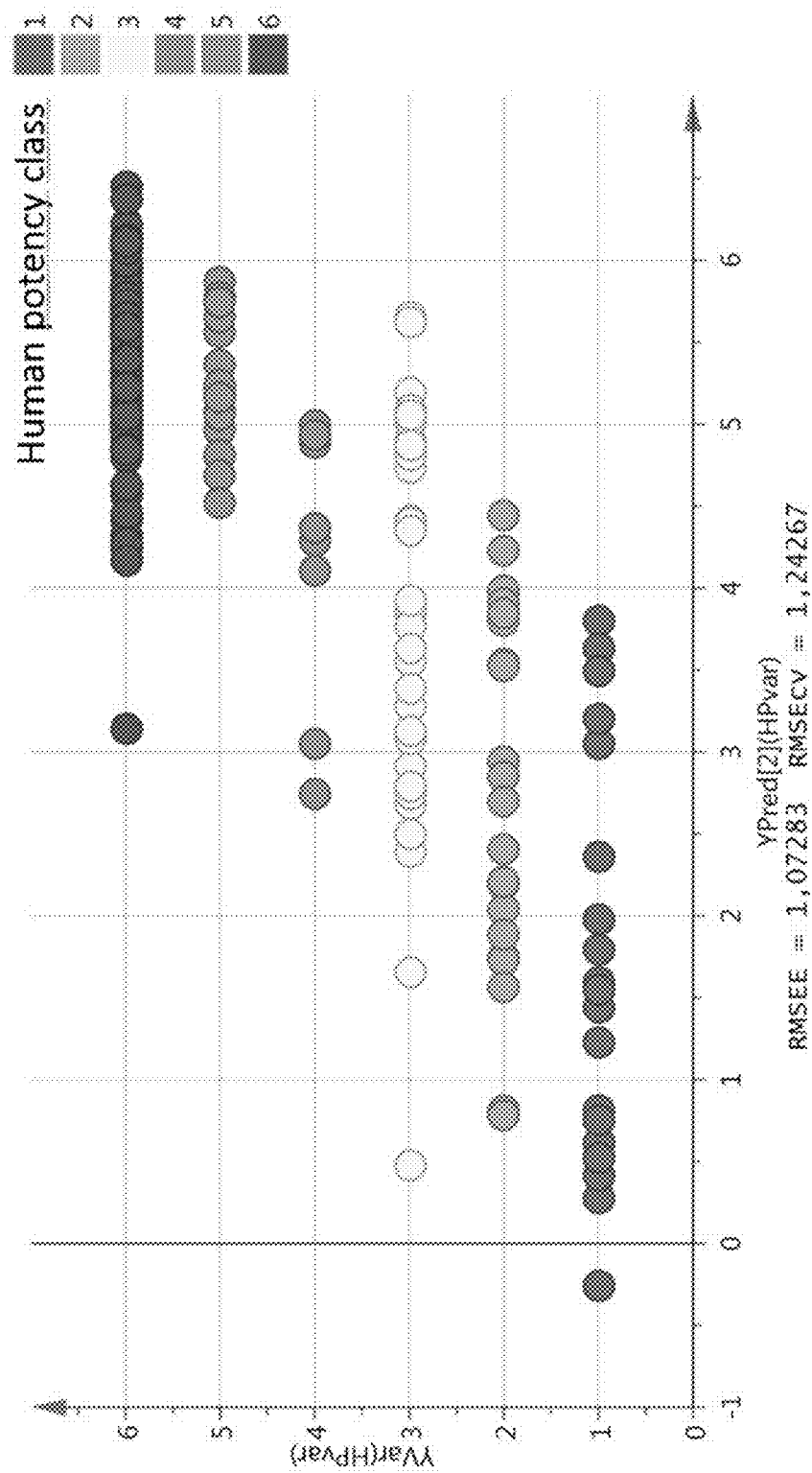

FIG. 10: Scatter plot of O-PLS model (Y=human potency and sensitizer/non-sensitizer) based on 197 samples. Human potency classes as described in Basketter et al. (2014), class 1 representing highest potency, 6 representing non-sensitizers.

Figure 11:
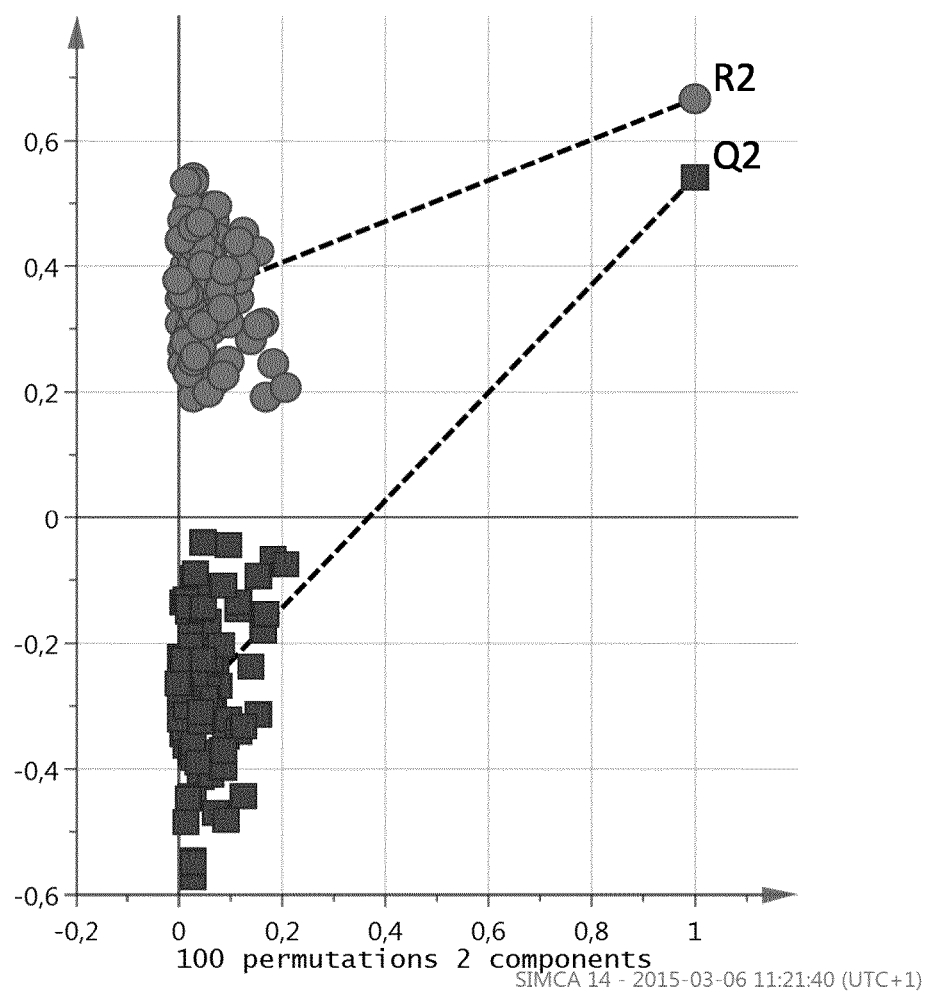

FIG. 11: Permutation plot of O-PLS model. Comparison of goodness of the fit and prediction of the original model with several models, where the order of the Y-observations has been randomly permutated. The plot strongly indicates that the model has not been obtained by chance.

Figure 12:
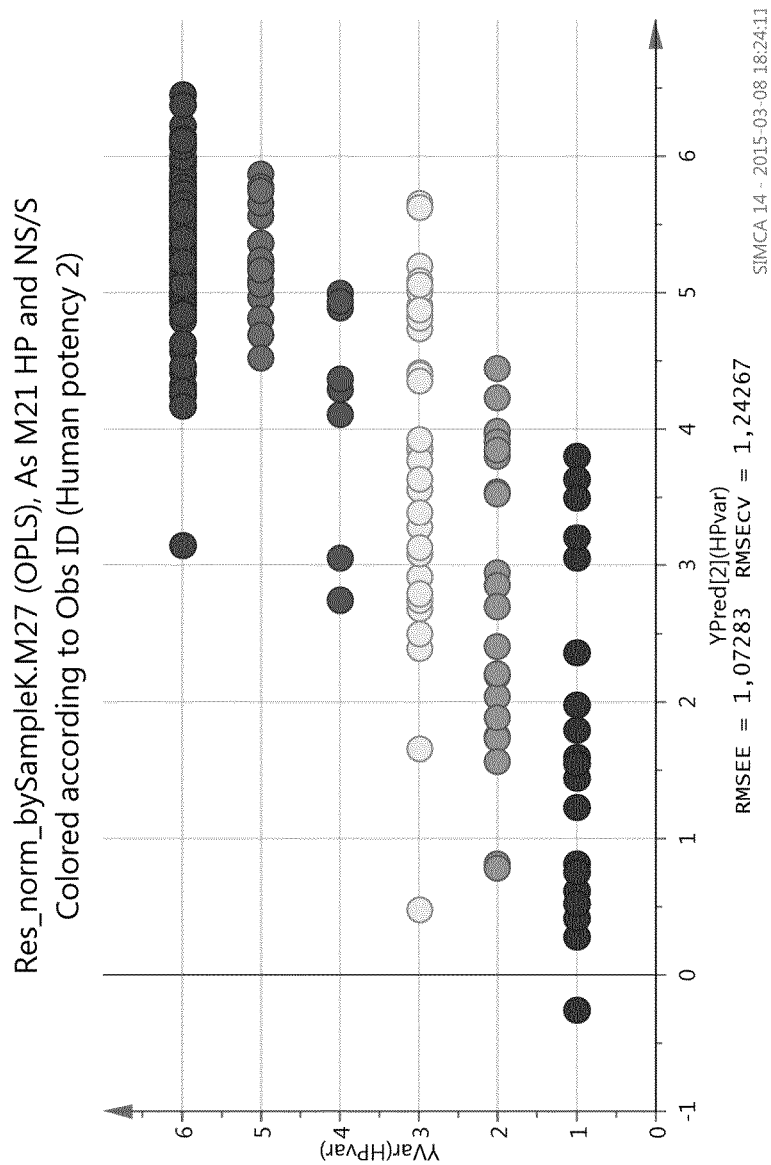

FIG. 12: Observed Y values plotted against predicted Y values. The RMSEE (Root Mean Square Error of Estimation) indicates the fit error of the observations to the model. RMSEcv is a similar measure, but estimated using cross validation.

Figure 13:
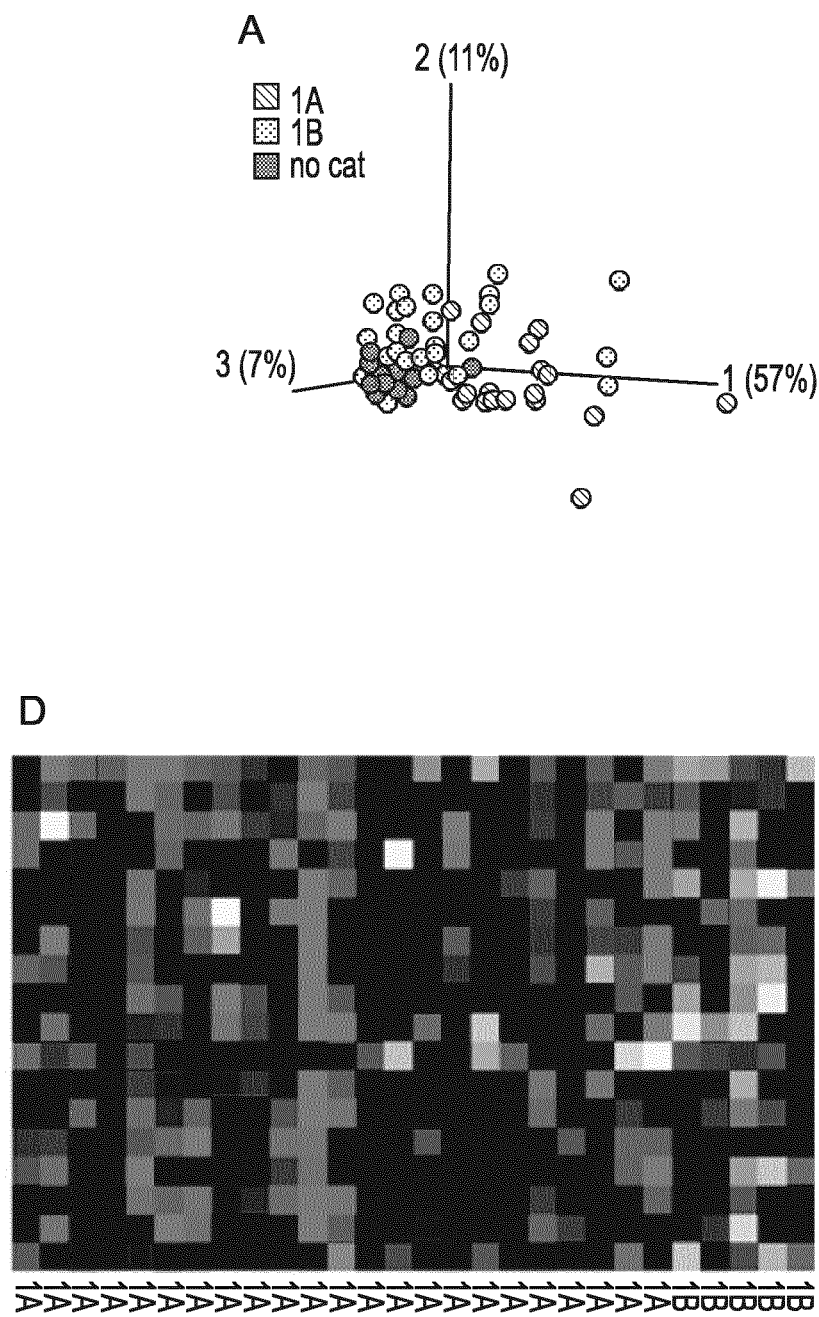
Figure 13:
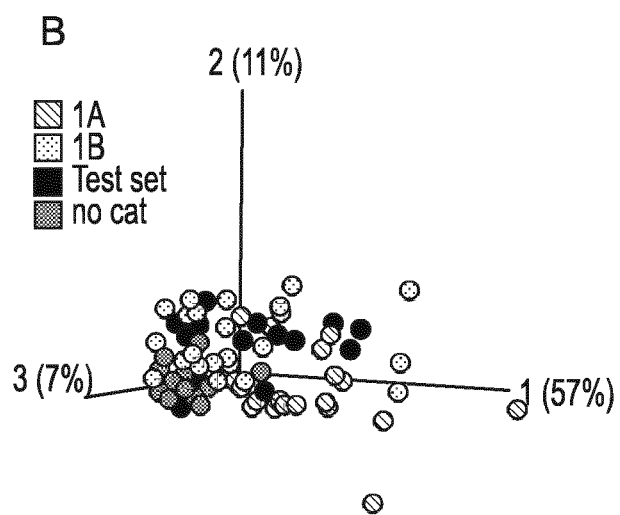
Figure 13:
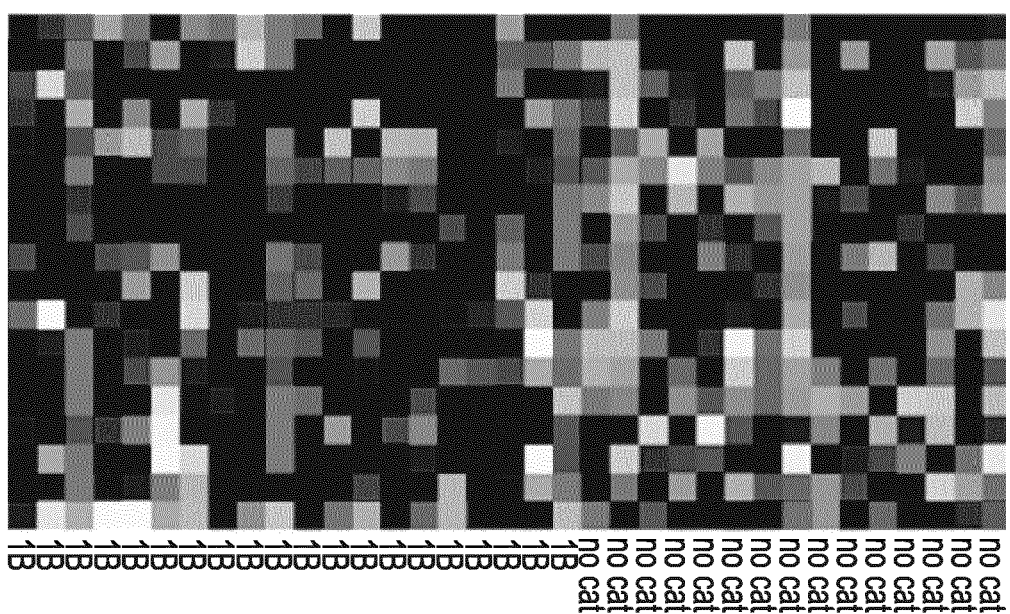
Figure 13:
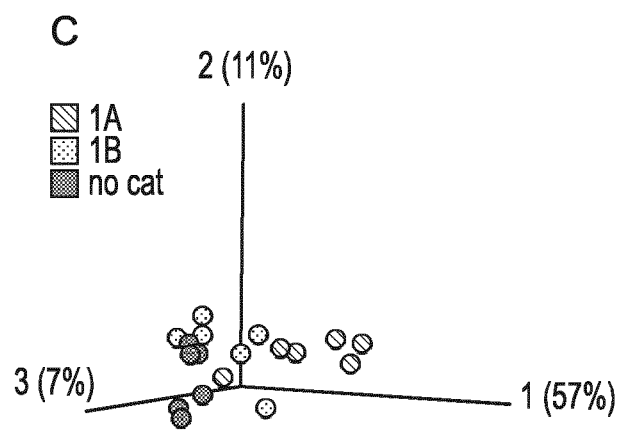
Figure 13:
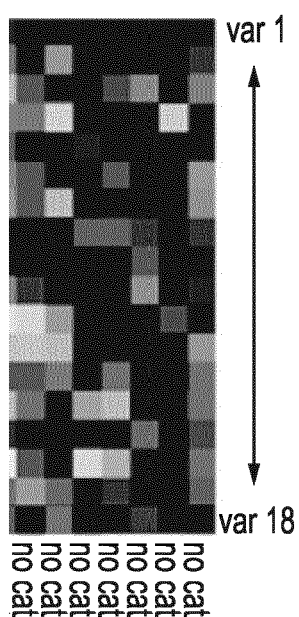
Figure 13:
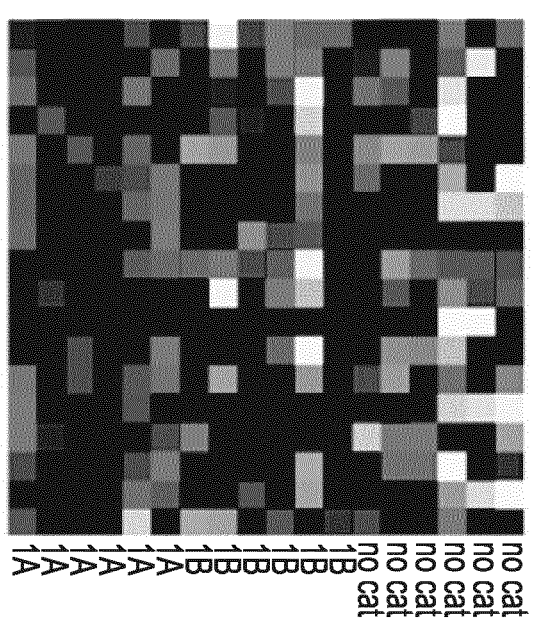

FIG. 13: PCA plots and heat maps. PCA of training set (A), training and test set (B) and test set only (C) based on an input of 18 variables identified by random forest modeling. Each sphere represents a chemical, colored according to CLP classifications (yellow=1A, pink=1B, blue=no category). (D) Heat map of training set and (E) heat map of test set based on the expression of the 18 identified biomarkers.

EXAMPLE A

Introduction

Skin sensitization and associated diseases such as contact allergy affect a substantial portion of the general population with an estimated prevalence of 15-20% in industrialized countries [1]. Allergic contact dermatitis (ACD), a type IV hypersensitivity reaction, is common among certain occupational groups such as those regularly exposed to chemicals or involved in wet work [2]. However, also cosmetics and household products can contain numerous skin sensitizing chemicals. Through different legal frameworks, the European Union has prohibited animal testing for cosmetics and their ingredients [3], and imposed requirements for testing of >60,000 chemicals in the context of REACH [4]. Information on both the skin sensitizing capacity and the potency of a chemical has to be provided to meet the regulatory requirements for classification and sub-categorization. Animal-free alternative assays that meet these requirements are urgently needed.

The molecular events leading to skin sensitization and consequently to ACD can be characterized by a number of sequential key events (KE) triggered by a chemical, and have been summarized in an adverse outcome pathway (AOP) as described by the OECD [5]. The initiating event (KE1) is defined as covalent protein modification by the skin sensitizing chemical after it has gained access to deeper skin layers. The following KE2 represents the inflammatory responses upon activation of keratinocytes. KE3 corresponds to the activation of dendritic cells, which in turn leads to activation and proliferation of T cells (KE4). Upon re-exposure to the sensitizer, the development of ACD may be triggered, which as the adverse outcome is characterized by skin lesions induced by specific Th1 and CD8+ T cells. While the KE in the AOP are well described, a detailed mechanistic understanding of the underlying biology of the individual key events is still missing [5].

The murine Local Lymph Node Assay (LLNA) [6] has for many years been the preferred alternative for skin sensitization testing as it is able to provide data for both hazard identification and characterization, including skin sensitizer potency information. However, it is characterized by certain limitations such as susceptibility to vehicle effects and issues with false-positive results [7]. Several non-animal predictive methods have been developed to reduce animal experimentation used for chemical testing including computational approaches to integrate data from different test platforms for hazard identification as recently reviewed [8]. Three test methods for skin sensitization are accepted as test guidelines at the OECD; the ARE-NRF2 luciferase method (KeratinoSens™) assay [9, 10], the Direct Peptide Reactivity Assay (DPRA) [11] and the human Cell Line Activation Test (h-CIAT) [12]. In addition to hazard identification, information on skin sensitizer potency is imperative in order to allow quantitative risk assessment and to define exposure limits. Few approaches for the prediction of skin sensitizer potency have been published and were recently reviewed in [8], such as assays targeting KE2 (epidermal equivalent sensitizer potency assay [13], SENS-IS [14]) and the U-SENS assay modelling KE3 [15]. Furthermore, in silico models, often combining information from several in vitro methods, have been described; for example QSAR [16], artificial neural network [17], probabilistic models and integrated testing strategy (ITS) approaches including a Bayesian model [18-21].

The alternative assay Genomic Allergen Rapid Detection (GARD) for the assessment of skin sensitization capacity of chemicals is based on global transcriptomic analysis of differential expression in a human myeloid cell line, induced by sensitizing chemicals in comparison to non-sensitizing controls. The resulting biomarker signature, the GARD prediction signature (GPS), consists of 200 transcripts, which are used as input into a support vector machine (SVM) model trained on a set of reference chemicals [22]. The changes in transcription can be linked to the maturation and activation of dendritic cells (KE3) during sensitization. In an in-house study based on 26 blinded chemicals, the accuracy of the assay was estimated to 89% [23]. Previous observations indicated that the GARD assay is able to provide information relevant also for potency assessment. Firstly, signalling pathways were differentially regulated depending on the potency of a subset of chemical reactivity groups [24]. Secondly, we observed that more potent sensitizers were generally assigned higher GARD SVM decision values compared to weaker sensitizers, indicating that there were genes within signature contributing with potency information (unpublished observations). However, the information in the GARD prediction signature were not sufficient to completely stratify chemicals into the well-defined potency groups as described by the Classification, Labelling and Packaging (CLP) Regulation [25].

The CLP regulation is based on the Globally Harmonised System [25], and uses three categories for chemical classification; no category (no cat) for non-sensitizers, category 1B for weak and 1A for strong sensitizers. In the light of the above described observations, it was hypothesized that GARD can be developed further into a tool for the prediction of chemical skin sensitizer potency, targeting the CLP categories. As the established GARD Support Vector Machine model cannot be applied to multiclass problems, we used another approach based on random forest modelling [26]. Random forest is a decision-tree based method and well-suited for microarray data [27]. It divides the dataset internally and repeatedly into a training and test set through random sub-sampling (bootstrapping). Samples in the test set, referred to as out-of-bag samples, comprise approximately one third of the entire dataset, and are used in order to estimate the out-of-bag (OOP) error, i.e. the classification error.

Here, we present a new approach to predict skin sensitizer potency according to CLP categories based on supervised machine learning using a random forest model. Firstly, the global gene expression data from a training set comprising 68 unique chemicals and 2 vehicle control samples were used as input into a random forest model. The random forest model was subsequently combined with an algorithm for backward variable elimination. The algorithm initially ranked the variable importance of each gene from the microarrays, and then iteratively fitted new random forests, while removing the least important variables from the previous iteration. Using this strategy, we were able to identify a set of 52 genes with the smallest OOB error rate when predicting the out-of-bag samples from the training set. The predictive performance of the 52 genes were challenged with an independent test set containing 18 chemicals previously unseen to the model. The chemicals in this test set could be predicted with an overall accuracy of 78%. In addition to the predictive model, we also demonstrated the versatility of analyzing whole transcriptomes of cells by performing pathway analysis to further improve the mechanistic understanding of skin sensitizing potency on a cellular level, confirming the hypothesis that different chemical reactivity classes induce distinct signalling pathways.

Materials and Methods

Cells and Flow Cytometry

The myeloid cell line used in this study was derived from MUTZ-3 (DSMZ, Braunschweig, Germany) and maintained as described in [22, 28]. A phenotypic control analysis of the cells prior to each experiment was carried out by flow cytometry in order to confirm the cells' immature state. The following monoclonal antibodies were used: CD1a (DakoCytomation, Glostrup, Denmark), CD34, CD86, HLA-DR (BD Biosciences, San Jose, USA), all FITC-conjugated; CD14 (DakoCytomation), CD54, CD80 (BD Biosciences), all PE-conjugated. FITC- and PE-conjugated mouse IgG1 (BD Biosciences) served as isotype controls and propidium iodide as a marker for non-viable cells (BD Biosciences). Three batches of cells were exposed for 24 hours in independent experiments and viability and CD86 expression were assessed by flow cytometry. All FACS samples were analyzed on a FACSCanto II instrument with FACS Diva software for data acquisition. 10 000 events were acquired and further analysis was performed in FCS Express V4 (De Novo Software, Los Angeles, Calif.). Cells for RNA extraction were lysed in TRIzol® (Life Technologies/Thermo Fisher Scientific, Waltham, USA) and stored until further use in −20° C.

Chemicals and Stimulations

All chemicals were purchased from Sigma Aldrich (Saint Louis, USA) in high purity quality or they were provided by Cosmetics Europe. All chemicals were stored according to the recommendations of the supplier. The chemical stimulations of cells were performed as described earlier [28]. In short, GARD input concentrations were defined by solubility and cytotoxicity characteristics of the chemicals. An end concentration of 500 µM was targeted for non-cytotoxic and soluble chemicals and the highest possible concentration for chemicals with limited solubility (lower than 500 µM in medium). Cytotoxic chemicals were used in a concentration targeting a relative viability of cells of 90%. Most chemicals were used from a 1000× pre-dilution in dimethyl sulfoxide (DMSO) or autoclaved MilliQ water. DMSO concentration as vehicle never exceeded 0.1%. DMSO and MilliQ samples were included as vehicle controls in this study and thus belong to the group of non-sensitizer samples.

RNA Extraction, cDNA and Array Hybridization

RNA isolation from cells lysed in TRizol® was performed according to the manufacturer's instructions. Labeled sense DNA was synthesized according to Affymetrix (Affymetrix, Cleveland, USA) protocols using the recommended kits and controls. The cDNA was hybridized to Human Gene 1.0 ST arrays (Affymetrix) and further processed and scanned as recommended by the supplier.

Binary Classifications

Binary classifications of the 37 chemicals summarized in Table 1 into sensitizers or non-sensitizers were performed with the previously established model based on SVM, using SCAN-normalized [29, 30] expression data from the GPS as variable input into the learning algorithm [22]. Prior to model construction, potential batch effects between training set and test chemicals were eliminated by scaling array expression values for test chemicals against the training set. A scaling factor was generated by calculating the ratio of the average expression value for each gene in DMSO vehicle control samples of the training set and the average expression value for same gene in DMSO samples in the batch where the test chemical originated. The scaling factor for each gene was then multiplied with the gene expression values for the corresponding gene in the test chemical. SVM predictions were performed as described previously [22, 31]. In short, an SVM model based on a linear kernel was trained on reference chemical stimulations from the original training set used during identification of the GPS [22]. The trained model was subsequently applied to assign each test chemical with an SVM Decision Value (SVM DV). Resulting SVM DVs for all test chemicals were used to construct a receiver operating characteristics (ROC) curve, and the resulting area under the curve (AUC) was used as a classification measure [32]. SVM modeling and ROC curve visualizations were performed in R statistical environment, using the additional packages e1071 [33] and ROCR [34]. Prior to evaluating final predictive performance of the model, SVM DVs for each individual replicate of the test chemicals were calibrated against the cut-off for maximal predictive performance obtained during classification of benchmark samples in Table 2, as described in [31]. The calibrated SVM DVs were subsequently used for final classifications, and test chemicals were classified as sensitizers if the median output value of replicates >0. Accuracy, sensitivity and specificity was estimated using cooper statistics [35]. The non-parametric Two Sample Wilcoxon test was performed in order to determine if the SVM DV distributions between CLP categories 1A, 1B and no cat differed significantly.

Data Handling and Statistical Analysis

In order to build a random forest model, 68 chemicals and two vehicle control samples were defined as a training set, and 18 chemicals, six from each CLP category, were included in the independent test set. Chemicals in the test set were not included in the construction of the model. The aim was to obtain a balanced training set representing all three CLP categories (Table 3) and different chemical reactivity groups (Table 4). Most of the chemicals in the test set (14 out of 18) originated from the latest experimental campaign (Table 1), comprising 37 chemicals previously not investigated using the GARD assay. In the training set, roughly one third of samples (23 out of 68) were from this latest dataset. The vehicle samples were part of all projects and are thus present with higher replicate numbers.

The new microarray data were merged with historical data [22, 23] and subjected to quality control. Four arrays were removed due to bad quality; however, no chemical was present in less than biological duplicates. Array data was imported into the R statistical environment and normalized using the SCANfast algorithm [29, 30]. As several experimental campaigns needed to be combined, this dataset was normalized using the ComBat method [36, 37] in order to remove batch effects between samples. At this time, the samples in the training set were separated from the samples in the test set. To avoid overfitting, only samples in the designated training set were used during identification of the predictive biomarker signature and for fitting of parameters to the classifier, and samples in the test set were set aside to validate the performance of the identified signature and the specified classifier. The predictive biomarker signature was identified by feeding normalized and batch corrected transcript intensities from individual samples in the training set into a random forest model [26] combined with a backward elimination procedure in the varSelRF package [38] in R/Bioconductor version 3.1.2. The initial forest used for ranking of variable importance was grown to 2000 trees and all other parameters were kept at the default settings. The package iteratively fits and evaluates random forest models, at each iteration dropping 20% of the least important variables. The best performing set of variables was selected based on OOB error rates from all fitted Random Forests as the smallest number of genes within one standard error from the minimal error solution (i.e 1.s.e rule). The variable selection procedure was validated by estimating the prediction error rate by the 0.632+ bootstrap method of the varSelRF package using 100 bootstrap samples, and the importance of individual transcripts in the biomarker signature was validated by the frequency of appearance in bootstrap samples (referred to as Validation Call Frequencies (VCF)). The predictive performance of the identified biomarker signature was validated by building a new forest in the Random Forest package [39], based on previous parameters, using only the samples in the training set and the selected transcripts in the biomarker signature as variable input. The model was applied to assign each individual replicate sample in the test set to a CLP category, and the majority vote across the biological replicate stimulations for each chemical was accepted as the predicted category. Heatmaps and Principal Component Analysis (PCA) plots were constructed in Qlucore Omics Explorer (Qlucore AB, Lund, Sweden).

Pathway Analysis

Pathway analysis was performed with the Key Pathway Advisor (KPA) tool [40] version 16.6, which provides a pathway analysis workflow to investigate e.g. gene expression data. It associates differentially expressed genes with both upstream and downstream processes in order to allow biological interpretation. The investigated dataset, consisting of the SCANfast- and ComBat-normalized expression values of the test set and the training set, in total 308 samples, was first variance-filtered in order to remove variables with consistently low variance until approximately a third was left (10009 variables, $\sigma/\sigma_{max}=0.1478$). A multi-group comparison (ANOVA) comparing samples belonging to CLP no cat, 1B, and 1A was then applied in order to identify transcripts that were differentially regulated. The most significant 883 genes (false discovery rate $FDR=10^{-9}$; $p=8.53\times10^{-11}$) were used as input into KPA (Affymetrix Exon IDs and respective p-value, overconnectivity analysis). In order to identify pathways associated with protein reactivity, the same variance-filtered dataset was filtered based on two-group comparisons (t-tests, Toxtree binding class "no binding" non-sensitizers (81 samples) versus "Michael acceptor" sensitizers (MA, 63 samples), "no binding" versus "Schiff base formation" (SB, 29 samples), "no binding" versus combined "bi-molecular nucleophilic substitution/nucleophilic aromatic substitution" (SN, 25 samples). Lists with the 500 most significantly regulated variables from each comparison, together with p-value and fold change (causal reasoning analysis), were then entered into the KPA tool for each protein reactivity group. The lowest p-value was reached when comparing MA samples to "no binding" ($FDR=3.65\times10^{-7}$), followed by SB ($FDR=2.3\times10^{-5}$) and ($FDR=2.44\times10^{-5}$).

Scripts

Listed below are the scripts used for normalization and potency predictions:

Script 1: Used for combating batch effects between different projects prior to model construction:

This script is used for combating batch effects between different projects prior to model construction!
   library (sva)
   library(caret)
   data_set←read.delim("/home/andy/alifiles-scan-norm.txt", stringsAsFactors=F, header=F)
   #Create numerical data set with colnames/rownames and appropriate design matrices and factors
   annotation_headers←data_set[1:17,1]  #Header comprises row 1-17
   annotations←data_set[1:17,2:ncol(data_set)]
   colnames(annotations)←annotations[1,]
   rownames(annotations)←annotation_headers
   rownames_data_set←data_set[,1]
   data_set←data_set[,-1]
   #Convert the data to numerical values
   data_set←data.frame(sapply(data_set[18:nrow(data_set),],as.numeric))

colnames(data_set)←annotations[1,] #The colnames corresponds to the IDs
rownames(data_set)←rownames_data_set[18:length(rownames(data_set))]
projects←factor(as.character(annotations[3,]))
CLP USENS is used in the combat model?
groups←as.character(annotations[7,])
Make the NA unknown
groups[is.na(groups)]←"unknown"
groups←factor(groups)
group_model←model.matrix(~groups)
Remove near-zero-variance probes (could potentially interfere with ComBat)
nzv←nearZeroVar(t(data_set))
data_set←data_set[-nzv,]
The data consists of 5 different projects with pronounced batch effects
ComBat is used to remove the batch effects
normalized_data←ComBat(data_set,projects, mod=group_model)
normalized_data←rbind(annotations,normalized_data)
write.table(normalized_data,"/home/andy/processed_data_sets/ComBat/allfiles    SCAN_ComBat.txt",col.names=F, sep="\t",quote=F)
Script 2: Used for construction of the initial potency model:
Construction of the initial model potencymodel
require(pROC)
require(ROCR)
require(varSelRF)
require(ggplot2)
require(reshape)
require(randomForest)
require(caret)
library(sva)
library(parallel)
library(doMC)
library(foreach)
Load dataset
data1←read.table(file="allfiles-scannorm-cleaned_ComBat.txt",stringsAsFactors=FALSE,row.names=1,header=F, sep="\t")
Define trainingset. Row 10 correspond to annotations with info train/test
trainingset←as.matrix(data1[,which(data1[10,]=="training set")])
trainingsetannot←as.vector(trainingset[7,])
trainingsetannot[which(trainingsetannot=="no cat")]←0
trainingsetclass←as.factor(trainingsetannot)
trainingset←as.matrix(trainingset[-(1:17),])
class(trainingset)←"numeric"
training←as.data.frame(t(trainingset))
Load testdataset 1
testset1←as.matrix(data1[,which(data1[10,]=="test set 1")])
testset1annot←as.vector(testset1[7,])
testset1annot[which(testset1annot=="no cat")]←0
sampleannot←as.vector(testset1[2,])
testset1←as.matrix(testset1[-(1:17),])
class(testset1)←"numeric"
testset1←as.data.frame(t(testset1))
testsetclass←as.factor(testset1annot)
load testdataset 2
testset2←as.matrix(data1[,which(data1[10,]=="test set 2")])
sampleannottest2←as.vector(testset2[2,])
testset2annot←as.vector(testset2[7,])
testset2annot[which(testset2annot=="no cat")]←0
testset2annot←as.factor(testset2annot)
testset2←as.matrix(testset2[-(1:17),])
class(testset2)←"numeric"
testset2←as.data.frame(t(testset2))
Construct the model
set.seed(2)
vsrf←varSelRF(training,Class=trainingsetclass, ntree=2000,ntreeIterat=2000,vars.d rop.frac=0.2, keep.forest=T,whole.range=TRUE,verbose=TRUE)
RFmodel←randomForest(y=trainingsetclass, x=subset(training, select=vsrf$selected.vars),ntree=vsrf$ntreeIterat, importance=TRUE)
rfpr.pred←predict(RFmodel,newdata=subset(testset1, select=vsrf$selected.vars))
confusionMatrix(rfpr.pred,testsetclass)    a←data.frame(stimulant=sampleannot,group=testsetclass, predicted=rfpr.pred)    write.table(a, file="VarSelRF_combat_Test1.txt",    sep=",", row.names=TRUE)
rfpr.pred2←predict(RFmodel,newdata=subset(testset2, select=vsrf$selected.vars))
b←data.frame(stimulant=sampleannottest2, group=testset2annot,predicted=rfpr.pr ed2) write.table(b, file="VarSelRF_combat_Test2.txt",    sep="," row.names=TRUE)
Extract variable importance
write.table(vsrf$selected.vars, file="VarSelRF_ComBat.txt", sep="," row.names=TRUE)
Bootstrapping of variable selection procedure
forkCL←makeForkCluster(12)
clusterSetRNGStream(forkCL, iseed=(100))
clusterEvalQ(forkCL, library(varSelRF))
vsrf.vsb
varSelRFBoot(training,trainingsetclass,usingCluster=T, srf=vsrf,TheCluster=f orkCL,ntree=2000,ntreeIterat=2000, vars.drop.frac=0.2,bootnumber=100) stopCluster(forkCL)
################Shuffle train and test######################
Shuffle train and testset 18 times to make sure primary selection is not biased.#Combine train and test dataset
notest2←as.matrix(data1[,-which(data1[10,]=="test set 2")])
notest2annot←as.vector(notest2[7,])
notest2annot[which(notest2annot=="no cat")]←0
notest2classes←as.factor(notest2annot)
notest2compounds←levels(factor(unlist(as.vector(notest2[2,]))))
notest2←as.matrix(notest2[-(1:17),])
class(notest2)←"numeric"
Generate a new sampling matrix without DMSO and Water! These are controls and should not be used for sampling to test set.
notestDMSO←as.matrix(notest2[,-which(notest2[2,]=="dimethyl sulfoxide")])
notestDMSO_Unstim←as.matrix(notestDMSO[,-which(notestDMSO[2,]=="unstimulated")])
notest2DU←as.vector(notestDMSO_Unstim[7,])
notest2DU[which(notest2DU=="no cat")]←0
notest2DUclasses←as.factor(notest2DU)
###########
construct the shuffling loops
Shuffle train and test 20 times! The results are stored in testcomp, which are accessed through typing testcomp[[i]]
testcomp←c( )
looptest←NULL
looptrain←NULL

```
looptests←list( )
trainingsetannot←list( )
trainingsetclasses←list( )
testsetannot←list( )
testsetclasses←list( )
testsetnames←list( )
vsrf←list( )
rfvsrf←list( )
rfpr.pred←list( )
cf←list( )
results←list( )
testcomploc←list( )
rfpr.predtest2←list( )
resultstest2←list( )
vsrf.vsb←list( )
#cl=makeCluster(4)
#registerDoSNOW(cl)
registerDoMC(18)
startTime=Sys.time( )
writeLines(paste('Starting shuffle: ',startTime, sep=''))
loop_results=foreach(i=1:18,      .packages=c('varSe-
   lRF','caret','randomForest')) % dopar % {
set.seed((10+i))
testcomp←(sample(sort(unique(levels(factor(notestDM-
   SO_Unstim[2,which(notest2DUclasse  s=="1A")]))),
   method="radix"),6))
testcomp←c(testcomp,sample(sort(unique(levels(factor
   (notestDMSO_Unstim[2,which(notes
   t2DUclasses=="1B")]))),method="radix"),6))
testcomp←c(testcomp,sample(sort(unique(levels(factor
   (notestDMSO_Unstim[2,which(notes
   t2DUclasses=="0")]))),method="radix"),6))
testcomploc←c( )
for(n in 1:length(testcomp))
{
testcomploc←c(testcomploc,which(notest2[2,]==tes-
   tcomp[n]))
}
##Get Ids from original matrix containing water and
   DMSO samples.
#testcomploc←unlist(testcomploc)
looptest←notest2[,testcomploc]
looptrain←notest2[,-testcomploc]
trainingsetannot←as.vector(looptrain[7,])
trainingsetannot[which(trainingsetannot=="no cat")]←0
trainingsetclasses←as.factor(trainingsetannot)
looptrain←as.matrix(looptrain[-(1:17),])
class(looptrain)←"numeric"
looptrain←as.data.frame(t(looptrain))
testsetannot←as.vector(looptest[7,])
testsetannot[which(testsetannot=="no cat")]←0
testsetclasses←as.factor(testsetannot)
testsetnames←as.vector(looptest[2,])
looptest←as.matrix(looptest[-(1:17),])
class(looptest)←"numeric"
looptest←as.data.frame(t(looptest))
vsrf←varSelRF(looptrain,Class=trainingsetclasses,
   ntree=2000,    ntreeIterat=2000,vars.drop.frac=0.2,
   keep.forest=T,whole.range=TRUE,verbose=FALSE)
rfvsrf←randomForest(y=trainingsetclasses,    x=subset
   (looptrain,        select=vsrf$selected.vars),
   ntree=vsrf$ntreeIterat,importance=TRUE)
rfpr.pred←predict(rfvsrf,newdata=subset(looptest,
   select=vsrf$selected.vars))
cf←confusionMatrix(rfpr.pred,testsetclasses)
results←t(rbind(stimulant=testsetnames,
   group=testsetclasses,predicted=rfpr.pred))
#List contains all results #Results can be found through
   loop_results[[i]]$
list(Results=results,VarSelRF=vsrf,  RFValSelRF=rfvsrf,
   Predictions=rfpr.pred,Confusion.Matrix=cf,
   TestSet=testsetnames,TestClasses=testsetclasses,
   Train=looptrain,Trainclass=trainingsetclasses)
}
print(loop_results[[2]]$TestSet)
print(loop_results[[2]]$TestSet)
#stopCluster(cl)
##Run Bootstrapping
vsrf.vsb←list( )
for(i in 1:18){
forkCL←makeForkCluster(12)
clusterSetRNGStream(forkCL, iseed=(100+i))
clusterEvalQ(forkCL, library(varSelRF))
vsrf.vsb[[i]]←varSelRFBoot(loop_results[[i]]$Train,
   Class=loop_results[[i]]$Trainclass,usi  ngCluster=T,
   srf=loop_results[[i]]$VarSelRF,TheCluster=forkCL,
   ntree=2000,ntr        eeIterat=2000,vars.drop.frac=0.2,
   bootnumber=100)
stopCluster (forkCL)
print (Sys.time ( ))
}
```

Results

Binary Classifications of 37 Chemicals

A novel dataset comprising 37 well-characterized chemicals (Table 1) was selected in order to complement historical GARD data for 51 chemicals and to represent a relevant choice of chemicals, balanced in terms of chemical reactivity class, and use in consumer products. The novel chemicals were selected based on European Chemical Agency CLP databases and literature [15, 41] and in cooperation with the Skin Tolerance Task Force of Cosmetics Europe (CE), who kindly provided 27 chemicals. The 37 novel chemicals were predicted as sensitizers or non-sensitizers using the GPS and previously established protocols based on SVM classifications. The SVM model was applied to assign each individual replicate sample with a SVM DV. Prior to final classifications, SVM DVs from the 37 samples were first calibrated against 11 benchmark samples (Table 2) included in the same sample batch as the test chemicals. For the purpose of evaluating binary predictions, we here decided to prioritize human data [41] when available, where classes one to four correspond to sensitizers and five and six to non-sensitizer, instead of CLP classifications. Model performance predicting the 37 chemicals is summarized by an AUC ROC of 0.88, indicating a good discriminatory ability, and as illustrated in FIG. 1A (benchmark chemicals-filled line; 37 chemicals-dotted line). The sensitivity, specificity and accuracy based on Cooper statistics were estimated to 73%, 80% and 76%, respectively. In combination with previously published data [23] the updated predictive accuracy of GARD for binary classification of skin sensitizers is estimated to 84% based on a dataset comprising a total of 74 chemicals. When the chemicals in Table 1 were grouped according to CLP classification, and the respective SVM DV values obtained during classification of the 37 chemicals were summarized in a boxplot as presented in FIG. 1B, a potency gradient emerged, as the stronger sensitizers were assigned higher SVM DVs in comparison to the weaker sensitizers in category 1B and the non-sensitizers in no cat. According to non-parametric Two Sample Wilcoxon tests comparing SVM DV sample distributions, these groups differed significantly (no cat vs 1B: $p=2.8^{-5}$; 1B vs 1A $p=2.8^{-6}$, no cat vs 1A $p=3.5^{-12}$). Although the differences between groups were significant, some overlap existed between individual chemicals, indicating that the information was not sufficient to completely stratify samples into well-defined potency groups.

A Random Forest Model for the Prediction of CLP Categories

In order to establish a biomarker signature for prediction of CLP categories, the dataset comprising the 37 novel chemicals were merged with the historical dataset comprising 51 chemicals. In total, the dataset consisted of 86 unique chemicals (Table 4) and two vehicle controls, balanced with regards to categories 1A and 1B and non-sensitizers (no cat) as described by CLP (Table 3). For four chemicals CLP classification 1B was changed to no category/non-sensitizer according to the sources indicated in Table 4 for one of three reasons: i) for retaining consistency with previous GARD projects (benzaldehyde, xylene), ii) for being used as vehicle in non-sensitizing concentration (DMSO), and for being a well-described false-positive in the LLNA (sodium dodecyl sulfate).

A random forest model for the prediction of three CLP categories was developed based on a training set consisting of 70 unique samples, including two vehicle controls. 52 predictive variables (Table 5) were identified as optimal for CLP classification. The model's prediction error rate, derived from bootstrapping, was estimated to 0.225, which provides an indication of model performance. In order to visualize the dataset used to develop the model, principal component analysis (PCA) was performed. The 52 variables identified by random forest based on a whole-genome array analysis were used as input, and the PCA was built on the training set (FIG. 2A). FIG. 2A is based on chemicals with biological replicates colored according to CLP categories and a clear gradient from no cat to strong sensitizers (1A) can be observed along the first principal component. The heatmap of the training set with hierarchical clustering of the variables in FIG. 2B illustrates the regulation of genes in relation to the respective chemical and CLP category.

Prediction of an Independent Test Set

The model performance was further evaluated by predicting the CLP categories of an independent test set, which comprised 18 chemicals previously unseen to the model. The test set colored according to CLP categories was visualized in the PCA plot (FIG. 3A), without influencing the PCA components based on the 52 identified variables. FIG. 3B visualizes the regulation of the 52 genes in the normalized test set in form of a heatmap. When replicates were predicted separately and majority voting was used to classify the respective chemicals, 14 out of 18 chemicals were assigned into the right CLP category (Table 6, Suppl. Table 1), resulting in an overall accuracy of 78% (Table 7). The four misclassified chemicals were diethyl maleate, butyl glycidyl ether, lyral and cyanuric chloride. The only false-negative prediction was cyanuric chloride, which is classified as 1A in CLP and as no cat in our model, whereas the remaining three chemicals are classified as CLP 1B but were predicted as 1A. In a subsequent step to confirm that our selections of training and test set were unbiased and that the predictive model was not entirely dependent on the composition of the training set, we constructed 18 alternative random forest models, where the composition of chemicals in the training and test set were randomly shuffled. For each new model, we repeated the complete process of variable selection as described above. Dependent on the number of replicate samples available for each chemical stimulation, the total number of samples in each training and test set varied, but the number of chemicals in each set and their CLP distribution were kept constant. The alternative models were all significant and the average prediction error rate obtained from the bootstrapping procedure was identical to the initial model at 0.22, which supports that the presented model was not obtained due to a biased choice of training and test sets.

The CLP Potency Model Contains Information Relevant for Human Potency Prediction Next, PCA was utilized in order to investigate how the 52 variables (Table 5) perform using information related to human potency categories [41]. The 70 training and 18 test set samples were colored according to human potency (class 1-6, 6=true non-sensitizer, 1=strongest sensitizer), and samples for which no human potency category was available were removed (see Table 4). Although the model has been developed to predict CLP potency categories, it also contains information related to human potency as illustrated by FIG. 4A, B.

Identity of the Random Forest Model Variables

The 52 variables identified by random forest (Table 5) represent transcripts belonging to different cell compartments and different functional roles. Five of them overlap with the GARD prediction signature. Five of the top 10 markers, which were most frequently chosen in the bootstrapping process and have the highest validation call frequencies (Table 5), are histone cluster 1 members, such as HIST1H2AB [42]. Histones are highly conserved and play an important role not only for maintaining chromatin structure but also in gene regulation [43]. PFAS and PAICS are involved in purine biosynthesis [44, 45], and TMEM97 is a regulator of cholesterol levels [46], which is further described to be involved in cell cycle regulation, cell migration and invasion in a glioma cell model according to RNA interference experiments [47]. DHCR24 is a multifunctional enzyme localized to the endoplasmic reticulum (ER) and catalyzes the final step in cholesterol-synthesis [48] but possesses also anti-apoptotic activity as for example shown for neuronal cells under ER stress [49]. PLK1, a kinase, has been shown to be phosphorylated in response to TLR activation and results from RNA interference suggested that PLK1 signaling was involved in the TLR-induced inflammatory response [50]. PLK1 was further reported to be involved in cell cycle regulation by inhibiting TNF-induced cyclin D1 expression and it could reduce TNF-induced NF-κB activation [51]. Many of the remaining transcripts are nuclear proteins and thus likely involved in DNA-dependent processes such as replication, transcription, splicing and cell cycle regulation. There are further several transcripts in the signature that code for proteins known for their involvement in immune responses and/or sensitization, such as NQO1, which is well-described for its role in the cellular response to skin sensitizers [52]. CD53 belongs to the tetraspanin family, transmembrane proteins which have multiple functions in e.g. cell adhesion, migration and signaling and which has been shown to be elevated on FcεRI-positive skin DCs from atopic dermatitis patients individuals [53] similarly as on peripheral blood-derived monocytes from patients with atopic eczema [54] in comparison to the respective healthy controls. CD44 is a cell surface glycoprotein, adhesion and hyaluronan receptor [55] being expressed by numerous cell types and for example involved in inflammatory responses [56], e.g. by mediating leukocyte migration into inflamed tissues, which has been shown in a mouse model of allergic dermatitis [57].

Common and Unique Regulated Pathways are Induced by Sensitizers Differing in their Protein Reactivity The 33 key pathways identified with an input of the 883 most significantly regulated genes after a multigroup comparison (FDR=10$^{-9}$) between CLP categories in KPA analysis (FIG. 5), mirror several of the functional groups of the 52 variables defined by Random Forest, such as gene regulation, cell cycle control and metabolism. Immune response-associated pathways such as "IL-4-induced regulators of cell growth, survival, differentiation and metabolism" and "Immune response_IL-3 signaling via JAK/STAT, p38, JNK and NF-κB" were among the 50% most significantly regulated ones.

The analyses described subsequently focused on the three largest chemical reactivity groups in the present dataset; nucleophilic substitution (SN), Michael addition (MA) and Schiff base (SB) formation. Among the included chemicals, the majority of chemicals labeled as "no cat" possessed no protein binding properties; however, a few SB formation and SN chemicals were present. In category 1B, almost all protein reactivity types were represented, whereas there was a clear dominance of MA chemicals in category1A.

For each associated protein reactivity, unique pathways could be identified for sensitizing chemicals belonging to the respective protein reactivity group as presented in FIG. 6. These results combine differentially regulated genes from the input data with so-called key hubs, molecules that are able to regulate the expression level of the input genes. They cannot necessarily be identified themselves by gene expression experiments as their regulation may either be visible on other biological levels, such as activity changes (e.g. for kinases) or the changes may be very short-termed or of low magnitude. In total, 173 genes were common for all three reactivity groups (FIG. 7A) and six pathways were present in all three reactivity groups (FIG. 7B); "Cell cycle: Role of APC in cell cycle regulation", "Cell cycle: Role of SCF complex in cell cycle regulation", "Development: Transcription regulation of granulocyte development", "Cell cycle: Cell cycle (generic schema)", "DNA damage: ATM/ATR regulation of G1/S checkpoint", and "Mitogenic action of Estradiol/ESR1 (nuclear) in breast cancer". Again, cell cycle pathways were highly represented. Oxidative stress responses were identified as part of the key pathway results only for MA and SB chemicals (FIG. 6). In the MA sensitizer chemical group, KEAP1 and NRF2 were found as a key hubs as well as their target genes NQO1 and HMOX1 [52, 58] and AHR [59, 60]. For MA chemicals, the target genes NQO1, HMOX1 and CES1 [61] were even present on the input gene level. On the input level, CES1 was present for SN chemicals as well, but only NQO1, NRF2 and AHR were identified as key hubs. KEAP1 was not found as key hub in SB and SN KPA analysis and AHR was the only key hub identified for all three protein reactivity groups. NF-κB subunits (RelB or p52) were predicted key hubs in all reactivity groups except in MA chemicals.

In summary, there seem to be common mechanistic responses to chemical exposures per se such as cell cycle and DNA damage-related, but the pathway analysis results also support the hypothesis that different chemical reactivity classes induce distinct signalling pathways as observed earlier by us [24] and in other experimental systems [14, 21, 62, 63]. Several pathways are linked to processes known to be relevant in skin sensitization.

Discussion

The amount of chemical per exposed skin area that induces sensitization varies significantly [41]; thus, skin sensitizer potency information is imperative for accurate risk assessment. Developers of alternative test method rely on human clinical data in order to achieve high predictivity of human sensitization, however, this type of data is rather scarce and most available data is derived from the LLNA [64]. Despite the fact that animal models reflect the complexity of systemic diseases such as skin sensitization, in vitro data has so far shown to correlate well and perform even better than animal models, especially when combined in an ITS [65]. Furthermore, alternative test systems may provide mechanistic insights that tests using whole animals cannot provide [66].

Here, an approach to predict skin sensitizer potency is presented using the CLP system based on a dendritic cell (DC) model and transcriptional profiling. CLP categories are empirically determined and arbitrarily defined categories, which do not represent the diversity of different chemicals, their molecular features and mechanisms responsible for their sensitizing characteristics or the lack thereof. They are, however, what legislation currently requires in order to classify and label chemicals. We therefore investigated 37 additional chemicals previously not tested in the standard GARD assay, in order to combine these new data with historical datasets. In the binary classifications of these new chemicals according to the established GARD model, four misclassified sensitizing chemicals were close to the cut-off as defined by the benchmark samples, namely aniline, benzocaine, limonene and butyl glycidyl ether. Three of these belong to human potency class 4, which shows that the model cut-off is critical in order to translate the SVM values, often correlating well with potency, into accurate classifications. Together with historical predictions, GARD still shows an overall high accuracy of 84% for binary classifications.

We then used both new and historical data in order to develop a random forest model for each CLP category, which displays balanced accuracies [67] of 96% for no category, 79% for category 1A and 75% for category 1B (based on majority votes, for performance on replicate basis see Table 7). Butyl glycidyl ether, diethyl maleate, cyanuric chloride and lyral were misclassified; the only false-negative prediction was no category instead of 1A for cyanuric chloride. However, cyanuric chloride reacts exothermally with water forming hydrogen chloride and possibly other reaction products. Due to this hydrolyzation reaction, probably already occurring in DMSO (containing water), the amount of cyanuric chloride and reaction products present in the assay are unknown. This chemical may fall outside the applicability domain of GARD platform-based assays. However, nothing in the quality control or other pre-modelling analyses motivated a removal of these samples. Diethyl maleate and lyral are classified as 1B by CLP, but as 1A by our model, which again seems to fit more to their human potency category, category 2, as described by Basketter et al. [41]. The forth misclassified chemical butyl glycidyl ether is a human potency category 3. Obviously, predicting 11B, i.e. weak sensitizers seemed the most challenging part. Also in the LLNA, potency predictions of weak sensitizers vary more than those of strong sensitizers [8, 68, 69]. Furthermore, 1B is a very heterogeneous group, both considering the range of LLNA EC3 concentrations and human potency categories associated to chemicals summarized in category 1B.

The U-SENS™ assay, formerly MUSST, uses another myeloid cell line, U937, and CD86 measurements in order to distinguish sensitizers and non-sensitizers. When the authors combined CD86 with cytotoxicity data and certain cut-off levels in order to predict CLP categories, correct predictions of 82% of Cat. 1A ($^{41}/_{50}$) and 73% of Cat. 1B/No Cat ($^{85}/_{116}$) were reported [15]. However, it remains unclear how the more challenging discrimination between no cat and 1B would turn out. Cottrez et al. [70] have recently published a study, where they report that their alternative assay SENS-IS, a 3D reconstituted epidermis based model, performs very well for the prediction of skin sensitizer potency; however, they do not target CLP categories. Judging from FIG. 4, purely based on the 52 variable input, which was defined in order to predict CLP categories, also our model seems to contain information relevant for human potency classification. Once more chemicals receive human potency classifications, it should be possible to smoothly develop a human potency model based on the GARD platform.

KPA pathway analysis identified biologically relevant events in the presented dataset as several pathways regulated have a known role in skin sensitization, e.g. cytokine signalling and oxidative stress responses (FIGS. 5-6). Although DCs are not the primary target for protein modification in vivo, we hypothesized that different protein reactivity classes influence the DC transcriptome differentially. Protein reactivity is one of the most important features of chemicals defining their skin sensitizing capacity and potency with certain limitations [63]. Protein reactivity-specific patterns were detectable as revealed by the comparison of the most significantly regulated genes induced by the reactivity groups MA, SB, and SN. Interestingly, NF-κB subunits were predicted key hubs for all reactivity groups except for MA chemicals, which may reflect the described inhibitory effect on NF-κB signalling of this type of chemicals [71]. Although some pathways do not seem to fit into the context, such as "Mitogenic action of Estradiol/ESR1 (nuclear) in breast cancer", a closer look at regulated molecules reveals that those are certainly relevant also for other pathways. In this case, for example p21, c-myc, E2F1, SGOL2 (shugoshin 2), and CAD (carbamoyl phosphate synthetase) were involved, whereof the first ones are known cell cycle regulators/transcription factors [72] and play a role in chromosome segregation (SGOL2) [73]. CAD, an enzyme, which is rate-limiting in the biosynthesis of pyrimidine nucleotides, on the other hand, has more recently also been implicated in cooperation with cell signaling pathways [74] and seems to inhibit the bacterial sensor NOD2 (nucleotide-binding oligomerization domain 2) antibacterial function in human intestinal epithelial cells [75]. These examples may illustrate that our transcriptomic data deserves further attention and more detailed analyses and this type of analysis, using different bioinformatics tools and finally, functional analyses, may contribute to elucidate mechanisms underlying biological processes and diseases.

As already discussed above, assigning correct potency classes to chemicals with weak or intermediate potency seems to be a more general problem. Benigni et al. [76] presented data showing that even experimental in vivo systems, though in general correlating well with human data, perform less well for sensitizers of intermediate potency. They further argue that the protein modification step is the rate-limiting step of the whole sensitization process and that in vitro tests targeting other AOP events do not add much information. On the other hand, there is only a weak relationship between the rate constant of MA sensitizers as determined by kinetic profiling with a model peptide and their potency in the LLNA [71]. This was described to be linked to the anti-inflammatory effect of MA chemicals by inhibiting NF-κB signalling, which increases with reactivity. However, considering the key events in the skin sensitization AOP, the sensitization process as such can be understood as a continuum and would thus not just be characterized by isolated events. Of course, in reality the process must start with the chemical penetrating the skin. In this context it should be noted that the concept that a chemical's ability to efficiently penetrate the stratum corneum is crucial for its skin sensitization capacity and potency has recently been proven wrong [77]. Furthermore, access to lower skin layers may in reality be greatly facilitated by impaired skin barrier function, due to e.g. wet work and small wounds. Interestingly, many strong sensitizers possess irritant properties, which correlate with cytotoxicity, and cytotoxicity in turn seems to contribute to sensitizer potency [18], which is also reflected in our dataset (data not shown). Cytotoxicity is also connected to the protein reactivity of the chemical: chemicals, which are strongly cysteine-reactive are in general cytotoxic, and thus may interfere with vital enzyme function [18, 78]. At the same time, irritant effects can generate danger signals such as extracellular ATP or hyaluronic acid degradation products [79, 80], which may serve to activate DCs and consequently, to prime naïve T cells. Additionally, other factors such as pre-existing inflammation and co-exposures to other substances, which certainly play a role in allergic sensitization, may be hard to implement in any test system. As in vitro assays further have to face the demand of being cost-effective and easy to perform, there are obvious limitations what can be achieved in vitro, but the performances of tests so far are very encouraging [76]. Although protein reactivity may be very important, cell-based systems should be capable of recapitulating certain additional events on top of peptide reactivity. Alternative assay performance can most likely be further improved as more mechanistic details of skin sensitization are revealed, which will allow identifying both applicability domains and pitfalls more easily.

In conclusion, we have identified a predictive biomarker signature comprising 52 transcripts for classification of skin sensitizing compounds into CLP groups, as required by current legislation. When challenged with 18 independent test compounds, the assay provided accurate results for 78% of potency predictions. It further identified 11/12 sensitizers correctly, which indicates that it is rather conservative, i.e. avoids false-negative predictions. Since the presented biomarker signature is optimized for potency predictions, and not only for binary hazard classifications, we suggest a possible application for our model within an Integrated Testing Strategy for accurate potency predictions, similar as suggested by [18]. In addition, the results effectively illustrate the flexibility and versatility of the GARD setup. Measuring complete transcriptomes of cells provides the opportunity to perform mode-of-action based studies to identify pathways of sensitization, but also to identify predictive biomarker signatures, which we have previously shown also for binary skin sensitization predictions and respiratory sensitization. Thus, we here present an initial proof of concept of a potency model targeting the CLP groups, which can be modified and improved as more samples are analyzed and more accurate human reference data emerges.

REFERENCES

1. Peiser, M., et al., Allergic contact dermatitis: epidemiology, molecular mechanisms, in vitro methods and regulatory aspects. Current knowledge assembled at an international workshop at BfR, Germany. Cell Mol Life Sci, 2012. 69(5): p. 763-81.
2. Behroozy, A. and T. G. Keegel, Wet-work Exposure: A Main Risk Factor for Occupational Hand Dermatitis. Saf Health Work, 2014. 5(4): p. 175-80.

3. European Parliament, C.o.t.E.U., REGULATION (EC) No 1223/2009 OF THE EUROPEAN PARLIAMENT AND OF THE COUNCIL. 2009.
4. Hartung, T. and C. Rovida, Chemical regulators have overreached. Nature, 2009. 460(7259): p. 1080-1.
5. OECD, The Adverse Outcome Pathway for Skin Sensitisation Initiated by Covalent Binding to Proteins. Part 1: Scientific Evidence. 2012: p. 1-59.
6. Gerberick, G. F., et al., Local lymph node assay (LLNA) for detection of sensitization capacity of chemicals. Methods, 2007. 41(1): p. 54-60.
7. Anderson, S. E., P. D. Siegel, and B. J. Meade, The LLNA: A Brief Review of Recent Advances and Limitations. J Allergy (Cairo), 2011. 2011: p. 424203.
8. Ezendam, J., H. M. Braakhuis, and R. J. Vandebriel, State of the art in non-animal approaches for skin sensitization testing: from individual test methods towards testing strategies. Arch Toxicol, 2016.
9. Andreas, N., et al., The intra- and inter-laboratory reproducibility and predictivity of the KeratinoSens assay to predict skin sensitizers in vitro: Results of a ring-study in five laboratories. Toxicology in Vitro, 2011. 25(3): p. 733-744.
10. Natsch, A. and R. Emter, Skin sensitizers induce antioxidant response element dependent genes: application to the in vitro testing of the sensitization potential of chemicals. Toxicol Sci, 2008. 102(1): p. 110-9.
11. Gerberick, G. F., et al., Development of a peptide reactivity assay for screening contact allergens. Toxicol Sci, 2004. 81(2): p. 332-43.
12. Ashikaga, T., et al., Development of an in vitro skin sensitization test using human cell lines: the human Cell Line Activation Test (h-CLAT). I. Optimization of the h-CLAT protocol. Toxicol In Vitro, 2006. 20(5): p. 767-73.
13. Teunis, M. A., et al., International ring trial of the epidermal equivalent sensitizer potency assay: reproducibility and predictive-capacity. ALTEX, 2014. 31(3): p. 251-68.
14. Cottrez, F., et al., Genes specifically modulated in sensitized skins allow the detection of sensitizers in a reconstructed human skin model. Development of the SENS-IS assay. Toxicol In Vitro, 2015. 29(4): p. 787-802.
15. Piroird, C., et al., The Myeloid U937 Skin Sensitization Test (U-SENS) addresses the activation of dendritic cell event in the adverse outcome pathway for skin sensitization. Toxicol In Vitro, 2015. 29(5): p. 901-16.
16. Dearden, J. C., et al., Mechanism-Based QSAR Modeling of Skin Sensitization. Chem Res Toxicol, 2015. 28(10): p. 1975-86.
17. Tsujita-Inoue, K., et al., Skin sensitization risk assessment model using artificial neural network analysis of data from multiple in vitro assays. Toxicol In Vitro, 2014. 28(4): p. 626-39.
18. Jaworska, J. S., et al., Bayesian integrated testing strategy (ITS) for skin sensitization potency assessment: a decision support system for quantitative weight of evidence and adaptive testing strategy. Arch Toxicol, 2015. 89(12): p. 2355-83.
19. Jaworska, J., et al., Bayesian integrated testing strategy to assess skin sensitization potency: from theory to practice. J Appl Toxicol, 2013. 33(11): p. 1353-64.
20. Luechtefeld, T., et al., Probabilistic hazard assessment for skin sensitization potency by dose-response modeling using feature elimination instead of quantitative structure-activity relationships. J Appl Toxicol, 2015. 35(11): p. 1361-71.
21. Natsch, A., et al., Predicting skin sensitizer potency based on in vitro data from KeratinoSens and kinetic peptide binding: global versus domain-based assessment. Toxicol Sci, 2015. 143(2): p. 319-32.
22. Johansson, H., et al., A genomic biomarker signature can predict skin sensitizers using a cell-based in vitro alternative to animal tests. BMC Genomics, 2011. 12: p. 399.
23. Johansson, H., et al., Genomic allergen rapid detection in-house validation—a proof of concept. Toxicol Sci, 2014. 139(2): p. 362-70.
24. Albrekt, A. S., et al., Skin sensitizers differentially regulate signaling pathways in MUTZ-3 cells in relation to their individual potency. BMC Pharmacol Toxicol, 2014. 15: p. 5.
25. European Parliament, C.o.t.E.U., http://echa.europa.eu/sv/regulations/clp/. accessed Jul. 13, 2016.
26. Breiman, L., Random forests. Machine Learning, 2001. 45.
27. Diaz-Uriarte, R. and S. Alvarez de Andres, Gene selection and classification of microarray data using random forest. BMC Bioinformatics, 2006. 7(1): p. 1-13.
28. Johansson, H., et al., The GARD assay for assessment of chemical skin sensitizers. Toxicol In Vitro, 2013. 27(3): p. 1163-9.
29. Piccolo, S. R., et al., A single-sample microarray normalization method to facilitate personalized-medicine workflows. Genomics, 2012. 100(6): p. 337-44.
30. Stephen R. Piccolo, A. H. B., W. Evan Johnson. https://www.bioconductor.org/packages/release/bioc/html/SCAN.UPC.html. [cited 2016 Oct. 14, 2016]; Bioconductor version: Release (3.3):[
31. Forreryd, A., et al., From genome-wide arrays to tailor-made biomarker readout—Progress towards routine analysis of skin sensitizing chemicals with GARD. Toxicol In Vitro, 2016.
32. Lasko, T. A., et al., The use of receiver operating characteristic curves in biomedical informatics. J Biomed Inform, 2005. 38(5): p. 404-15.
33. Dimitriadou, E., Hornik, K., Leisch, F., Meyer, D., Weingessel, A., e1071: Misc functions of the Department of statistics (q1071). TU Wien. R package version 1.6, 2011. http://CRAN.R-project.org/package=e1071.
34. Sing, T., et al., ROCR: visualizing classifier performance in R. Bioinformatics, 2005. 21(20): p. 3940-1.
35. Cooper, J. A., 2nd, R. Saracci, and P. Cole, Describing the validity of carcinogen screening tests. Br J Cancer, 1979. 39(1): p. 87-9.
36. Jeffrey T. Leek, W. E. J., Hilary S. Parker, Andrew E. Jaffe, John D. Storey, sva: Surrogate Variable Analysis. R package version 3.10.0., 2014.
37. Johnson, W. E., C. Li, and A. Rabinovic, Adjusting batch effects in microarray expression data using empirical Bayes methods. Biostatistics, 2007. 8(1): p. 118-27.
38. Diaz-Uriarte, R., GeneSrF and varSelRF: a web-based tool and R package for gene selection and classification using random forest. BMC Bioinformatics, 2007. 8: p. 328.
39. Wiener, A. L. a. M., Classification and Regression by randomForest. R News, 2002. 2(3), 18-22.
40. Key Pathway Advisor by Clarivate Analytics (Formerly the IP & Science business of Thomson Reuters). http://ipscience.thomsonreuters.com/product/metacore/. 2016.

41. Basketter, D. A., et al., Categorization of chemicals according to their relative human skin sensitizing potency. Dermatitis, 2014. 25(1): p. 11-21.
42. Singh, R., et al., Increasing the complexity of chromatin: functionally distinct roles for replication-dependent histone H2A isoforms in cell proliferation and carcinogenesis. Nucleic Acids Res, 2013. 41(20): p. 9284-95.
43. Harshman, S. W., et al., H1 histones: current perspectives and challenges. Nucleic Acids Res, 2013. 41(21): p. 9593-609.
44. Lane, A. N. and T. W.-M. Fan, Regulation of mammalian nucleotide metabolism and biosynthesis. Nucleic Acids Research, 2015.
45. Li, S. X., et al., Octameric structure of the human bifunctional enzyme PAICS in purine biosynthesis. J Mol Biol, 2007. 366(5): p. 1603-14.
46. Bartz, F., et al., Identification of cholesterol-regulating genes by targeted RNAi screening. Cell Metab, 2009. 10(1): p. 63-75.
47. Qiu, G., et al., RNA interference against TMEM97 inhibits cell proliferation, migration, and invasion in glioma cells. Tumour Biol, 2015. 36(10): p. 8231-8.
48. Waterham, H. R., et al., Mutations in the 3beta-hydroxysterol Delta24-reductase gene cause desmosterolosis, an autosomal recessive disorder of cholesterol biosynthesis. Am J Hum Genet, 2001. 69(4): p. 685-94.
49. Lu, X., et al., 3 beta-hydroxysteroid-Delta 24 reductase (DHCR24) protects neuronal cells from apoptotic cell death induced by endoplasmic reticulum (ER) stress. PLoS One, 2014. 9(1): p. e86753.
50. Hu, J., et al., Polo-like kinase 1 (PLK1) is involved in toll-like receptor (TLR)-mediated TNF-alpha production in monocytic THP-1 cells. PLoS One, 2013. 8(10): p. e78832.
51. Higashimoto, T., et al., Regulation of I(kappa)B kinase complex by phosphorylation of (gamma)-binding domain of I(kappa)B kinase (beta) by Polo-like kinase 1. J Biol Chem, 2008. 283(51): p. 35354-67.
52. Ade, N., et al., HMOX1 and NQO1 genes are upregulated in response to contact sensitizers in dendritic cells and THP-1 cell line: role of the Keap1/Nrf2 pathway. Toxicol Sci, 2009. 107(2): p. 451-60.
53. Peng, W. M., et al., Tetraspanins CD9 and CD81 are molecular partners of trimeric FcvarepsilonRI on human antigen-presenting cells. Allergy, 2011. 66(5): p. 605-11.
54. Jockers, J. J. and N. Novak, Different expression of adhesion molecules and tetraspanins of monocytes of patients with atopic eczema. Allergy, 2006. 61(12): p. 1419-22.
55. Lee-Sayer, S. S., et al., The where, when, how, and why of hyaluronan binding by immune cells. Front Immunol, 2015. 6: p. 150.
56. Johnson, P. and B. Ruffell, CD44 and its role in inflammation and inflammatory diseases. Inflamm Allergy Drug Targets, 2009. 8(3): p. 208-20.
57. Gonda, A., et al., CD44, but not I-selectin, is critically involved in leucocyte migration into the skin in a murine model of allergic dermatitis. Exp Dermatol, 2005. 14(9): p. 700-8.
58. Natsch, A., The Nrf2-Keap1-ARE toxicity pathway as a cellular sensor for skin sensitizers—functional relevance and a hypothesis on innate reactions to skin sensitizers. Toxicol Sci, 2010. 113(2): p. 284-92.
59. Schulz, V. J., et al., Aryl hydrocarbon receptor activation affects the dendritic cell phenotype and function during allergic sensitization. Immunobiology, 2013. 218(8): p. 1055-62.
60. Kohle, C. and K. W. Bock, Coordinate regulation of Phase I and II xenobiotic metabolisms by the Ah receptor and Nrf2. Biochem Pharmacol, 2007. 73(12): p. 1853-62.
61. Roberts, D. W., A. O. Aptula, and G. Patlewicz, Electrophilic chemistry related to skin sensitization. Reaction mechanistic applicability domain classification for a published dataset of 106 chemicals tested in the mouse local lymph node assay. Chem Res Toxicol, 2007. 20(1): p. 44-60.
62. Migdal, C., et al., Reactivity of chemical sensitizers toward amino acids in cellulo plays a role in the activation of the Nrf2-ARE pathway in human monocyte dendritic cells and the THP-1 cell line. Toxicol Sci, 2013. 133(2): p. 259-74.
63. Chipinda, I., J. M. Hettick, and P. D. Siegel, Haptenation: chemical reactivity and protein binding. J Allergy (Cairo), 2011. 2011: p. 839682.
64. Basketter, D. A., et al., Nothing is perfect, not even the local lymph node assay: a commentary and the implications for REACH. Contact Dermatitis, 2009. 60(2): p. 65-9.
65. Urbisch, D., et al., Assessing skin sensitization hazard in mice and men using non-animal test methods. Regul Toxicol Pharmacol, 2015. 71(2): p. 337-51.
66. Natsch, A., et al., Chemical basis for the extreme skin sensitization potency of (E)-4-(ethoxymethylene)-2-phenyloxazol-5(4H)-one. Chem Res Toxicol, 2010. 23(12): p. 1913-20.
67. Brodersen, K. H., et al., The Balanced Accuracy and Its Posterior Distribution, in Proceedings of the 2010 20th International Conference on Pattern Recognition. 2010, IEEE Computer Society. p. 3121-3124.
68. Dumont, C., et al., Analysis of the Local Lymph Node Assay (LLNA) variability for assessing the prediction of skin sensitisation potential and potency of chemicals with non-animal approaches. Toxicol In Vitro, 2016. 34: p. 220-8.
69. Hoffmann, S., LLNA variability: An essential ingredient for a comprehensive assessment of non-animal skin sensitization test methods and strategies. ALTEX, 2015. 32(4): p. 379-83.
70. Cottrez, F., et al., SENS-IS, a 3D reconstituted epidermis based model for quantifying chemical sensitization potency: Reproducibility and predictivity results from an inter-laboratory study. Toxicol In Vitro, 2016. 32: p. 248-60.
71. Natsch, A., T. Haupt, and H. Laue, Relating skin sensitizing potency to chemical reactivity: reactive Michael acceptors inhibit NF-kappaB signaling and are less sensitizing than S(N)Ar- and S(N)2-reactive chemicals. Chem Res Toxicol, 2011. 24(11): p. 2018-27.
72. Buchmann, A. M., S. Swaminathan, and B. Thimmapaya, Regulation of cellular genes in a chromosomal context by the retinoblastoma tumor suppressor protein. Mol Cell Biol, 1998. 18(8): p. 4565-76.
73. Xu, Z., et al., Structure and function of the PP2A-shugoshin interaction. Mol Cell, 2009. 35(4): p. 426-41.
74. Huang, M. and L. M. Graves, De novo synthesis of pyrimidine nucleotides; emerging interfaces with signal transduction pathways. Cell Mol Life Sci, 2003. 60(2): p. 321-36.
75. Richmond, A. L., et al., The nucleotide synthesis enzyme CAD inhibits NOD2 antibacterial function in human intestinal epithelial cells. Gastroenterology, 2012. 142(7): p. 1483-92 e6.
76. Benigni, R., C. Bossa, and O. Tcheremenskaia, A data-based exploration of the adverse outcome pathway for skin sensitization points to the necessary requirements for its prediction with alternative methods. Regul Toxicol Pharmacol, 2016. 78: p. 45-52.
77. Fitzpatrick, J. M., D. W. Roberts, and G. Patlewicz, What determines skin sensitization potency: Myths, maybes and realities. The 500 molecular weight cut-off: An updated analysis. J Appl Toxicol, 2016.
78. Bohme, A., et al., Kinetic glutathione chemoassay to quantify thiol reactivity of organic electrophiles—application to alpha,beta-unsaturated ketones, acrylates, and propiolates. Chem Res Toxicol, 2009. 22(4): p. 742-50.
79. Esser, P. R., et al., Contact sensitizers induce skin inflammation via ROS production and hyaluronic acid degradation. PLoS One, 2012. 7(7): p. e41340.
80. Martin, S. F., et al., Mechanisms of chemical-induced innate immunity in allergic contact dermatitis. Allergy, 2011. 66(9): p. 1152-63.
81. Roggen, E. L. and B. J. Blaauboer, Sens-it-iv: A European Union project to develop novel tools for the identification of skin and respiratory sensitizers. Toxicology in Vitro, 2013. 27(3): p. 1121.
82. Heberle, H., et al., InteractiVenn: a web-based tool for the analysis of sets through Venn diagrams. BMC Bioinformatics, 2015. 16: p. 169.

EXAMPLE 1

Introduction

Based on previous studies we hypothesized that the GARD assay is capable of predicting skin sensitizer potency. Two approaches were pursued in parallel in order to develop potency prediction models. One makes use of our established support vector machine (SVM) trained to provide binary classifications [1-3]. The other approach is based on an orthogonal partial least squares projections to latent structures (O-PLS) linear regression model (Simca, Umetrics, Sweden). O-PLS [5] is a projection method related to principal component analysis and thus well suited for matrices with more variables than observations (or samples) as in the case of whole genome RNA microarray data (>29,000 transcripts). It is a modification of the PLS method (Wold, 1975), designed to divide the structured variability in the matrix X into predictive (correlated with Y) and orthogonal information (not correlated with Y), plus residual variation. This may improve the interpretability of the latent variables (linear combinations of the original variables).

Results

The relationship between GARD SVM decision values and human potency classes for a set of 34 chemicals and controls are illustrated in FIG. 9. The SVM model had been developed for binary classifications (sensitizer versus non-sensitizer).

We have investigated several models in a multivariate approach using the Simca software. Human potency [6] is a classification of chemicals based on available human data combining partly chemically very different substances into one potency category, whereby class 1 represents highest potency and class 6 represents true non-sensitizers.

Here, we present an O-PLS model, which is designed to predict two Ys, namely human potency and sensitizer/non-sensitizer. The scatter plot in FIG. 10 illustrates the separation of sensitizers and non-sensitizers, and the grouping of sensitizers along a second axis into a high- and a low-potency cluster.

The fraction of the total variation that can be explained by the model after cross-validation (Q2cum) is 0.478, which is a value regarded as acceptable/good. A comparison of the goodness of the fit and prediction of the respective original model to the fit of several models with permutated Y-observations (FIG. 11) strongly indicates that the original model is valid. $Y_{observed}$ versus $Y_{predicted}$ is plotted in FIG. 12.

Discussion

In our analyses we see a clear relationship between our microarray data and human potency. Further model development is ongoing and performance is expected to improve with the number and types of chemicals tested. We will also investigate multivariate analysis methods as a feature selection tool, which ultimately may lead to new insights into mechanisms associated with sensitizer potency and provide means to improve the prediction of human potency of chemicals with high accuracy.

EXAMPLE 1 REFERENCES

1. Johansson H et al. *A genomic biomarker signature can predict skin sensitizers using a cell-based in vitro alternative to animal tests*. BMC Genomics. 2011.
2. Johansson H et al. *The GARD assay for assessment of chemical skin sensitizers*. Toxicology in vitro 2013.
3. Johansson H et al. *GARD in-house validation—A proof of concept*. Toxicological Sciences 2014.
4. Albrekt et al. Skin sensitizers differentially regulate signaling pathways in MUTZ-3 cells in relation to their individual potency. BMC Pharmacology and Toxicology 2014.
5. Trygg and Wold. *Orthogonal projections to latent structures (O-PLS)*. Journal of Chemometrics 2002.
6. Basketter et al. *Categorization of chemicals according to their relative human skin sensitizing potency*. Dermatitis 2014.

EXAMPLE 2

Introduction

Based on previous studies we hypothesized that the GARD assay is capable of predicting skin sensitizer potency. Two approaches were pursued in parallel in order to develop potency prediction models. One makes use of our established Support Vector Machine (SVM) trained to provide binary classifications [1-3] and shows correlating GARD SVM decision values and human potency classes [4] for a set of 34 chemicals and controls as illustrated in FIG. 9. The SVM model had been developed for binary classifications (sensitizer versus non-sensitizer).

The other approach is based on Random Forest (RF) modeling, a decision tree-based method well suited for data sets with more variables than observations. It yields good predictive performance even when variables are noisy (no pre-selection required), and returns variable importance [5].

Results

With regard to the sensitizing potency of chemicals, the European Chemical Agency (ECHA) proposes a categorization according to regulation (EC) No 1272/2008 on classification, labelling and packaging of chemical substances and mixtures (CLP) consisting of: 1A (strong sensitizer), 1B (weak sensitizers) and no category (non-sensitizers) [7]. Here, we present a RF model, built on the arithmetic mean of transcript intensities from replicates in the training data using the random forest varSelRF package [6] in R/Bioconductor version 3.1.2 with error rates estimated by the supplied 0.632+ bootstrap method. It may also be built from transcript intensities of replicates directly. The model was trained using the training set described in Table 9 (70 substances), and then challenged with the test set in Table 10

(18 substances). A summary of the model performance is presented in Table 11. FIG. 13 comprises principal component analyses and heat map results of the described random forest model. A list of identified potency biomarkers is presented in Table 12.

Discussion

In our analyses we see a clear relationship between our microarray data and potency information, comprising both human potency and CLP. Using multivariate analysis methods as feature selection tool, new insights into mechanisms associated with sensitizer potency is acquired. Further, it enables prediction of sensitizer potency of chemicals with high accuracy.

EXAMPLE 2 REFERENCES

7. Johansson H et al. *A genomic biomarker signature can predict skin sensitizers using a cell-based in vitro alternative to animal tests*. BMC Genomics. 2011.
8. Johansson H et al. *The GARD assay for assessment of chemical skin sensitizers*. Toxicology in vitro 2013.
9. Johansson H et al. *GARD in-house validation—A proof of concept*. Toxicological Sciences 2014.
10. Basketter et al. *Categorization of chemicals according to their relative human skin sensitizing potency*. Dermatitis 2014
11. Diaz-Uriarte R, Alvarez de Andrés S. Gene selection and classification of microarray data using random forest. BMC Bioinformatics. 2006.
12. Diaz-Uriarte R. *GeneSrF and varSelRF: a web-based tool and R package for gene selection and classification using random forest*. BMC Bioinformatics 2007
13. https://echa.europa.eu/documents/10162/13562/clp_en.pdf.

Tables

TABLE A

| Transcript cluster ID | VCF (%) | Gene Title | Gene Symbol | Gene assignment |
|---|---|---|---|---|
| Table A(i) | | | | |
| 8117594 | 93 | histone cluster 1, H2bm | HIST1H2BM | NM_003521 |
| 8124385 | 86 | histone cluster 1, H4b | HIS11H4B | NM_003544 |
| 8124430 | 81 | histone cluster 1, H1d | HIST1H1D | NM_005320 |
| 8095221 | 80 | phosphoribosylaminoimidazole carboxylase, phosphoribosylaminoimidazole succinocarboxamide synthetase | PAICS | NM_001079524 |
| 8124413 | 69 | histone cluster 1, H4d | HIST1H4D | NM_003539 |
| 8117608 | 56 | histone cluster 1, H2a1///histone cluster 1, H2bn | HIST1H2AL/// HIST1H2BN | NM_003511 |
| 7994109 | 51 | polo-like kinase 1 | PLK1 | NM_005030 |
| 7904433 | 44 | phosphoglycerate dehydrogenase | PHGDH | ENST00000369407 |
| 8082350 | 44 | minichromosome maintenance complex component 2 | MCM2 | NM_004526 |
| 8141395 | 43 | minichromosome maintenance complex component 7 | MCM7 | NM_001278595 |
| 7903893 | 41 | CD53 molecule | CD53 | NM_000560 |
| 8118669 | 41 | kinesin family member C1 | KIFC1 | NM_002263 |
| 7938348 | 40 | WEE1 G2 checkpoint kinase | WEE1 | NM_001143976 |
| 7957737 | 34 | thymopoietin | TMPO | NM_001032283 |
| 8146357 | 34 | minichromosome maintenance complex component 4 | MCM4 | NM_005914 |
| 7918300 | 33 | proline/serine-rich coiled-coil 1 | PSRC1 | NM_001005290 |
| 8054329 | 31 | ring finger protein 149 | RNF149 | NM_173647 |
| 8055426 | 31 | minichromosome maintenance complex component 6 | MCM6 | NM_005915 |
| 8072687 | 29 | minichromosome maintenance complex component 5 | MCM5 | NM_006739 |
| 8003503 | 20 | Fanconi anemia complementation group A | FANCA | NM_000135 |
| Table A(ii) | | | | |
| 8040843 | 44 | carbamoyl-phosphate synthetase 2, aspartate transcarbamylase, and dihydroorotase | CAD | NM_004341 |
| 7898549 | 42 | MRT4 homolog, ribosome maturation factor | MRTO4 | NM_016183 |
| 7901091 | 41 | target of EGR1, member 1 (nuclear) | TOE1 | NM_025077 |
| 7900699 | 40 | cell division cycle 20 | CDC20 | NM_001255 |
| 8121087 | 36 | peptidase M20 domain containing 2 | PM20D2 | NM_00101085 |
| 8084630 | 35 | NmrA-like family domain containing 1 pseudogene | LOC344887 | NR_033752 |
| 7958455 | 30 | uracil DNA glycosylase | UNG | NM_003362 |
| 8119088 | 27 | cyclin-dependent kinase inhibitor 1A (p21, Cip1) | CDKN1A | NM_000389 |
| 8117395 | 26 | histone cluster 1, H2bf | HIST1H2BF | NM_003522 |
| 8124527 | 25 | histone cluster 1, H1b | HIST1H1B | NM_005322 |
| 7896697 | 21 | unknown | unknown | unknown |
| 8097417 | 20 | jade family PHD finger 1 | JADE1 | NM_001287441 |
| 7977445 | 18 | K1AA0125 | KIAA0125 | NR_026800 |

TABLE A-continued

| Transcript cluster ID | VCF (%) | Gene Title | Gene Symbol | Gene assignment |
|---|---|---|---|---|
| 7985213 | 17 | cholinergic receptor, nicotinic alpha 5 | CHRNA5 | NM_000745 |
| 8068478 | 17 | chromatin assembly factor 1, subunit B (p60)///MORC family CW-type zinc finger 3 | CHAF1B///MORC3 | NM_005441 |
| 8099721 | 16 | sel-1 suppressor of lin-12-like 3(C. elegans) | SEL1L3 | NM_015187 |
| 7948192 | 14 | structure specific recognition protein 1 | SSRP1 | NM_003146 |
| 7960340 | 14 | forkhead box M1 | FOXM1 | NM_001243088 |
| 8107706 | 14 | lamin B1 | LMNB1 | NM_001198557 |
| 8124524 | 14 | histone cluster 1, H2ak | HIST1H2AK | NM_003510 |
| 8040712 | 11 | centromere protein A | CENPA | NM_001042426 |
| 8043602 | 10 | non-SMC condensin I complex subunit H | NCAPH | NM_001281710 |
| 8124394 | 7 | histone cluster 1, H2bb | HIST1H2BB | NM_021062 |
| 8144931 | 7 | ATPase, H+ transporting, lysosomal 56/58kDa, V1 subunit B2 | ATP6V1B2 | NM_001693 |
| 7999025 | 5 | TNF receptor-associated protein 1 | TRAP1 | NM_001272049 |

Table A(iii)

| | | | | |
|---|---|---|---|---|
| 8004804 | 83 | phosphoribosylformylglycinamidine synthase | PFAS | NM_012393 |
| 8005839 | 63 | transmembrane protein 97 | TMEM97 | NM_014573 |
| 7916432 | 61 | 24-dehydrocholesterol reductase | DHCR24 | NM_014762 |
| 7948656 | 30 | ferritin, heavy polypeptide 1 | FTH1 | NM_002032 |
| 8117408 | 30 | histone cluster 1, H2ae | HIST1H2AE | NM_021052 |
| 8002303 | 17 | NAD(P)H dehydrogenase, quinone 1 | NQO1 | NM_000903 |
| 7939341 | 8 | CD44 molecule (Indian blood group) | CD44 | NM_000610 |

TABLE 1

37 novel chemicals with CLP annotations used to complement existing GARD data.
S = sensitizer, NS = non-sensitizer

| Name | CAS# | CLP | cytotox | GARD input [M] | binary class (HP*) | GARD binary prediction |
|---|---|---|---|---|---|---|
| 2,4-Dinitrofluorobenzene | 70-34-8 | 1A | yes | 0.00001 | S | S |
| 3-Methylcatechol | 488-17-5 | 1A | yes | 0.00004 | S | S |
| bisphenol A-diglycidyl ether | 1675-54-3 | 1A | yes | 0.00005 | S | S |
| chlorpromazine | 50-53-3 | 1A | yes | 0.0000125 | S | S |
| cyanuric chloride | 108-77-0 | 1A | yes | 0.00005 | S | NS |
| glutaraldehyde | 111-30-8 | 1A | yes | 0.00002 | S | S |
| hexyl salicylate | 6259-76-3 | 1A | yes | 0.00007 | S | S |
| iodopropynyl butylcarbamate | 55406-53-6 | 1A | yes | 0.00001 | S | S |
| methyl heptine carbonate | 111-12-6 | 1A | yes | 0.0001 | S | S |
| p-benzoquinone | 106-51-4 | 1A | yes | 0.00005 | S | S |
| propyl gallate | 121-79-9 | 1A | yes | 0.000125 | S | S |
| abietic acid | 514-10-3 | 1B | no | 0.000125 | S | S |
| amylcinnamyl alcohol | 101-85-9 | 1B | yes | 0.0003 | S | S |
| anethole | 104-46-1 | 1B | no | 0.0005 | NS | S |
| aniline | 62-53-3 | 1B | no | 0.0005 | S | NS |
| anisyl alcohol | 105-13-5 | 1B | no | 0.0005 | NS | NS |
| benzocaine | 94-09-7 | 1B | no | 0.0005 | S | NS |
| benzyl benzoate | 120-51-4 | 1B | yes | 0.0003 | NS | S |
| butyl glycidyl ether | 2426-08-6 | 1B | yes | 0.0005 | S | NS |
| citral | 5392-40-5 | 1B | yes | 0.0000625 | S | S |
| citronellol | 106-22-9 | 1B | no | 0.0005 | NS | S |
| diethanolamine | 111-42-2 | 1B | no | 0.0005 | NS | NS |
| imidazolidinyl urea | 39236-46-9 | 1B | yes | 0.00005 | S | S |
| isopropyl myristate | 110-27-0 | 1B | no | 0.0005 | NS | NS |
| lilial | 80-54-6 | 1B | yes | 0.0001875 | S | S |
| limonene | 5989-27-5 | 1B | no | 0.0005 | S | NS |
| linalool | 78-70-6 | 1B | no | 0.0005 | S | NS |
| lyral | 31906-04-4 | 1B | yes | 0.0001 | S | S |
| pentachlorophenol | 87-86-5 | 1B | no | 0.0000625 | NS | NS |
| pyridine | 110-86-1 | 1B | no | 0.0005 | NS | NS |

TABLE 1-continued 37 novel chemicals with CLP annotations used to complement existing GARD data.
S = sensitizer, NS = non-sensitizer

| Name | CAS# | CLP | cytotox | GARD input [M] | binary class (HP*) | GARD binary prediction |
|---|---|---|---|---|---|---|
| 1-bromobutane | 109-65-9 | no cat | no | 0.0005 | NS | NS |
| benzoic acid | 65-85-0 | no cat | no | 0.0005 | NS | NS |
| benzyl alcohol | 100-51-6 | no cat | no | 0.0005 | NS | NS |
| citric acid | 77-92-9 | no cat | no | 0.0005 | NS | NS |
| dextran | 9004-54-0 | no cat | no | 0.00003 | NS | NS |
| kanamycin A | 25389-94-0 | no cat | no | 0.000125 | NS | NS |
| tartaric acid | 87-69-4 | no cat | no | 0.0005 | NS | NS |

*based on [41] where available; HP 1-4 = S; 5-6 = NS. Otherwise according to CLP. See also Table 4.

TABLE 2

11 benchmark chemicals.

| Chemical | CAS | CLP | Binary class | HP | GARD input [M] |
|---|---|---|---|---|---|
| 2,4-dinitrochlorobenzene | 97-00-7 | 1A | sens | 1 | 0.000004 |
| p-phenylenediamine | 106-50-3 | 1A | sens | 1 | 0.000075 |
| 2-hydroxyethylacrylate | 818-61-1 | 1A | sens | na | 0.0001 |
| 2-nitro-1,4-phenylenediamine | 5307-14-2 | 1A | sens | 2 | 0.0003 |
| 2-am inophenol | 95-55-6 | 1A | sens | 2 | 0.0001 |
| resorcinol | 108-46-3 | 1B | sens | 4 | 0.0005 |
| geraniol | 106-24-1 | 1B | sens | 4 | 0.0005 |
| hexylcinnamic aldehyde | 101-86-0 | 1B | sens | 5 | 0.000032 |
| benzaldehyde* | 100-52-7 | no cat | non-sens | 5 | 0.00025 |
| chlorobenzene | 108-90-7 | no cat | non-sens | 6 | 0.000098 |
| 1-butanol | 71-36-3 | no cat | non-sens | 6 | 0.0005 |

*non-sens according to [41].

TABLE 3

Training and test set composition

| | Total number | CLP 1A | CLP 1B | CLP no cat |
|---|---|---|---|---|
| Training set | 70 | 23 | 25 | 22 |
| Test set | 18 | 6 | 6 | 6 |

TABLE 4

Controls and 86 unique chemicals used to train and test the Random Forest model for the prediction of CLP categories.

| Stimulation | HP | CLP | binary class | set | Toxtree protein binding class |
|---|---|---|---|---|---|
| 1-brombutane | na | no cat | non-sens | test | SN2 |
| anethole | 5 | 1B | sens | test | MA |
| benzoic acid | na | no cat | non-sens | test | No binding |
| benzyl benzoate | 5 | 1B | sens | test | AT |
| bisphenol A-diglycidyl ether | 3 | 1A | sens | test | SN2 |
| butyl glycidyl ether | 3 | 1B | sens | test | SN2 |
| citric acid | na | no cat | non-sens | test | No binding |
| cyanuric chloride | na | 1A | sens | test | SNAr |
| diethyl maleate | 2 | 1B | sens | test | MA |
| diethyl phthalate | 6 | no cat | non-sens | test | No binding |
| ethyl vanillin | nf | no cat | non-sens | test | SB |
| glutaraldehyde | 2 | 1A | sens | test | SB |
| iodopropynyl butylcarbamate | 4 | 1A | sens | test | AT |
| linalool | 4 | 1B | sens | test | No binding |
| lyral | 2 | 1B | sens | test | SB |
| p-benzochinone | na | 1A | sens | test | MA |
| propyl gallate | 2 | 1A | sens | test | MA |
| xylene[1] | 6 | no cat | non-sens | test | No binding |
| 1-butanol | 6 | no cat | non-sens | train | No binding |
| 2,4-dinitrochlorobenzene | 1 | 1A | sens | train | SNAr |

TABLE 4-continued

Controls and 86 unique chemicals used to train and test the Random Forest model for the prediction of CLP categories.

| Stimulation | HP | CLP | binary class | set | Toxtree protein binding class |
|---|---|---|---|---|---|
| 2,4-dinitrofluorobenzene | na | 1A | sens | train | SNAr |
| 2-aminophenol | 2 | 1A | sens | train | MA |
| 2-hydroxyethyl acrylate | 3 | 1A | sens | train | MA |
| 2-mercaptobenzothiazole | 3 | 1A | sens | train | AT |
| 2-nitro-1,4-phenylenediamine | 2 | 1A | sens | train | MA |
| 3-methylcatechol | na | 1A | sens | train | MA |
| 4-methylaminophenol sulfate | 3 | 1A | sens | train | MA |
| 4-nitrobenzylbromide | na | 1A | sens | train | SN2 |
| abietic acid | 3 | 1B | sens | train | No binding |
| amylcinnamyl alcohol | 4 | 1B | sens | train | MA |
| aniline | 4 | 1B | sens | train | No binding |
| anisyl alcohol | 5 | 1B | sens | train | MA/SN2 |
| benzaldehyde[2] | 5 | no cat | non-sens | train | SB |
| benzocaine | 4 | 1B | sens | train | No binding |
| benzyl alcohol | na | no cat | non-sens | train | No binding |
| chloroanilin | na | 1B | sens | train | No binding |
| chlorobenzene | na | no cat | non-sens | train | No binding |
| chlorpromazine | 3 | 1A | sens | train | SB |
| cinnamaldehyde | 2 | 1A | sens | train | MA |
| cinnamyl alcohol | 3 | 1B | sens | train | MA |
| citral | 3 | 1B | sens | train | SB |
| citronellol | 5 | 1B | sens | train | No binding |
| dextran | 6 | no cat | non-sens | train | SB |
| diethanolamine | 5 | 1B | sens | train | No binding |
| dimethyl formamide | nf | no cat | non-sens | train | nf |
| dimethyl sulfoxide[3] | 6 | no cat | non-sens | train | No binding |
| diphenylcyclopropenone | 1 | 1A | sens | train | MA |
| ethylenediamine | 3 | 1B | sens | train | SB |
| eugenol | 3 | 1B | sens | train | MA |
| formaldehyde | 2 | 1A | sens | train | SB |
| geraniol | 4 | 1B | sens | train | SB |
| glycerol | 6 | no cat | non-sens | train | No binding |
| glyoxal | 2 | 1A | sens | train | No binding |
| hexane | 6 | no cat | non-sens | train | No binding |
| hexyl salicylate | 4 | 1A | sens | train | No binding |
| hexylcinnamic aldehyde | 5 | 1B | sens | train | MA |
| hydroquinone | 3 | 1A | sens | train | MA |
| hydroxycitronellal | 4 | 1B | sens | train | SB |
| imidazolidinyl urea | 3 | 1B | sens | train | AT |
| isoeugenol | 2 | 1A | sens | train | MA |
| isopropanol | 5 | no cat | non-sens | train | No binding |
| isopropyl myristate | 5 | 1B | sens | train | No binding |
| kanamycin A | 6 | no cat | non-sens | train | No binding |
| Kathon CG | 1 | 1A | sens | train | nf |
| lactic acid | 6 | no cat | non-sens | train | No binding |
| lauryl gallate | 2 | 1A | sens | train | MA |
| lilial | 4 | 1B | sens | train | SB |
| limonene | 4 | 1B | sens | train | No binding |
| methyl heptine carbonate | 2 | 1A | sens | train | MA |
| methyl salicylate | 5 | no cat | non-sens | train | No binding |
| methyldibromo glutaronitrile | 2 | 1A | sens | train | MA/SN2 |
| octanoic acid | 6 | no cat | non-sens | train | No binding |
| pentachlorophenol | 5 | 1B | sens | train | SNAr |
| phenol | 6 | no cat | non-sens | train | No binding |
| phenyl benzoate | 3 | 1B | sens | train | AT |
| phenylacetaldehyde | na | 1B | sens | train | SB |
| p-hydroxybenzoic acid | nf | no cat | non-sens | train | No binding |
| potassium dichromate | 1 | 1A | sens | train | No binding |
| potassium permanganate | nf | no cat | non-sens | train | nf |
| p-phenylenediamine | 1 | 1A | sens | train | MA |
| pyridine | 5 | 1B | sens | train | No binding |
| resorcinol | 4 | 1B | sens | train | MA |
| salicylic acid | 6 | no cat | non-sens | train | No binding |
| sodium dodecyl sulfate[4] | 6 | no cat | non-sens | train | SN2 |
| tartaric acid | na | no cat | non-sens | train | No binding |
| tetramethylthiuram disulfide | 3 | 1B | sens | train | No binding |
| Tween 80 | 6 | no cat | non-sens | train | na |
| unstimulated | 6 | no cat | non-sens | train | nf |

HP - Human potency; [1,3,4]non-sens Basketter et al.; [2]non-sens according to sens-it-iv project [81] MA - Michael Acceptor; SB - Schiff base formation; AT - Acyl transfer agent; SN2 - bi-molecular nucleophilic substitution; SNAr - nucleophilic aromatic substitution; na - not available; nf - not found.

TABLE 5

The 52 variables identified by random forest modelling as optimal for CLP classification.
VCF = variable call frequency.

| Transcript cluster ID | VCF (%) | Gene Title | Gene Symbol |
|---|---|---|---|
| 8117594 | 93 | histone cluster 1, H2bm | HIST1H2BM |
| 8124385 | 86 | histone cluster 1, H4b | HIST1H4B |
| 8004804 | 83 | phosphoribosylformylglycinamidine synthase | PFAS |
| 8124430 | 81 | histone cluster 1, H1d | HIST1H1D |
| 8095221 | 80 | phosphoribosylaminoimidazole carboxylase, phosphoribosylaminoimidazole succinocarboxamide synthetase | PAICS |
| 8124413 | 69 | histone cluster 1, H4d | HIST1H4D |
| 8005839 | 63 | transmembrane protein 97 | TMEM97 |
| 7916432 | 61 | 24-dehydrocholesterol reductase | DHCR24 |
| 8117608 | 56 | histone cluster 1, H2al/// histone cluster 1, H2bn | HIST1H2AL/// HIST1H2BN |
| 7994109 | 51 | polo-like kinase 1 | PLK1 |
| 7904433 | 44 | phosphoglycerate dehydrogenase | PHGDH |
| 8040843 | 44 | carbamoyl-phosphate synthetase 2, aspartate transcarbamylase, and dihydroorotase | CAD |
| 8082350 | 44 | minichromosome maintenance complex component 2 | MCM2 |
| 8141395 | 43 | minichromosome maintenance complex component 7 | MCM7 |
| 7898549 | 42 | MRT4 homolog, ribosome maturation factor | MRTO4 |
| 7901091 | 41 | target of EGR1, member 1 (nuclear) | TOE1 |
| 7903893 | 41 | CD53 molecule | CD53 |
| 8118669 | 41 | kinesin family member C1 | KIFC1 |
| 7900699 | 40 | cell division cycle 20 | CDC20 |
| 7938348 | 40 | WEE1 G2 checkpoint kinase | WEE1 |
| 8121087 | 36 | peptidase M20 domain containing 2 | PM20D2 |
| 8084630 | 35 | NmrA-like family domain containing 1 pseudogene | LOC344887 |
| 7957737 | 34 | thymopoietin | TMPO |
| 8146357 | 34 | minichromosome maintenance complex component 4 | MCM4 |
| 7918300 | 33 | proline/serine-rich coiled-coil 1 | PSRC1 |
| 8054329 | 31 | ring finger protein 149 | RNF149 |
| 8055426 | 31 | minichromosome maintenance complex component 6 | MCM6 |
| 7948656 | 30 | ferritin, heavy polypeptide 1 | FTH1 |
| 7958455 | 30 | uracil DNA glycosylase | UNG |
| 8117408 | 30 | histone cluster 1, H2ae | HIST1H2AE |
| 8072687 | 29 | minichromosome maintenance complex component 5 | MCM5 |
| 8119088 | 27 | cyclin-dependent kinase inhibitor 1A (p21, Cip1) | CDKN1A |
| 8117395 | 26 | histone cluster 1, H2bf | HIST1H2BF |
| 8124527 | 25 | histone cluster 1, H1b | HIST1H1B |
| 7896697 | 21 | — | — |
| 8003503 | 20 | Fanconi anemia complementation group A | FANCA |
| 8097417 | 20 | jade family PHD finger 1 | JADE1 |
| 7977445 | 18 | KIAA0125 | KIAA0125 |
| 7985213 | 17 | cholinergic receptor, nicotinic alpha 5 | CHRNA5 |
| 8002303 | 17 | NAD(P)H dehydrogenase, quinone 1 | NQO1 |
| 8068478 | 17 | chromatin assembly factor 1, subunit B (p60) /// MORC family CW-type zinc finger 3 | CHAF1B /// MORC3 |
| 8099721 | 16 | sel-1 suppressor of lin-12-like 3 (*C. elegans*) | SEL1L3 |
| 7948192 | 14 | structure specific recognition protein 1 | SSRP1 |
| 7960340 | 14 | forkhead box M1 | FOXM1 |
| 8107706 | 14 | lamin B1 | LMNB1 |
| 8124524 | 14 | histone cluster 1, H2ak | HIST1H2AK |
| 8040712 | 11 | centromere protein A | CENPA |
| 8043602 | 10 | non-SMC condensin I complex subunit H | NCAPH |
| 7939341 | 8 | CD44 molecule (Indian blood group) | CD44 |
| 8124394 | 7 | histone cluster 1, H2bb | HIST1H2BB |
| 8144931 | 7 | ATPase, H+ transporting, lysosomal 56/58 kDa, V1 subunit B2 | ATP6V1B2 |
| 7999025 | 5 | TNF receptor-associated protein 1 | TRAP1 |

TABLE 6

Test set predictions using majority voting.

| Chemical | true CLP | GARD predicted CLP | Human potency [41] | Protein reactivity |
|---|---|---|---|---|
| 1-brombutane | no cat | no cat | na | SN2 |
| benzoic acid | no cat | no cat | na | No binding |
| citric acid | no cat | no cat | na | No binding |
| diethyl phthalate | no cat | no cat | 6 | No binding |
| ethyl vanillin | no cat | no cat | nf | Schiff base formation |
| xylene | no cat | no cat | 6 | No binding |
| anethole | 1B | 1B | 5 | Michael acceptor |
| benzyl benzoate | 1B | 1B | 5 | Acyl transfer agent |

TABLE 6-continued

Test set predictions using majority voting.

| Chemical | true CLP | GARD predicted CLP | Human potency [41] | Protein reactivity |
|---|---|---|---|---|
| linalool | 1B | 1B | 4 | No binding |
| lyral | 1B | 1A | 2 | Schiff base formation |
| butyl glycidyl ether | 1B | 1A | 3 | SN2 |
| diethyl maleate | 1B | 1A | 2 | Michael acceptor |
| cyanuric chloride | 1A | no cat | na | SNAr |
| propyl gallate | 1A | 1A | 2 | Michael acceptor |
| bisphenol A-diglycidyl ether | 1A | 1A | 3 | SN2 |
| glutaraldehyde | 1A | 1A | 2 | Schiff base formation |
| iodopropynyl butylcarbamate | 1A | 1A | 4 | Acyl transfer agent |
| p-benzochinone | 1A | 1A | na | Michael acceptor |

TABLE 7

Statistics by class for separate replicates in the test set predictions.

|  | no cat | 1A | 1B |
|---|---|---|---|
| Sensitivity | 0.889 | 0.833 | 0.556 |
| Specificity | 0.917 | 0.806 | 0.917 |
| Pos predictive value | 0.842 | 0.682 | 0.769 |
| Neg predictive value | 0.943 | 0.902 | 0.805 |
| Prevalence | 0.333 | 0.333 | 0.333 |
| Detection rate | 0.296 | 0.278 | 0.185 |
| Detection prevalence | 0.352 | 0.407 | 0.241 |
| Balanced accuracy | 0.903 | 0.819 | 0.736 |

SUPPL. TABLE 1

Predictions of replicates in the test set.

| Chemical | true CLP | predicted CLP |
|---|---|---|
| bisphenol A-diglycidyl ether | 1A | 1A |
| bisphenol A-diglycidyl ether | 1A | 1A |
| bisphenol A-diglycidyl ether | 1A | 1A |
| cyanuric chloride | 1A | 1B |
| cyanuric chloride | 1A | no cat |
| cyanuric chloride | 1A | no cat |
| glutaraldehyde | 1A | 1A |
| glutaraldehyde | 1A | 1A |
| glutaraldehyde | 1A | 1A |
| iodopropynyl butylcarbamate | 1A | 1A |
| iodopropynyl butylcarbamate | 1A | 1A |
| iodopropynyl butylcarbamate | 1A | 1A |
| p-benzochinone | 1A | 1A |
| p-benzochinone | 1A | 1A |
| p-benzochinone | 1A | 1A |
| propyl gallate | 1A | 1A |
| propyl gallate | 1A | 1A |
| propyl gallate | 1A | 1A |
| anethole | 1B | 1B |
| anethole | 1B | 1B |
| anethole | 1B | 1B |
| benzyl benzoate | 1B | 1B |
| benzyl benzoate | 1B | 1B |
| benzyl benzoate | 1B | 1B |
| butyl glycidyl ether | 1B | 1A |
| butyl glycidyl ether | 1B | 1B |
| butyl glycidyl ether | 1B | 1A |
| diethyl maleate | 1B | 1A |
| diethyl maleate | 1B | 1A |
| diethyl maleate | 1B | 1A |
| linalool | 1B | no cat |
| linalool | 1B | 1B |
| linalool | 1B | 1B |
| lyral | 1B | 1A |
| lyral | 1B | 1B |
| lyral | 1B | 1A |
| 1-brom butane | no cat | no cat |
| 1-brombutane | no cat | no cat |
| 1-brombutane | no cat | no cat |
| benzoic acid | no cat | no cat |
| benzoic acid | no cat | no cat |
| benzoic acid | no cat | no cat |
| citric acid | no cat | no cat |
| citric acid | no cat | 1B |
| citric acid | no cat | no cat |
| diethyl phthalate | no cat | no cat |
| diethyl phthalate | no cat | no cat |
| diethyl phthalate | no cat | no cat |
| ethyl vanillin | no cat | no cat |
| ethyl vanillin | no cat | 1B |
| ethyl vanillin | no cat | no cat |
| xylene | no cat | no cat |
| xylene | no cat | no cat |
| xylene | no cat | no cat |

TABLE B

| Gene Title | Gene Symbol | Transcript Cluster ID | Rank |
|---|---|---|---|
| Table B(i) | | | |
| Cyclin A2 | CCNA2 | 8102643 | 2 |
| Unknown | Unknown | 8151252 | 4 |
| Phosphatidylinositol glycan anchor biosynthesis, class W | PIGW | 8006634 | 5 |
| Small nuclear ribonucleoprotein D1 polypeptide 16kDa | SNRPD1 | 8020411 | 6 |
| Rho GTPase activating protein 19/// ARHGAP19-SLIT1 readthrough (NMD candidate) | ARHGAP19/// ARHGAP19-SLIT1 | 7935403 | 7 |
| Histone cluster 1, H2ab | HIST1H2AB | 8124391 | 8 |
| leucine-rich repeats and calponin homology (CH) domain containing 2 | LRCH2 | 8174610 | 9 |
| plakophilin 4///plakophilin 4 | PKP4///PKP4 | 8045860 | 11 |
| ribonucleoprotein, PTB-binding 2/// ribonucleoprotein, PTB-binding 2 | RAVER2/// RAVER2 | 7902023 | 12 |
| deoxyuridine triphosphatase/// deoxyuridine triphosphatase | DUT///DUT | 7983594 | 13 |
| aurora kinase A | AURKA | 8067167 | 14 |
| Unknown | Unknown | 8055309 | 15 |
| NDC1 transmembrane nucleoporin | NDC1 | 7916316 | 16 |
| kinesin family member 2/// kinesin family member 2 | KIF22///KIF22 | 7994620 | 17 |
| OK/SW-CL.58 | OK/SW-CL.58 | 7970828 | 18 |
| Unknown | Unknown | 7994343 | 19 |
| Table B(ii) | | | |
| Histone cluster 1, H2ab/// histone cluster 1, H2ae | HIST1H2AB/// HIST1H2AE | 8117408 | 1 |
| high mobility group box 3 | HMGB3 | 8170468 | 10 |

TABLE 8

Chemical list
class 1 representing highest potency, 6 representing non-sensitizers

| number | chemical | SVM DV | Human potency |
|---|---|---|---|
| 1 | Potassium dichromate | 8.45 | 1 |
| 2 | Di nitrochlorobenzene | 6.31 | 1 |
| 3 | PPD | 5.32 | 1 |
| 4 | Kathon CG | 3.76 | 1 |
| 5 | 2-Aminophenol | 5.98 | 2 |
| 6 | Formaldehyde | 2.32 | 2 |
| 7 | Glyoxal | 1.08 | 2 |
| 8 | Iso-eugenol | 1.91 | 2 |
| 9 | 2-Hydroxyethyl acrylate | 8.87 | 3 |
| 10 | Cinnamic alcohol | 2.94 | 3 |
| 11 | 2-Mercaptobenzothiazole | 2.52 | 3 |
| 12 | Ethylenediamine | 1.12 | 3 |
| 13 | Penicillin G | 1.06 | 3 |
| 14 | Eugenol | 1.02 | 3 |
| 15 | Geraniol | 1.76 | 4 |
| 16 | Resorcinol | 1.03 | 4 |
| 17 | Hexylcinnamic aldehyde | 1.24 | 5 |
| 18 | Isopropanol | −1.37 | 5 |
| 19 | Methyl salicylate | −1.53 | 5 |
| 20 | PABA | −1.04 | 5 |
| 21 | Propylene glycol | −1.18 | 5 |
| 22 | Benzaldehyde | −2.13 | 5 |
| 23 | Phenol | −1.08 | 6 |
| 24 | Octanoic acid | −1.19 | 6 |
| 25 | Tween 80 | −1.39 | 6 |
| 26 | Salicylic acid | −1.41 | 6 |
| 27 | Sodium lauryl sulfate | −1.52 | 6 |
| 28 | Chlorobenzene | −1.63 | 6 |
| 29 | Glycerol | −2.05 | 6 |
| 30 | 1-Butanol | −2.07 | 6 |
| 31 | Diethyl phthalate | −2.15 | 6 |
| 32 | Unstimulated | −2.20 | 6 |
| 33 | DMSO | −2.31 | 6 |
| 34 | Lactic acid | −2.38 | 6 |

TABLE 9

Chemicals training set

| Chemical | Can | CLP | set | vehicle | GARD input [M] |
|---|---|---|---|---|---|
| 2,4-dinitrochlorobenzene | 97-00-7 | 1A | training set | DMSO | 0.000004 |
| p-phenylenediamine | 106-50-3 | 1A | training set | DMSO | 0.0003 |
| sodium dodecyl sulfate | 151-21-3 | no cat | training set | H2O | 0.0002 |
| salicylic acid | 69-72-7 | no cat | training set | H2O | 0.0005 |
| phenol | 108-95-2 | no cat | training set | H2O | 0.0005 |
| glycerol | 56-81-5 | no cat | training set | H2O | 0.0005 |
| lactic acid | 50-21-5 | no cat | training set | H2O | 0.0005 |
| chlorobenzene | 108-90-7 | no cat | training set | DMSO | 0.000098 |
| p-hydroxybenzoic acid | 99-96-7 | no cat | training set | DMSO | 0.00025 |
| benzaldehyde | 100-52-7 | no cat | training set | DMSO | 0.00025 |
| octanoic acid | 124-07-2 | no cat | training set | DMSO | 0.0005 |
| unstimulated | | no cat | training set | H2O | vehicle |
| dimethyl sulfoxide | 67-68-5 | no cat | training set | DMSO | vehicle |
| glyoxal | 107-22-2 | 1A | training set | H2O | 0.0003 |
| 2-mercaptobenzothiazole | 149-30-4 | 1A | training set | DMSO | 0.00025 |
| resorcinol | 108-46-3 | 1B | training set | H2O | 0.0005 |
| isoeugenol | 97-54-1 | 1A | training set | DMSO | 0.0003 |
| eugenol | 97-53-0 | 1B | training set | DMSO | 0.0003 |
| cinnamyl alcohol | 104-54-1 | 1B | training set | DMSO | 0.0005 |
| geraniol | 106-24-1 | 1B | training set | DMSO | 0.0005 |
| 2-nitro-1,4-phenylenediamine | 5307-14-2 | 1A | training set | DMSO | 0.0003 |
| isopropanol | 67-63-0 | no cat | training set | H2O | 0.0005 |
| Tween 80 | 9005-65-6 | no cat | training set | DMSO | 0.0005 |
| 2-hydroxyethyl acrylate | 818-61-1 | 1A | training set | H2O | 0.0001 |
| formaldehyde | 50-00-0 | 1A | training set | H2O | 0.00008 |
| Kathon CO | 96118-96-6 | 1A | training set | H2O | 0.0035% |
| hexylcinnamic aldehyde | 101-86-0 | 1B | training set | DMSO | 0.00603224 |
| 2-aminophenol | 95-55-6 | 1A | training set | DMSO | 0.0001 |
| methyl salicylate | 119-36-8 | no cat | training set | DMSO | 0.0005 |
| ethylenediamine | 107-15-3 | 1B | training set | H2O | 0.0005 |
| potassium dichromate | 7778-50-9 | 1A | training set | H2O | 0.0000015 |
| dimethyl formamide | 66-12-2 | no cat | training set | H2O | 0.0005 |
| 1-butanol | 71-36-3 | no cat | training set | DMSO | 0.0005 |
| potassium permanganate | 7722-64-7 | no cat | training set | H2O | 0.000038 |
| phenylacetaldehyde | 122-78-1 | 1B | training set | DMSO | 0.00005 |
| hydroquinone | 123-31-9 | 1A | training set | DMSO | 0.00002 |
| 4-nitrobenzylbromide | 100-11-8 | 1A | training set | DMSO | 0.0000015 |
| diphenylcyclopropenone | 886-38-4 | 1A | training set | DMSO | 0.000005 |
| hexane | 110-54-3 | no cat | training set | DMSO | 0.0005 |
| phenyl benzoate | 93-99-2 | 1B | training set | DMSO | 0.0002-0.0005 |
| 4-methylaminophenol sulfate | 55-55-0 | 1A | training set | DMSO | 0.000007 |
| hydroxycitronellal | 107-75-5 | 1B | training set | DMSO | 0.0005 |
| chloroanilin | 106-47-8 | 1B | training set | DMSO | 0.0005 |
| Tetramethylthiuram disulfide | 137-26-8 | 1B | training set | DMSO | 0.0000001 |
| lauryl gallate | 1166-52-5 | 1A | training set | DMSO | 0.000003 |
| cinnamaldehyde | 104-55-2 | 1A | training set | DMSO | 0.00005 |
| methyldibromo glutaronitrile | 35691-65-7 | 1A | training set | DMSO | 0.00002 |
| 2,4-dinitrofluorobenzene | 70-34-8 | 1A | training set | DMSO | 0.00001 |

TABLE 9-continued

Chemicals training set

| Chemical | Can | CLP | set | vehicle | GARD input [M] |
|---|---|---|---|---|---|
| 3-methylcatechol | 488-17-5 | 1A | training set | DMSO | 0.00004 |
| abietic acid | 514-10-3 | 1B | training set | DMSO | 0.000125 |
| amylcinnamyl alcohol | 101-85-9 | 1B | training set | DMSO | 0.0003 |
| aniline | 62-53-3 | 1B | training set | DMSO | 0.0005 |
| anisyl alcohol | 105-13-5 | 1B | training set | DMSO | 0.0005 |
| benzocaine | 94-09-7 | 113 | training set | DMSO | 0.0005 |
| benzyl alcohol | 100-51-6 | no cat | training set | DMSO | 0.0005 |
| chlorpromazine | 50-53-3 | 1A | training set | DM90 | 0.0000125 |
| citral | 5392-40-5 | 1B | training set | DMSO | 0.0000625 |
| citronellol | 106-22-9 | 1B | training set | DMSO | 0.0005 |
| dextran | 9004-54-0 | no cat | training set | DMSO | 0.00003 |
| diethanolamine | 111-42-2 | 1B | training set | H2O | 0.0005 |
| hexyl salicylate | 6259-76-3 | 1A | training set | DMSO | 0.00007 |
| imidazolidinyl urea | 39236-46-9 | 1B | training set | DMSO | 0.00005 |
| isopropyl myristate | 110-27-0 | 1B | training set | DMSO | 0.0005 |
| kanamycin A | 25389-940 | no cat | training set | H2O | 0.000125 |
| lilial | 80-54-6 | 1B | training set | DMSO | 0.0001875 |
| limonene | 5989-27-5 | 1B | training set | DMSO | 0.0005 |
| methyl heptine carbonate | 111-12-6 | 1A | training set | DMSO | 0.0001 |
| pentachlorophenol | 87-86-5 | 1B | training set | DMSO | 0.0000625 |
| pyridine | 110-86-1 | 1B | training set | H2O | 0.0005 |
| tartaric acid | 87-69-4 | no cat | training set | DMSO | 0.0005 |

TABLE 10

Chemicals test set

| Chemical | Cas | CLP | set | vehicle | GARD input [M] |
|---|---|---|---|---|---|
| diethyl phthalate | 84-66-2 | no cat | test set 1 | DMSO | 0.00005 |
| ethyl vanillin | 121-32-4 | no cat | test set 1 | DMSO | 0.0005 |
| diethyl maleate | 141-05-9 | 1B | test set 1 | DMSO | 0.00012 |
| xylene | 1330-20-7 | no cat | test set 1 | DMSO | 0.0005 |
| 1-brombutane | 109-65-9 | no cat | test set 1 | DMSO | 0.0005 |
| anethole | 104-46-1 | 1B | test set 1 | DMSO | 0.0005 |
| benzoic acid | 65-85-0 | no cat | test set 1 | DMSO | 0.0005 |
| benzyl benzoate | 120-51-4 | 1B | test set 1 | DMSO | 0.0003 |
| bisphenol A-diglycidyl ether | 1675-54-3 | 1A | test set 1 | DMSO | 0.00005 |
| butyl glycidyl ether | 2426-08-6 | 1B | test set 1 | DMSO | 0.0005 |
| citric acid | 77-92-9 | no cat | test set 1 | DMSO | 0.0005 |
| cyanuric chloride | 108-77-0 | 1A | test set 1 | DMSO | 0.00005 |
| glutaraldehyde | 111-30-8 | 1A | test set 1 | H2O | 0.00002 |
| iodopropynyl butylcarbamate | 55406-53-6 | 1A | test set 1 | DMSO | 0.00001 |
| linalool | 78-70-6 | 1B | test set 1 | DMSO | 0.0005 |
| lyral | 31906-04-4 | 1B | test set 1 | DMSO | 0.0001 |
| p-benzochinone | 106-51-4 | 1A | test set 1 | DMSO | 0.00005 |
| propyl gal late | 121-79-9 | 1A | test set 1 | DMSO | 0.000125 |

TABLE 11

Model performance - external test set

| | CLP 1A | CLP 1B | CLP no cat |
|---|---|---|---|
| Accuracy | 0.93 | 0.76 | 0.90 |
| Sensitivity | 0.86 | 0.63 | 1.0 |
| Specificity | 1.0 | 0.90 | 0.80 |

TABLE 12

| Ranking | Variable frequencies | Transcript Cluster ID | Gene Title | Gene Symbol |
|---|---|---|---|---|
| 1 | 0.335 | 8117408 | histone cluster 1, h2ab///histone cluster 1, H2ae | HI5T1H2A8///HIST1H2AB |
| 2 | 0.235 | 8102643 | cyclin A2 | CCNA2 |
| 3 | 0.22 | 8004804 | phosphoribosylformylglycinamidine synthase | PFAS |
| 4 | 0.21 | 8151252 | — | — |
| 5 | 0.175 | 8006634 | phosphatidylinositol glycan anchor biosynthesis, class W | PIGW |
| 6 | 0.165 | 8020411 | small nuclear ribonucleoprotein D1 polypeptide 16 kDa | SNRPD1 |
| 7 | 0.16 | 7935403 | Rho GTPase activating protein 19///ARHGAP19-SLIT1 readthrough (NM | ARHGAP19///ARHGAP19 |
| 8 | 0.145 | 8124391 | histone cluster 1, H2ab | HIST1H2AB |
| 9 | 0.1 | 8174610 | leucine-rich repeats and calponin homology (CH) domain containing 2 | LRCH2 |
| 10 | 0.085 | 8170468 | high mobility group box 3 | HMGB3 |
| 11 | 0.08 | 8045678 | plakophilin 4///plakophilin 4 | PKP4///PKP4 |
| 12 | 0.07 | 7902023 | ribonucleoprotein, PTD binding 2///ribonucleoprotein, PTB binding 2 | RAVER2///RAVER2 |
| 13 | 0.06 | 7983594 | deoxyuridine triphosphatase /// deoxyuridine triphosphatase | DUT///DUT |
| 14 | 0.06 | 8067167 | aurora kinase A | AURKA |
| 15 | 0.045 | 8055309 | — | — |
| 16 | 0.03 | 7916316 | NDC1 transmembrane nucleoporin | NDC1 |
| 17 | 0.03 | 7994620 | kinesin family member 22///kinesin family member 22 | KIF22///KIF22 |
| 18 | 0.025 | 7970828 | OK/SW-CL.58 | OK/SW-CL.58 |

TABLE 12-continued

| | | | | |
|---|---|---|---|---|
| 19 | 0.195 | 7994343 | | |
| 20 | 0.15 | 8141395 | minichromosome maintenance complex component 7 | MCM7 |

| Transcript Cluster ID | Transcript ID |
|---|---|
| 8117408 | EMST00000303910///GENSCAN00000029B43///BC093862///NM_021052///BC093836 |
| 8102643 | ENST00000618014///ENST00000274026///GENSCAN00000033473///CR407692///BC104787///BC104783///AK291931///NM_001237 |
| 8004804 | ENST00000314666 //// ENST000000546020///ENST00000580356///BC031807///GENSCAN00000001671///BC167158///BC146768///AK295895///AK292804///XM_006721546///AK292402///NM_012393 |
| 8151252 | ENST00000521867///GENSCAN00000046362 |
| 8006634 | ENST00000620233///ENST00000614443///ENST00000619326///ENST00000616581///AB097518///NM_178517 |
| 8020411 | ENST00000582475///ENSt00000579618///ENsT00000303413///BC001721///BC072427///J03798///NM_00291916///NM_006938 |
| 7935403 | ENST00000358308///ENST00000466484///ENST00000371027///ENST00000487035///ENST0000058531///ENST00000492211///ENST00000479633///DQ338460///GENSCAN00000038278///BC114490///BC113888///AY36750///AK303055///AK093316///NR_037909///AK090447 ///NM_001256423///NM_032900///NM_001204300 |
| 8124391 | ENST00000615868///GENSCAN00000029813///AK311785///BC25140///NM_003513 |
| 8174610 | ENST00000538422///ENST00000317135///GENSCAN00000029788///BC125224///NM_020871///NM_001243963 |
| 8170468 | ENST00000325307///BX537505///NM_005342 |
| 8045860 | ENST00000480171///ENST00000421462///ENST00000452162///ENST00000389759///ENST00000389757///ENST00000426248///GENSCAN00000017165///BC034473///BC050308///AK124217///AK055823///AK054911///NM_001005476///NM_003628 |
| 7902023 | ENST00000294426///EMST00000371072///GENSCAN00000026769///NM_018211///BC065303 |
| 7983594 | ENST00000558978///ENST00000455976///ENST0000558472///ENST00000331200///ENST00000559416///U90223///GENSCAN00000024989///U62891///U31930///CR541781///M89913///BC110377///CR541720///BC070339///BC033645///AK298464///AB049113///AK291515///NM_001948///NM_001025248 |
| 8067167 | ENST00000395914///ENST00000456249///ENST00000422322///ENST00000441357///ENST00000395907///ENST00000395913///ENST00000395915///ENST00000312783///ENST00000395911///ENST00000347343///ENST00000371356///D84212///B0027464///BC006423///BC002499///BC001280///AK301769///AF011468///AF008551///NM_198437///NM_198434///NM_198435///NM_198433///NM_003600///NM_198436 |
| 8055309 | — |
| 7916316 | DQ141696/// ENST00000371429///BC003082///AK302910///AK298909///AK295000///NR_033142///NM_018087///XM_006710762///NM_001168551 |
| 7994620 | ENST00000563263///ENST00000569382///ENST00000400751///ENST00000570173///ENST00000569636///ENST00000160827///ENST00000561482///L29096///GENSCAN00000029536///BT007259///BC004352///BC028155///AK316389///AK316050///NM_007317///AB017430///AK294380///NM_001256270///NM_001256269 |
| 7970828 | AB064667 |
| 7994343 | NONHSAT141477///ENST00000363268 |
| 8141395 | ENST00000354230///ENST00000621318///ENSTD0000425308///ENST00000463722///ENST00000477372///ENST00000303887///ENST00000286///ENST00000343023///ENST00000489841///GENSCAN00000001629///D86748///D55716///D28480///BC013375///BC009398///NM_182776///AK293172///NM_005916///NM_001278595 |

| Transcript Cluster ID | Transcript ID |
|---|---|
| 8117408 | ENST00000303910///GENSCAN00000029-843///BC093862///NM_021052///BC093836 |
| 8102643 | ENST00000618014///ENST00000274026///GENSCAN00000033473///CR407692///BC104787///BC104783///AK291931///NM_001237 |
| 8004804 | ENST0000314666///ENST00000546020///ENST00000580356///BC031807///GENSCAN00D0000-1671///BC167158///BC146768///AK295895///AK292804///XM_006721546///AK292402///NM_012393 |
| 8151252 | ENST00000521867//IGENSCAND000D463 62 |
| 8006634 | ENST00000620233///ENST00000614443 f/f ENST00000619326///ENST00000616581///AB097818///NM_178517 |
| 8020411 | ENST00000582475 ENST00000579618 ENST00000300413 BC001721////BC072427///103798///NM_001291916///NM_006938 |
| 7935403 | ENSTOOD00359308///ENST00000466484///ENST00000371027///ENST00000487035///ENST-00000358531///ENST00000492211///ENST00000479633///DQ338460///GENSCAN00000038278///BC114490///BC113B88///AY336750///AK303055///AK093316///NR_037909///AK090447///NM_001256423///NM_032900///NM_001204300 |
| 8124391 | ENST00000615868///GENSCAN000000298-13///AK311785///BC125140///NM_003513 |
| 8174610 | ENST00000538422///ENST00000317135///GENSCAN00000029788///BC125224///NM_020871///NM_001243963 |
| 8170468 | ENST00000325307///BX537505///NM_005342 |
| 8045860 | ENST00000480171///ENST00000421462///ENST00000452162///ENST00000389759///ENST00000389757///ENST00000426248///GENSCAN00000017165///BC034473///BC050308///AK124237///AK055823///AK054911///NM_001005476///NM_003628 |
| 7902023 | ENST00000294428///ENST00000371072///GENSCAN00000026769///NM_018211///BC065303 |
| 7983594 | ENST00000558978///ENST00000455976///ENST00000558472///ENST00000331200///ENST00000559416///U90223///GENSCAN00000024989///U62891///U31930///CR541781///M89913///BC110377///CR541720///BC070339///BC033645///AK298464///AB049113///AK291515///NM_001948///NM_001025248 |
| 8067167 | ENST00000395914///ENST00000456249///ENST00000422322///ENST00000441357///ENST00000395907///ENST00000395913///ENST00000395915///ENST00000312783///ENST00000395911///ENST00000347343///ENST00000371356///D4212///BC027464///BC006423///BC002499///BC001280///AK301769///AF011468///AF008551///NM_198437///NM_198434///NM_198435///NM_198433///NM_003600///NM_198436 |

8055309-
7916316 DQ141696///ENST00000371429///BC003082///AK302910///AK298909///AK295000///NR_033142///NM_018087///XM_006710762///NM_001168551
7994620 ENST00000563263///ENST00000569382///ENST00000400751///ENST00000570173///ENST00000569636///ENST00000160827///ENST00000561482///L29096///GENSCAN00000029536///BT007259///BC004352///BC028155///AK316389///AK316050///NM_007317///AB017430///AK294380///NM_001256270///NM_001256269
7970828 AB064667
7994343 NONHSAT141477///ENST00000363268
8141395 ENST00000354230///ENST00000621318///ENST00000425308///ENST00000463722///ENST00000477372///ENST0000303887///ENST00000485286///ENST00000343023///ENST00000489841///GENSCAN00000001629///D86748///D55716///D28480///BC013375///BCOU9398///NM_182776///AK293172///NM_005916///NM_001278595

The invention claimed is:

1. An in vitro method for measuring biomarkers for human skin sensitizers consisting of the steps of:
    a) exposing a population of dendritic cells or a population of dendritic-like cells to a test agent; and
    b) measuring in the exposed cells of step a) the expression of nucleic acid molecules encoding each of the following 51 biomarkers for human skin sensitizers: histone cluster 1, H2bm (HIST1H2BM); histone cluster 1, H4b (HIST1H4B); histone cluster 1, H1d (HIST1H1D); phosphoribosylaminoimidazole carboxylase, phosphoribosylaminoimidazole succinocarboxamide synthetase (PAICS); histone cluster 1, H4d (HIST1H4D); histone cluster 1, H2a1/histone cluster 1, H2bn (HIST1H2AL/HIST1H2BN); polo-like kinase 1 (PLK1); phosphoglycerate dehydrogenase (PHGDH); minichromosome maintenance complex component 2 (MCM2); minichromosome maintenance complex component 7 (MCM7); CD53; kinesin family member C1 (KIFC1); WEE1 G2 checkpoint kinase (WEE1); thymopoietin (TMPO); minichromosome maintenance complex component 4 (MCM4); proline/serine-rich coiled-coil 1 (PSRC1); ring finger protein 149 (RNF149); minichromosome maintenance complex component 6 (MCM6); minichromosome maintenance complex component 5 (MCM5); Fanconi anemia complementation group A (FANCA); carbamoyl-phosphate synthetase 2, aspartate transcarbamylase, and dihydroorotase (CAD); MRT4 homolog, ribosome maturation factor (MRTO4); target of EGR1, member 1 (TOE1); cell division cycle 20 (CDC20); peptidase M20 domain containing 2 (PM20D2); NmrA-like family domain containing 1 pseudogene (LOC344887); uracil DNA glycosylase (UNG); cyclin-dependent kinase inhibitor 1A (CDKN1A); histone cluster 1, H2bf (HIST1H2BF); histone cluster 1, H1b (HIST1H1B); jade family PHD finger 1 (JADE1); KIAA0125; cholinergic receptor, nicotinic alpha 5 (CHRNA5); chromatin assembly factor 1, subunit B (p60)/MORC family CW-type zinc finger 3 (CHAF1B/MORC3); sel-1 suppressor of lin-12-like 3 (SEL1L3); structure specific recognition protein 1 (SSRP1); forkhead box Ml (FOXM1); lamin B1 (LMNB1); histone cluster 1, H2ak (HIST1H2AK); centromere protein A (CENPA); non-SMC condensin I complex subunit H (NCAPH); histone cluster 1, H2bb (HIST1H2BB); ATPase, H+ transporting, lysosomal 56/58 kDa, V1 subunit B2 (ATP6V1B2); TNF receptor-associated protein 1 (TRAP1); phosphoribosylformylglycinamidine synthase (PFAS); transmembrane protein 97 (TMEM97); 24-dehydrocholesterol reductase (DHCR24); ferritin, heavy polypeptide 1 (FTH1); histone cluster 1, H2ae (HIST1H2AE); NAD(P)H dehydrogenase, quinone 1 (NQO1); and CD44.

2. The method according to claim 1,
    wherein measuring the expression of the biomarkers in step (b) is performed using binding moieties, each binding selectively to a nucleic acid molecule encoding one of the biomarkers for human skin sensitizers, and wherein the binding moieties each comprise a nucleic acid molecule.

3. An in vitro method for measuring biomarkers for human skin sensitizers comprising the steps of:
    a) exposing a population of dendritic cells or a population of dendritic-like cells to a test agent; and
    b) measuring in the exposed cells of step a) the expression of nucleic acid molecules encoding each of the following 51 biomarkers for human skin sensitizers: histone cluster 1, H2bm (HIST1H2BM); histone cluster 1, H4b (HIST1H4B); histone cluster 1, Hid (HIST1H1D); phosphoribosylaminoimidazole carboxylase, phosphoribosylaminoimidazole succinocarboxamide synthetase (PAICS); histone cluster 1, H4d (HIST1H4D); histone cluster 1, H2a1/histone cluster 1, H2bn (HIST1H2AL/HIST1H2BN); polo-like kinase 1 (PLK1); phosphoglycerate dehydrogenase (PHGDH); minichromosome maintenance complex component 2 (MCM2); minichromosome maintenance complex component 7 (MCM7); CD53; kinesin family member C1 (KIFC1); WEE1 G2 checkpoint kinase (WEE1); thymopoietin (TMPO); minichromosome maintenance complex component 4 (MCM4); proline/serine-rich coiled-coil 1 (PSRC1); ring finger protein 149 (RNF149); minichromosome maintenance complex component 6 (MCM6); minichromosome maintenance complex component 5 (MCM5); Fanconi anemia complementation group A (FANCA); carbamoyl-phosphate synthetase 2, aspartate transcarbamylase, and dihydroorotase (CAD); MRT4 homolog, ribosome maturation factor (MRTO4); target of EGR1, member 1 (TOE1); cell division cycle 20 (CDC20); peptidase M20 domain containing 2 (PM20D2); NmrA-like family domain containing 1 pseudogene (LOC344887); uracil DNA glycosylase (UNG); cyclin-dependent kinase inhibitor 1A (CDKN1A); histone cluster 1, H2bf (HIST1H2BF); histone cluster 1, H1b (HIST1H1B); jade family PHD finger 1 (JADE1); KIAA0125; cholinergic receptor, nicotinic alpha 5 (CHRNA5); chromatin assembly factor 1, subunit B (p60)/MORC family CW-type zinc finger 3 (CHAF1B/MORC3); sel-1 suppressor of lin-12-like 3 (SEL1L3); structure specific recognition protein 1 (SSRP1); forkhead box Ml (FOXM1); lamin B1 (LMNB1); histone cluster 1, H2ak (HIST1H2AK); centromere protein A (CENPA); non-SMC condensin I complex subunit H (NCAPH); histone cluster 1, H2bb (HIST1H2BB); ATPase, H+ transporting, lysosomal 56/58 kDa, V1 subunit B2 (ATP6V1B2); TNF receptor-associated protein 1 (TRAP1); phosphoribosylformylglycinamidine synthase (PFAS); transmembrane protein 97 (TMEM97); 24-dehydrocholesterol reductase (DHCR24); ferritin, heavy polypeptide 1 (FTH1); histone cluster 1, H2ae (HIST1H2AE); NAD(P)H dehydrogenase, quinone 1 (NQO1); and CD44, wherein step b) is performed using an array comprising binding moieties, wherein the binding moieties consist of different binding moieties each capable of binding selectively to a nucleic acid molecule encoding one of the 51 biomarkers for human skin sensitizers.

\* \* \* \* \*

UNITED STATES PATENT AND TRADEMARK OFFICE
CERTIFICATE OF CORRECTION

| | | |
|---|---|---|
| PATENT NO. | : 11,324,787 B2 | Page 1 of 1 |
| APPLICATION NO. | : 16/084788 | |
| DATED | : May 10, 2022 | |
| INVENTOR(S) | : Malin Marie Lindstedt et al. | |

It is certified that error appears in the above-identified patent and that said Letters Patent is hereby corrected as shown below:

On the Title Page

Item (30) "Foreign Application Priority Data" please insert the following:
--March 23, 2016 (WO) ............................ PCT/EP2016/056465--

Signed and Sealed this
Twenty-eighth Day of June, 2022

Katherine Kelly Vidal
*Director of the United States Patent and Trademark Office*